(12) United States Patent
Shen et al.

(10) Patent No.: US 11,464,876 B2
(45) Date of Patent: *Oct. 11, 2022

(54) GENETICALLY MODIFIED MOUSE COMPRISING A CHIMERIC TIGIT

(71) Applicant: Biocytogen Pharmaceuticals (Beijing) Co., Ltd., Beijing (CN)

(72) Inventors: Yuelei Shen, Beijing (CN); Yang Bai, Beijing (CN); Rui Huang, Beijing (CN); Yanan Guo, Beijing (CN); Xiaofei Zhou, Beijing (CN); Meiling Zhang, Beijing (CN)

(73) Assignee: Biocytogen Pharmaceuticals (Beijing) Co., Ltd., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/428,906

(22) Filed: May 31, 2019

(65) Prior Publication Data

US 2019/0351075 A1 Nov. 21, 2019

Related U.S. Application Data

(63) Continuation of application No. 16/329,442, filed as application No. PCT/CN2017/099576 on Aug. 30, 2017.

(30) Foreign Application Priority Data

Aug. 31, 2016 (CN) .......................... 201610784998.8
Aug. 29, 2017 (CN) .......................... 201710757916.5

(51) Int. Cl.
| | | |
|---|---|---|
| *A01K 67/027* | (2006.01) | |
| *A61K 49/00* | (2006.01) | |
| *C07K 14/705* | (2006.01) | |
| *C12N 15/85* | (2006.01) | |

(52) U.S. Cl.
CPC ...... *A61K 49/0008* (2013.01); *A01K 67/0276* (2013.01); *A01K 67/0278* (2013.01); *C07K 14/70503* (2013.01); *C12N 15/8509* (2013.01); *A01K 2207/12* (2013.01); *A01K 2207/15* (2013.01); *A01K 2217/072* (2013.01); *A01K 2217/075* (2013.01); *A01K 2227/105* (2013.01); *A01K 2267/0331* (2013.01); *C07K 2319/03* (2013.01); *C12N 2015/8572* (2013.01)

(58) Field of Classification Search
None
See application file for complete search history.

(56) References Cited

U.S. PATENT DOCUMENTS

| 4,683,195 A | 7/1987 | Mullis et al. |
| 2015/0106961 A1 | 4/2015 | Rojas et al. |
| 2016/0176963 A1 | 6/2016 | Maurer et al. |

FOREIGN PATENT DOCUMENTS

| CN | 1323583 | 7/2007 | |
| CN | 104561095 | 4/2015 | |
| CN | 104655854 | 5/2015 | |
| CN | 105492025 | 4/2016 | |
| WO | WO 2006/096491 | 9/2006 | |
| WO | WO-2009126688 A2 * | 10/2009 | ........... G01N 33/505 |
| WO | WO 2012/120125 | 9/2012 | |
| WO | WO-2013063556 A1 * | 5/2013 | ......... C07K 14/5412 |
| WO | WO 2014/089169 | 6/2014 | |
| WO | WO 2015/140347 | 9/2015 | |
| WO | WO 2016/028656 | 2/2016 | |
| WO | WO 2016/094481 | 6/2016 | |
| WO | WO-2016094481 A1 * | 6/2016 | ......... A01K 67/0278 |
| WO | WO 2016/175285 | 11/2016 | |
| WO | WO 2016/196237 | 12/2016 | |
| WO | WO 2017/053748 | 3/2017 | |

OTHER PUBLICATIONS

Kosicki et al Nature Biotechnology, 1-8 (Year: 2018).*
Porteus Nature Biotechnology,vol. 23, No. 8, 967-973 (Year: 2005).*
Hauschild PNAS, 108 (29), 12013-12017 (Year: 2011).*
Sigmund Arterioscler Throm Vase Biol 20:1425-1429 (Year: 2000).*
Gama Sosa et al Brain Struct Funct , 214:91-109 (Year: 2010).*
Ristevski,Molecular Biotechnology, 153-163 (Year: 2005).*
Munoz et al. Stem Cell Rev. and Rep., vol. 5, 6-9 (Year: 2009).*
Wheeler Theriogenology., 56, 1345-1369 (Year: 2001).*
Tong et al Nature Protocol, 827-844 (Year: 2011).*
Sannamed et al Annals of Oncology, 27, 7, 1190-1198 (Year: 2016).*
Topalian et al Cancer Cell, 27, 450-461 (Year: 2015).*
Stanietsky et al Eur J Immunol. 43(8): 2138-2150 (Year: 2013).*
Lute et al Blood. 106:3127-3133 (Year: 2005).*
Zhu, F Nature communications 10.1 : 1-13 (Year: 2019).*
Maksimenko et al., Acta Naturae, vol. 5, No. 1, p. 33-46 (Year: 2013).*
Ratte, J. Exp. & Clin. Cancer Res., vol. 38, No. 255, p. 1-12 (Year: 2019).*
Extended European Search Report in EP Appln. No. 17845422, dated Feb. 5, 2020, 9 pages.
Lute et al., "Human CTLA4 knock-in mice unravel the quantitative link between tumor immunity and autoimmunity induced by anti-CTLA-4 antibodies," Blood, 2005, 106(9):3127-3133.
Sanmamed et al., "Defining the optimal murine models to investigate immune checkpoint blockers and their combination with other immunotherapies," Annals of Oncology, 2016, 27(7):1190-1198.
Topalian et al., "Immune Checkpoint Blockade: A Common Denominator Approach to Cancer Therapy," Cancer Cell, 2015, 27(4):450-461.
GenBank Accession No. EU675310.1, "*Homo sapiens* T cell immunoreceptor with Ig and ITIM domains (TIGIT) mRNA, complete cds," GenBank, Apr. 23, 2008, 2 pages.

(Continued)

*Primary Examiner* — Anoop K Singh
(74) *Attorney, Agent, or Firm* — Fish & Richardson P.C.

(57) ABSTRACT

The present disclosure relates to the genetically modified non-human animals that express a human or chimeric TIGIT (e.g., humanized TIGIT), and methods of use thereof.

5 Claims, 24 Drawing Sheets

Specification includes a Sequence Listing.

(56) References Cited

OTHER PUBLICATIONS

GenBank Accession No. EU675311.1, "Mus musculus T cell immunoreceptor with Ig and ITIM domains (Tigit) mRNA, complete cds," GenBank, Apr. 23, 2008, 2 pages.

Anderson et al., "Lag-3, Tim-3, and TIGIT: Co-inhibitory receptors with specialized functions in immune regulation," Immunity, 2016, 44(5):989-1004.

Auerbach et al., "Establishment and Chimera Analysis of 129/SvEv- and C57BL/6-Derived Mouse Embryonic Stem Cell Lines" BioTechniques, 2000, 29:1024-1032.

Chan et al., "Receptors that interact with nectin and nectin-like proteins in the immunosurveillance and immunotherapy of cancer," Current Opinion in Immunology, 2012, 24:246-251.

Chen et al., "T-cell immunoreceptor with Ig and ITIM domains precursor [Mus musculus," Accession No. NP_001139797.1, NCBI GenBank, 2016, 3 pages.

Festing et al., "Revised nomenclature for strain 129 mice," Mammalian Genome, 1999, 10:836.

Ito et al., "NOD/SCID ycnull mouse: an excellent recipient mouse model for engraftment of human cells," Blood, 2002, 100(9):3175-3182.

PCT International Preliminary Report on Patentability in International Appln. No. PCT/CN2017/099576, dated Mar. 5, 2019, 6 pages.

PCT International Search Report and Written Opinion in International Appln. No. PCT/CN2017/099576, dated Nov. 16, 2017, 12 pages.

Yin et al., "Delivery technologies for genome editing." Nature Reviews Drug Discovery, 2017, 16(6):387-399.

Zhang et al., "T-cell immunoreceptor with Ig and ITIM domains precursor [*Homo sapiens*], GenBank Accession No. NP_776160.2," NCBI GenBank, 2016, 4 pages.

Zhu et al., "Humanising the mouse genome piece by piece," Nature communications, Apr. 23, 2019, 10(1):1-13.

Maksimenko et al., "Use of transgenic animals in biotechnology: prospects and problems," Acta Naturae, 2013, 5(1), 33-46.

Johnston et al., "The immunoreceptor TIGIT regulates antitumor and antiviral CD8+ T cell effector function," Cancer cell, Dec. 8, 2014, 26(6):923-937.

* cited by examiner

| Score | Expect | Method | Identities | Positives | Gaps |
|---|---|---|---|---|---|
| 270 bits(689) | 2e-96 | Compositional matrix adjust. | 147/246(60%) | 176/246(71%) | 7/246(2%) |

```
Mouse    1  MHGWLLLVWVQGLIQAAFLATGATAGTIDTKRNISAEEGGSVILQCHFSSDTAEVTQVDW   60
            M   LLL+W QGL QA   LA+G    GTI+T  NISAE+GGS+ILQCH SS TA+VTQV+W
Human    1  MRWCLLLIWAQGLRQAP-LASGMMTGTIETTGNISAEKGGSIILQCHLSSTTAQVTQVNW   59

Mouse   61  KQQDQLLAIYSVDLGWHVASVFSDRVVPGPSLGLTFQSLTMNDTGEYFCTYHTYPGGIYK  120
            +QQDQLLAI + DLGWH++    F DRV PGP LGLT QSLT+NDTGEYFC YHTYP G Y
Human   60  EQQDQLLAICNADLGWHISPSFKDRVAPGPGLGLTLQSLTVNDTGEYFCIYHTYPDGTYT  119

Mouse  121  GRIFLKVQESSVAQ----FQTAPLGGTMAAVLGLICLMVTGVTVLAR-KKSIRMHSIESG  175
            GRIFL+V ESSVA+       FQ   PL G MAA L +IC  V  V  L R KK++R++HS+E
Human  120  GRIFLEVLESSVAEHGARFQI-PLLGAMAATLVVICTAVIVVVALTRKKKALRIHSVEGD  178

Mouse  176  LGRTEAEPQEWNLRSLSSPGSPVQTQTAPAGPCGEQAEDDYADPQEYFNVLSYRSLESFI  235
            L R  A  +EW+  + S PGS V  + APAG CGEQ +D A+  +YFNVLSYRSL +
Human  179  LRRKSAGQEEWSPSAPSPPGSCVQAEAAPAGLCGEQRGEDCAELHDYFNVLSYRSLGNCS  238

Mouse  236  AVSKTG  241
            ++TG
Human  239  FFTETG  244
```

FIG. 23

SEQUENCE LISTING

<160> NUMBER OF SEQ ID NOS: 69

<210> SEQ ID NO 1
<211> LENGTH: 23
<212> TYPE: DNA
<213> ORGANISM: Artificial
<220> FEATURE:
<223> OTHER INFORMATION: sgRNA target sequence

<400> SEQUENCE: 1
ctgaagtgac ccaagtcgac tgg                                          23

<210> SEQ ID NO 2
<211> LENGTH: 23
<212> TYPE: DNA
<213> ORGANISM: Artificial
<220> FEATURE:
<223> OTHER INFORMATION: sgRNA target sequence

<400> SEQUENCE: 2
ctgctgcttc cagtcgactt ggg                                          23

<210> SEQ ID NO 3
<211> LENGTH: 23
<212> TYPE: DNA
<213> ORGANISM: Artificial
<220> FEATURE:
<223> OTHER INFORMATION: sgRNA target sequence

<400> SEQUENCE: 3
ggccatttat agtgttgacc tgg                                          23

<210> SEQ ID NO 4
<211> LENGTH: 23
<212> TYPE: DNA
<213> ORGANISM: Artificial
<220> FEATURE:
<223> OTHER INFORMATION: sgRNA target sequence

<400> SEQUENCE: 4
ccccaggtca acactataaa tgg                                          23

<210> SEQ ID NO 5
<211> LENGTH: 23
<212> TYPE: DNA
<213> ORGANISM: Artificial
<220> FEATURE:
<223> OTHER INFORMATION: sgRNA target sequence

<400> SEQUENCE: 5
caggcacgat agatacaaag agg                                          23

<210> SEQ ID NO 6
<211> LENGTH: 23
<212> TYPE: DNA
<213> ORGANISM: Artificial
<220> FEATURE:
<223> OTHER INFORMATION: sgRNA target sequence

<400> SEQUENCE: 6
tgtatctatc gtgcctgctg tgg                                          23

<210> SEQ ID NO 7
<211> LENGTH: 23
<212> TYPE: DNA
<213> ORGANISM: Artificial

```
<220> FEATURE:
<223> OTHER INFORMATION: sgRNA target sequence

<400> SEQUENCE: 7
ccaagtcgac tggaagcagc agg                                              23

<210> SEQ ID NO 8
<211> LENGTH: 23
<212> TYPE: DNA
<213> ORGANISM: Artificial
<220> FEATURE:
<223> OTHER INFORMATION: sgRNA target sequence

<400> SEQUENCE: 8
ggtcacttca gctgtgtcag agg                                              23

<210> SEQ ID NO 9
<211> LENGTH: 23
<212> TYPE: DNA
<213> ORGANISM: Artificial
<220> FEATURE:
<223> OTHER INFORMATION: sgRNA target sequence

<400> SEQUENCE: 9
cccaccagga tacgtatgat agg                                              23

<210> SEQ ID NO 10
<211> LENGTH: 23
<212> TYPE: DNA
<213> ORGANISM: Artificial
<220> FEATURE:
<223> OTHER INFORMATION: sgRNA target sequence

<400> SEQUENCE: 10
tgtacctatc atacgtatcc tgg                                              23

<210> SEQ ID NO 11
<211> LENGTH: 23
<212> TYPE: DNA
<213> ORGANISM: Artificial
<220> FEATURE:
<223> OTHER INFORMATION: sgRNA target sequence

<400> SEQUENCE: 11
cctatcatac gtatcctggt ggg                                              23

<210> SEQ ID NO 12
<211> LENGTH: 23
<212> TYPE: DNA
<213> ORGANISM: Artificial
<220> FEATURE:
<223> OTHER INFORMATION: sgRNA target sequence

<400> SEQUENCE: 12
ttcagtgatc gggtggtccc agg                                              23

<210> SEQ ID NO 13
<211> LENGTH: 23
<212> TYPE: DNA
<213> ORGANISM: Artificial
<220> FEATURE:
<223> OTHER INFORMATION: sgRNA target sequence

<400> SEQUENCE: 13
atcctggtgg gatttacaag ggg                                              23
```

```
<210> SEQ ID NO 14
<211> LENGTH: 23
<212> TYPE: DNA
<213> ORGANISM: Artificial
<220> FEATURE:
<223> OTHER INFORMATION: sgRNA target sequence

<400> SEQUENCE: 14
ctccccttgt aaatcccacc agg                                              23

<210> SEQ ID NO 15
<211> LENGTH: 23
<212> TYPE: DNA
<213> ORGANISM: Artificial
<220> FEATURE:
<223> OTHER INFORMATION: sgRNA target sequence

<400> SEQUENCE: 15
caaggggaga atattcctga agg                                              23

<210> SEQ ID NO 16
<211> LENGTH: 23
<212> TYPE: DNA
<213> ORGANISM: Artificial
<220> FEATURE:
<223> OTHER INFORMATION: sgRNA target sequence

<400> SEQUENCE: 16
tgtcattcat tgtcagagac tgg                                              23

<210> SEQ ID NO 17
<211> LENGTH: 23
<212> TYPE: DNA
<213> ORGANISM: Artificial
<220> FEATURE:
<223> OTHER INFORMATION: sgRNA target sequence

<400> SEQUENCE: 17
ctgagctttc ttggaccttc agg                                              23

<210> SEQ ID NO 18
<211> LENGTH: 18
<212> TYPE: DNA
<213> ORGANISM: Artificial
<220> FEATURE:
<223> OTHER INFORMATION: sgRNA sequence

<400> SEQUENCE: 18
tatctatcgt gcctgctg                                                    18

<210> SEQ ID NO 19
<211> LENGTH: 22
<212> TYPE: DNA
<213> ORGANISM: Artificial
<220> FEATURE:
<223> OTHER INFORMATION: sgRNA sequence

<400> SEQUENCE: 19
taggtatcta tcgtgcctgc tg                                               22

<210> SEQ ID NO 20
<211> LENGTH: 18
<212> TYPE: DNA
<213> ORGANISM: Artificial
<220> FEATURE:
<223> OTHER INFORMATION: sgRNA sequence
```

<400> SEQUENCE: 20
cagcaggcac gatagata                                               18

<210> SEQ ID NO 21
<211> LENGTH: 22
<212> TYPE: DNA
<213> ORGANISM: Artificial
<220> FEATURE:
<223> OTHER INFORMATION: sgRNA sequence

<400> SEQUENCE: 21
aaaccagcag gcacgataga ta                                          22

<210> SEQ ID NO 22
<211> LENGTH: 18
<212> TYPE: DNA
<213> ORGANISM: Artificial
<220> FEATURE:
<223> OTHER INFORMATION: sgRNA sequence

<400> SEQUENCE: 22
tacctatcat acgtatcc                                               18

<210> SEQ ID NO 23
<211> LENGTH: 22
<212> TYPE: DNA
<213> ORGANISM: Artificial
<220> FEATURE:
<223> OTHER INFORMATION: sgRNA sequence

<400> SEQUENCE: 23
taggtaccta tcatacgtat cc                                          22

<210> SEQ ID NO 24
<211> LENGTH: 18
<212> TYPE: DNA
<213> ORGANISM: Artificial
<220> FEATURE:
<223> OTHER INFORMATION: sgRNA sequence

<400> SEQUENCE: 24
ggatacgtat gataggta                                               18

<210> SEQ ID NO 25
<211> LENGTH: 22
<212> TYPE: DNA
<213> ORGANISM: Artificial
<220> FEATURE:
<223> OTHER INFORMATION: sgRNA sequence

<400> SEQUENCE: 25
aaacggatac gtatgatagg ta                                          22

<210> SEQ ID NO 26
<211> LENGTH: 132
<212> TYPE: DNA
<213> ORGANISM: Artificial
<220> FEATURE:
<223> OTHER INFORMATION: Synthesized sequence

<400> SEQUENCE: 26
gaattctaat acgactcact atagggggtc ttcgagaaga cctgttttag agctagaaat     60
agcaagttaa aataaggcta gtccgttatc aacttgaaaa agtggcaccg agtcggtgct    120

-continued

| | |
|---|---:|
| tttaaaggat cc | 132 |

<210> SEQ ID NO 27
<211> LENGTH: 963
<212> TYPE: DNA
<213> ORGANISM: Mus musculus

<400> SEQUENCE: 27

| | |
|---|---:|
| cttttcacca gcttggtttc accttacagc tgcagtgagc cagtttcagt tggaggagag | 60 |
| gccacatcca ctttgctgta ggcctctggt tagaagcatg catggctggc tgctcctggt | 120 |
| ctgggtccag gggctgatac aggctgcctt cctcgctaca ggagccacag caggcacgat | 180 |
| agatacaaag aggaacatct ctgcagagga aggtggctct gtcatcttac agtgtcactt | 240 |
| ctcctctgac acagctgaag tgacccaagt cgactggaag cagcaggacc agcttctggc | 300 |
| catttatagt gttgacctgg ggtggcatgt cgcttcagtc ttcagtgatc gggtggtccc | 360 |
| aggccccagc ctaggcctca ccttccagtc tctgacaatg aatgacacgg gagagtactt | 420 |
| ctgtacctat catacgtatc ctggtgggat ttacaagggg agaatattcc tgaaggtcca | 480 |
| agaaagctca gtggctcagt tccagactgc ccgcttgga ggaaccatgg ctgctgtgct | 540 |
| gggactcatt tgcttaatgg tcacaggagt gactgtactg gctagaaaga agtctattag | 600 |
| aatgcattct atagaaagtg gccttgggag aacagaagcg gagccacagg aatggaacct | 660 |
| gaggagtctc tcatcccctg gaagcccgt ccagacacaa actgccctg ctggtccctg | 720 |
| tggagagcag gcagaagatg actatgctga cccacaggaa tactttaatg tcctgagcta | 780 |
| cagaagccta gagagcttca ttgctgtatc gaagactggc taacgacagc tctctatccc | 840 |
| tctccctatg tctctctctc tctgtctctc tctgtctctc tctgtctctc tctgtctctg | 900 |
| tctctgtctc tgtctctctc tctctctctc tctctctctc tctgtgtgtg tgtgtgtgtg | 960 |
| tgt | 963 |

<210> SEQ ID NO 28
<211> LENGTH: 241
<212> TYPE: PRT
<213> ORGANISM: Mus musculus

<400> SEQUENCE: 28

Met His Gly Trp Leu Leu Val Trp Val Gln Gly Leu Ile Gln Ala
1               5                   10                  15

Ala Phe Leu Ala Thr Gly Ala Thr Ala Gly Thr Ile Asp Thr Lys Arg
            20                  25                  30

Asn Ile Ser Ala Glu Glu Gly Gly Ser Val Ile Leu Gln Cys His Phe
        35                  40                  45

Ser Ser Asp Thr Ala Glu Val Thr Gln Val Asp Trp Lys Gln Gln Asp
    50                  55                  60

Gln Leu Leu Ala Ile Tyr Ser Val Asp Leu Gly Trp His Val Ala Ser
65                  70                  75                  80

Val Phe Ser Asp Arg Val Val Pro Gly Pro Ser Leu Gly Leu Thr Phe
                85                  90                  95

Gln Ser Leu Thr Met Asn Asp Thr Gly Glu Tyr Phe Cys Thr Tyr His
            100                 105                 110

Thr Tyr Pro Gly Gly Ile Tyr Lys Gly Arg Ile Phe Leu Lys Val Gln
        115                 120                 125

Glu Ser Ser Val Ala Gln Phe Gln Thr Ala Pro Leu Gly Gly Thr Met
    130                 135                 140

```
Ala Ala Val Leu Gly Leu Ile Cys Leu Met Val Thr Gly Val Thr Val
145                 150                 155                 160

Leu Ala Arg Lys Lys Ser Ile Arg Met His Ser Ile Glu Ser Gly Leu
                165                 170                 175

Gly Arg Thr Glu Ala Glu Pro Gln Glu Trp Asn Leu Arg Ser Leu Ser
            180                 185                 190

Ser Pro Gly Ser Pro Val Gln Thr Gln Thr Ala Pro Ala Gly Pro Cys
        195                 200                 205

Gly Glu Gln Ala Glu Asp Asp Tyr Ala Asp Pro Gln Glu Tyr Phe Asn
    210                 215                 220

Val Leu Ser Tyr Arg Ser Leu Glu Ser Phe Ile Ala Val Ser Lys Thr
225                 230                 235                 240

Gly
```

<210> SEQ ID NO 29
<211> LENGTH: 2978
<212> TYPE: DNA
<213> ORGANISM: Homo sapiens

<400> SEQUENCE: 29

| | | | | | |
|---|---|---|---|---|---|
| cgtcctatct | gcagtcggct | actttcagtg | gcagaagagg | ccacatctgc | ttcctgtagg | 60 |
| ccctctgggc | agaagcatgc | gctggtgtct | cctcctgatc | tgggcccagg | ggctgaggca | 120 |
| ggctcccctc | gcctcaggaa | tgatgacagg | cacaatagaa | caacgggga | acatttctgc | 180 |
| agagaaaggt | ggctctatca | tcttacaatg | tcacctctcc | tccaccacgg | cacaagtgac | 240 |
| ccaggtcaac | tgggagcagc | aggaccagct | tctggccatt | gtaatgctg | acttggggtg | 300 |
| gcacatctcc | ccatccttca | aggatcgagt | ggccccaggt | cccggcctgg | gcctcaccct | 360 |
| ccagtcgctg | accgtgaacg | atacagggga | gtacttctgc | atctatcaca | cctaccctga | 420 |
| tgggacgtac | actgggagaa | tcttcctgga | ggtcctagaa | agctcagtgg | ctgagcacgg | 480 |
| tgccaggttc | cagattccat | gcttggagc | catggccgcg | acgctggtgg | tcatctgcac | 540 |
| agcagtcatc | gtggtggtcg | cgttgactag | aaagaagaaa | gccctcagaa | tccattctgt | 600 |
| ggaaggtgac | ctcaggagaa | atcagctgg | acaggaggaa | tggagcccca | gtgctccctc | 660 |
| acccccagga | agctgtgtcc | aggcagaagc | tgcacctgct | gggctctgtg | agagcagcg | 720 |
| gggagaggac | tgtgccgagc | tgcatgacta | cttcaatgtc | ctgagttaca | gaagcctggg | 780 |
| taactgcagc | ttcttcacag | agactggtta | gcaaccagag | gcatcttctg | gaagatacac | 840 |
| ttttgtcttt | gctattatag | atgaatatat | aagcagctgt | actctccatc | agtgctgcgt | 900 |
| gtgtgtgtgt | gtgtgtatgt | gtgtgtgtgt | tcagttgagt | gaataaatgt | catcctcttc | 960 |
| tccatcttca | tttccttggc | cttttcgttc | tattccattt | tgcattatgg | caggcctagg | 1020 |
| gtgagtaacg | tggatcttga | tcataaatgc | aaaattaaaa | aatatcttga | cctggttta | 1080 |
| aatctggcag | tttgagcaga | tcctatgtct | ctgagagaca | cattcctcat | aatggccagc | 1140 |
| attttgggct | acaaggtttt | gtggttgatg | atgaggatgg | catgactgca | gagccatcct | 1200 |
| catctcattt | tttcacgtca | ttttcagtaa | cttttcactca | ttcaaaggca | ggttataagt | 1260 |
| aagtcctggt | agcagcctct | atggggagat | ttgagagtga | ctaaatcttg | gtatctgccc | 1320 |
| tcaagaactt | acagttaaat | gggggagacaa | tgttgtcatg | aaaaggtatt | atagtaagga | 1380 |
| gagaaggaga | catacacagg | ccttcaggaa | gagacgacag | tttggggtga | ggtagttggc | 1440 |
| ataggcttat | ctgtgatgaa | gtggcctggg | agcaccaagg | ggatgttgag | gctagtctgg | 1500 |
| gaggagcagg | agtttgtct | agggaacttg | taggaaattc | ttggagctga | aagtcccaca | 1560 |

-continued

```
aagaaggccc tggcaccaag ggagtcagca aacttcagat tttattctct gggcaggcat    1620
ttcaagtttc cttttgctgt gacatactca tccattagac agcctgatac aggcctgtag    1680
cctcttccgg ccgtgtgtgc tggggaagcc ccaggaaacg cacatgccca cacagggagc    1740
caagtcgtag catttgggcc ttgatctacc ttttctgcat caatacactc ttgagccttt    1800 gaaaaagaa cgtttcccac taaaagaaa atgtggattt ttaaaatagg gactcttcct    1860 agggaaaaa gggggggctgg gagtgataga gggtttaaaa aataaacacc ttcaaactaa    1920
cttcttcgaa ccctttttatt cactccctga cgactttgtg ctggggttgg ggtaactgaa    1980
ccgcttattt ctgtttaatt gcattcaggc tggatcttag aagactttta tccttccacc    2040
atctctctca gaggaatgag cggggaggtt ggatttactg gtgactgatt ttctttcatg    2100
ggccaaggaa ctgaaagaga atgtgaagca aggttgtgtc ttgcgcatgg ttaaaaataa    2160
agcattgtcc tgcttcctaa gactttagact ggggttgaca attgttttag caacaagaca    2220
attcaactat ttctcctagg attttttatta ttattatttt ttcactttttc taccaaatgg    2280 gttacatagg aagaatgaac tgaaatctgt ccagagctcc aagtcctttg aagaaagat    2340 tagatgaacg taaaatgtt gttgtttgct gtggcagttt acagcatttt tcttgcaaaa    2400
ttagtgcaaa tctgttggaa atagaacaca attcacaaat tggaagtgaa ctaaaatgta    2460
atgacgaaaa gggagtagtg ttttgatttg gaggaggtgt atattcggca gaggttggac    2520
tgagagttgg gtgttatttta acataattat ggtaattggg aaacatttat aaacactatt    2580
gggatggtga taaaatacaa aagggcctat agatgttaga aatgggtcag gttactgaaa    2640
tgggattcaa tttgaaaaaa attttttttaa atagaactca ctgaactaga ttctcctctg    2700
agaaccagag aagaccattt catagttgga ttcctggaga catgcgctat ccaccacgta    2760
gccactttcc acatgtggcc atcaaccact taagatgggg ttagtttaaa tcaagatgtg    2820
ctgttataat tggtataagc ataaaatcac actagattct ggagatttaa tatgaataat    2880
aagaatacta tttcagtagt tttggtatat tgtgtgtcaa aatgataat attttggatg    2940 tattgggtga aataaaatat taacattaaa aaaaaaa                             2978
```

<210> SEQ ID NO 30
<211> LENGTH: 244
<212> TYPE: PRT
<213> ORGANISM: Homo sapiens

<400> SEQUENCE: 30

```
Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
```

```
            115                 120                 125
Ser Ser Val Ala Glu His Gly Ala Arg Phe Gln Ile Pro Leu Leu Gly
    130                 135                 140

Ala Met Ala Ala Thr Leu Val Val Ile Cys Thr Ala Val Ile Val Val
145                 150                 155                 160

Val Ala Leu Thr Arg Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Pro Ala
        195                 200                 205

Gly Leu Cys Gly Glu Gln Arg Gly Glu Asp Cys Ala Glu Leu His Asp
    210                 215                 220

Tyr Phe Asn Val Leu Ser Tyr Arg Ser Leu Gly Asn Cys Ser Phe Phe
225                 230                 235                 240

Thr Glu Thr Gly

<210> SEQ ID NO 31
<211> LENGTH: 352
<212> TYPE: DNA
<213> ORGANISM: Artificial
<220> FEATURE:
<223> OTHER INFORMATION: Homo sapiens and Mus musculus

<400> SEQUENCE: 31
cctcacccat aggagccaca acaggcacaa ttgaaacaac ggggaacatt tctgcagaga    60
aaggtggctc tatcatctta caatgtcacc tctcctccac cacggcacaa gtgacccagg   120
tcaactggga gcagcaggac cagcttctgg ccatttgtaa tgctgacttg ggtggcaca   180 tctccccatc cttcaaggat cgagtggccc caggtcccgg cctgggcctc accctccagt   240
cgctgaccgt gaacgataca ggggagtact tctgcatcta tcacacctac cctgatggga   300
cgtacactgg gagaatcttc ctggaggtcc tagaaagctc aggtatgtcc tt           352

<210> SEQ ID NO 32
<211> LENGTH: 735
<212> TYPE: DNA
<213> ORGANISM: Artificial
<220> FEATURE:
<223> OTHER INFORMATION: Homo sapiens and Mus musculus

<400> SEQUENCE: 32
atgcatggct ggctgctcct ggtctgggtc caggggctga tacaggctgc cttcctcgct    60
acaggagcca caacaggcac aattgaaaca cggggaaca tttctgcaga gaaaggtggc   120
tctatcatct tacaatgtca cctctcctcc accacggcac aagtgaccca ggtcaactgg   180
gagcagcagg accagcttct ggccatttgt aatgctgact ggggtggca catctcccca   240 tccttcaagg atcgagtggc cccaggtccc ggcctgggcc tcaccctcca gtcgctgacc   300
gtgaacgata caggggagta cttctgcatc tatcacacct accctgatgg gacgtacact   360
gggagaatct tcctggaggt cctagaaagc tcagaaagct cagtggctca gttccagact   420
gccccgcttg aggaaccat ggctgctgtg ctgggactca tttgcttaat ggtcacagga   480
gtgactgtac tggctagaaa gaagtctatt agaatgcatt ctatagaaag tggccttggg   540
agaacagaag cggagccaca ggaatggaac ctgaggagtc tctcatcccc tggaagccct   600
gtccagacac aaactgcccc tgctggtccc tgtggagagc aggcagaaga tgactatgct   660
```

```
gacccacagg aatactttaa tgtcctgagc tacagaagcc tagagagctt cattgctgta    720
tcgaagactg gctaa                                                      735
```

<210> SEQ ID NO 33
<211> LENGTH: 963
<212> TYPE: DNA
<213> ORGANISM: Artificial
<220> FEATURE:
<223> OTHER INFORMATION: Homo sapiens and Mus musculus

<400> SEQUENCE: 33

```
cttttcacca gcttggtttc accttacagc tgcagtgagc cagtttcagt tggaggagag     60
gccacatcca ctttgctgta ggcctctggt tagaagcatg catggctggc tgctcctggt    120
ctgggtccag gggctgatac aggctgcctt cctcgctaca ggagccacaa caggcacaat    180
tgaaacaacg gggaacattt ctgcagagaa aggtggctct atcatcttac aatgtcacct    240
ctcctccacc acggcacaag tgacccaggt caactgggag cagcaggacc agcttctggc    300
catttgtaat gctgacttgg ggtggcacat ctccccatcc ttcaaggatc gagtggcccc    360
aggtcccggc ctgggcctca ccctccagtc gctgaccgtg aacgatacag gggagtactt    420
ctgcatctat cacacctacc ctgatgggac gtacactggg agaatcttcc tggaggtcct    480
agaaagctca gtggctcagt tccagactgc cccgcttgga ggaaccatgg ctgctgtgct    540
gggactcatt tgcttaatgg tcacaggagt gactgtactg gctagaaaga agtctattag    600
aatgcattct atagaaagtg gccttgggag aacagaagcg gagccacagg aatggaacct    660 gagggagtctc tcatcccctg gaagcccgt ccagacacaa actgccctg ctggtccctg     720 tggagagcag gcagaagatg actatgctga cccacaggaa tactttaatg tcctgagcta    780
cagaagccta gagagcttca ttgctgtatc gaagactggc taacgacagc tctctatccc    840
tctccctatg tctctctctc tctgtctctc tctgtctctc tctgtctctg                900
tctctgtctc tgtctctctc tctctctctc tctctctctc tctgtgtgtg tgtgtgtgtg    960
tgt                                                                  963
```

<210> SEQ ID NO 34
<211> LENGTH: 241
<212> TYPE: PRT
<213> ORGANISM: Artificial
<220> FEATURE:
<223> OTHER INFORMATION: Homo sapiens and Mus musculus

<400> SEQUENCE: 34

```
Met His Gly Trp Leu Leu Leu Val Trp Val Gln Gly Leu Ile Gln Ala
1               5                   10                  15

Ala Phe Leu Ala Thr Gly Ala Thr Thr Gly Thr Ile Glu Thr Thr Gly
            20                  25                  30

Asn Ile Ser Ala Glu Lys Gly Gly Ser Ile Ile Leu Gln Cys His Leu
        35                  40                  45

Ser Ser Thr Thr Ala Gln Val Thr Gln Val Asn Trp Glu Gln Gln Asp
    50                  55                  60

Gln Leu Leu Ala Ile Cys Asn Ala Asp Leu Gly Trp His Ile Ser Pro
65                  70                  75                  80

Ser Phe Lys Asp Arg Val Ala Pro Gly Pro Gly Leu Gly Leu Thr Leu
                85                  90                  95

Gln Ser Leu Thr Val Asn Asp Thr Gly Glu Tyr Phe Cys Ile Tyr His
            100                 105                 110
```

```
Thr Tyr Pro Asp Gly Thr Tyr Thr Gly Arg Ile Phe Leu Glu Val Leu
        115                 120                 125

Glu Ser Ser Val Ala Gln Phe Gln Thr Ala Pro Leu Gly Gly Thr Met
    130                 135                 140

Ala Ala Val Leu Gly Leu Ile Cys Leu Met Val Thr Gly Val Thr Val
145                 150                 155                 160

Leu Ala Arg Lys Lys Ser Ile Arg Met His Ser Ile Glu Ser Gly Leu
                165                 170                 175

Gly Arg Thr Glu Ala Glu Pro Gln Glu Trp Asn Leu Arg Ser Leu Ser
            180                 185                 190

Ser Pro Gly Ser Pro Val Gln Thr Gln Thr Ala Pro Ala Gly Pro Cys
        195                 200                 205

Gly Glu Gln Ala Glu Asp Asp Tyr Ala Asp Pro Gln Glu Tyr Phe Asn
    210                 215                 220

Val Leu Ser Tyr Arg Ser Leu Glu Ser Phe Ile Ala Val Ser Lys Thr
225                 230                 235                 240

Gly

<210> SEQ ID NO 35
<211> LENGTH: 1504
<212> TYPE: DNA
<213> ORGANISM: Artificial
<220> FEATURE:
<223> OTHER INFORMATION: Mus musculus

<400> SEQUENCE: 35
ctgggttagg gactctgact ggacagctgt tcaagaggga agctggggaa tagactaaga      60
ttgggagcca agaaatctcc tggaaaccca tttctctcct gctccatttt cttttctgtt     120
tctgaggaac tcctagaaca atgttccagt tagttctctg ttggtcagaa atacctgctt     180
ctcagatttt catagtctac cactaatatg agagactaaa ttctgttgtt tctattctat     240
tacaaattgt agataaacat ttctgaggga aggaaacaaa atatttagag actatactac     300
aaattagttt aaaggctgaa cttataagac tgaaggtaga gaggagccaa ggtggggcag     360
gctggtaggg agcaaagaag ttggcttcat ctaggagaag gcctttcttc ccctcttacc     420
tctcctctac tgtcttccct tcctctcccc tccccttcct tcttctccct tcttcccctc     480
cccttccctc ccctcccctc ccctctcctc ccctcccctc ccctcccctc tcctcccctc     540
ccctcctatt ttctatgttt ccctcccctt ctcttcccct ccattacttc tcctttccct     600
tctttccctc tttctcattg tcctctcttc cccttccctc tctcttttgc tttagtttgt     660
ttctttgaca gatacatggt cttctatgt ttccaaggct ggtctggaat gcactatgat     720
cctcctgcct catcctccca tgtacttgga ttaaaaatat atgctgctac ttctggctga     780
gaagtagatt caagtttcct ttctctgtgt tctctctctc tctctctctc tctctctctc     840
tctctctctc tctctcattt tcctgacatc ccaaatgcca atcaaatagc ccagttctat     900
tttcaaaaca tagggctaga cacaaggcta gactgctgga acctagagag aagtacaaga     960
tatgttggtg tcgggctgat agtctaagtg ggaaagttaa ataagttcat tgaaagcaat    1020
cagccaccta gccaggaagc cgagcggaac atcctgagcg acaaagtgc tagaagcctt    1080 gtagtaagaa gccagacatc taataagaca acatttaata atacatcgca tgcagggaa    1140 aaggaagggc ttaaagctag ggtcctcagg taaggaggaa gcacagctct gactgatggg    1200
tgaggatgag gcaggttggc aggagcaagc ttcagaagca gccatgggga gcaggatggg    1260
aacagagtcc atgggaaagg gaccatggct ggggcttcag gcctcgagtg acaggcagag    1320
```

```
gaagaaaaac tctggaaatc aatgatggtc tctatggggg gcaccaggag agactgcaga    1380
ctgtggacat ctgttcctag agccagatct ggactctgaa ccctctggga ttcttcagga    1440
aggttgaagg gcagctgctg gccagagact cacgtgtgct tttccctcac ccataggagc    1500
caca                                                                 1504
```

<210> SEQ ID NO 36
<211> LENGTH: 53
<212> TYPE: DNA
<213> ORGANISM: Artificial
<220> FEATURE:
<223> OTHER INFORMATION: PCR primer

<400> SEQUENCE: 36

```
tttaagaagg agatatacat ggaattcctg ggttagggac tctgactgga cag           53
```

<210> SEQ ID NO 37
<211> LENGTH: 43
<212> TYPE: DNA
<213> ORGANISM: Artificial
<220> FEATURE:
<223> OTHER INFORMATION: PCR primer

<400> SEQUENCE: 37

```
tttcaattgt gcctgttgtg gctcctatgg gtgagggaaa agc                      43
```

<210> SEQ ID NO 38
<211> LENGTH: 312
<212> TYPE: DNA
<213> ORGANISM: Homo sapiens

<400> SEQUENCE: 38

```
acaggcacaa ttgaaacaac ggggaacatt tctgcagaga aaggtggctc tatcatctta    60
caatgtcacc tctcctccac cacggcacaa gtgacccagg tcaactggga gcagcaggac    120
cagcttctgg ccatttgtaa tgctgacttg gggtggcaca tctccccatc cttcaaggat    180
cgagtggccc caggtcccgg cctgggcctc accctccagt cgctgaccgt gaacgataca    240
ggggagtact tctgcatcta tcacacctac cctgatggga cgtacactgg gagaatcttc    300
ctggaggtcc ta                                                        312
```

<210> SEQ ID NO 39
<211> LENGTH: 43
<212> TYPE: DNA
<213> ORGANISM: Artificial
<220> FEATURE:
<223> OTHER INFORMATION: PCR primer

<400> SEQUENCE: 39

```
acccatagga gccacaacag gcacaattga acaacgggg aac                       43
```

<210> SEQ ID NO 40
<211> LENGTH: 43
<212> TYPE: DNA
<213> ORGANISM: Artificial
<220> FEATURE:
<223> OTHER INFORMATION: PCR primer

<400> SEQUENCE: 40

```
gacatacctg agctttctag gacctccagg aagattctcc cag                      43
```

<210> SEQ ID NO 41

```
<211> LENGTH: 1448
<212> TYPE: DNA
<213> ORGANISM: Mus musculus

<400> SEQUENCE: 41
gaaagctcag gtatgtcctt tgaggcaagg tggtagtgag ccactttctc tcacatagga      60
aacaccaccc tgacacactc taggaagtag agtgtctcaa tcttggagca ctttgaactc     120
attagaggat ctttcggggc atagtaaaga tagaacaact gaaagtgatg aacgtagaac     180
cttgtggggg cagagctagg atctgatacg ttccagaaac aaccagccga ttcccatgca     240
caaccacaga ttttgcatag gaaatccatc ttatctaaaa tgaggtgact tgcagatgag     300
gtcatacatg aaaggtgctc atttaatgac ttagtatcac tcatgcaaat tagaattagc     360
tcttaacaga ggatggccta gtcagccatc aatgggagga gaggcggccc ttggtctttc     420
aaagatcata tgccccagta caggggaatg ccagggccag gaagcgggag tgggtgggtt     480
ggggatcagg gtaggggag ggtataggg actttcagga tagcatttga aatgcaaatg      540
aagaaaatat ataattaaaa aaaagaatt agctcttaag tttgagctga tttaaaacag      600
gccacagcag gtgctgagtg aaaaagtata atagtcaccc acctttgcat gatgactatt     660
tggaagcttc aaagcttcca aatgccctca taaatgatta ttcttctaca aacatgagcc     720
aattttactg aggaaaggga ttatgaaaat cgtatctgaa agatagttta gcaaggtagt     780
aaagtgctca gcctctaatg ccagacatca taggtccaaa ccttgctgat ggattaattt     840
gtccagtcag tatggctata agattttatg agctgctaat gtgggcttgg ataacctact     900
ataagaaaaa gcccttagca tgatgccagc catatagcaa gtgccatgtt aggtgttgat     960
cattcccatc tgattgatgg ttgtggaagc taaggcttgg aattgctcag ggtgagaaag    1020
ctgattttaa atcagatgtt ctggctccat ggatcaccac actcagagct gcatactatc    1080
agttatattg gagtttaggt taagaacata tatgaattga aattatgttg gagtttaggt    1140
ttcatgagtt ttaagaataa atatactttg aaacgataaa agtttacctt aatgtttcct    1200
ttcaaacact gcttcctggc acctgtgcag tgtgcatgct atggtcttct atccctgttc    1260
ttcctgagtg agccatggct atgaccagga agggtcagc ctggcctatc atgtctaagt     1320
cctcagagca ggaggagcat gctgggactt tggagttccc aggcatggtc tttgtcctga    1380
gggatcagat actggagtct ccttccctat gatcccttgt gttcagggat gtgggacagg    1440
cttttct                                                              1448

<210> SEQ ID NO 42
<211> LENGTH: 43
<212> TYPE: DNA
<213> ORGANISM: Artificial
<220> FEATURE:
<223> OTHER INFORMATION: PCR primer

<400> SEQUENCE: 42
tcttcctgga ggtcctagaa agctcaggta tgtcctttga ggc                       43

<210> SEQ ID NO 43
<211> LENGTH: 51
<212> TYPE: DNA
<213> ORGANISM: Artificial
<220> FEATURE:
<223> OTHER INFORMATION: PCR primer

<400> SEQUENCE: 43
ttgttagcag ccggatctca ggatccagaa aaagcctgtc ccacatccct g              51
```

<210> SEQ ID NO 44
<211> LENGTH: 25
<212> TYPE: DNA
<213> ORGANISM: Artificial
<220> FEATURE:
<223> OTHER INFORMATION: PCR primer

<400> SEQUENCE: 44
cagagacacc tagcttggca cagac                                            25

<210> SEQ ID NO 45
<211> LENGTH: 26
<212> TYPE: DNA
<213> ORGANISM: Artificial
<220> FEATURE:
<223> OTHER INFORMATION: PCR primer

<400> SEQUENCE: 45
gattctccca gtgtacgtcc catcag                                           26

<210> SEQ ID NO 46
<211> LENGTH: 25
<212> TYPE: DNA
<213> ORGANISM: Artificial
<220> FEATURE:
<223> OTHER INFORMATION: PCR primer

<400> SEQUENCE: 46
tacaatgtca cctctcctcc accac                                            25

<210> SEQ ID NO 47
<211> LENGTH: 25
<212> TYPE: DNA
<213> ORGANISM: Artificial
<220> FEATURE:
<223> OTHER INFORMATION: PCR primer

<400> SEQUENCE: 47
cagttgtgag accctggaag gagtg                                            25

<210> SEQ ID NO 48
<211> LENGTH: 21
<212> TYPE: DNA
<213> ORGANISM: Artificial
<220> FEATURE:
<223> OTHER INFORMATION: PCR primer

<400> SEQUENCE: 48
ctggctaccc aagtagtcaa t                                                21

<210> SEQ ID NO 49
<211> LENGTH: 21
<212> TYPE: DNA
<213> ORGANISM: Artificial
<220> FEATURE:
<223> OTHER INFORMATION: PCR primer

<400> SEQUENCE: 49
ctggtgtctg tgccaagcta g                                                21

<210> SEQ ID NO 50
<211> LENGTH: 22
<212> TYPE: DNA
<213> ORGANISM: Artificial
<220> FEATURE:

<223> OTHER INFORMATION: PCR primer

<400> SEQUENCE: 50
cccttagcat gatgccagcc at                                              22

<210> SEQ ID NO 51
<211> LENGTH: 23
<212> TYPE: DNA
<213> ORGANISM: Artificial
<220> FEATURE:
<223> OTHER INFORMATION: PCR primer

<400> SEQUENCE: 51
catgcctggg aactccaaag tcc                                             23

<210> SEQ ID NO 52
<211> LENGTH: 21
<212> TYPE: DNA
<213> ORGANISM: Artificial
<220> FEATURE:
<223> OTHER INFORMATION: PCR primer

<400> SEQUENCE: 52
tcctctgaca cagctgaagt g                                               21

<210> SEQ ID NO 53
<211> LENGTH: 20
<212> TYPE: DNA
<213> ORGANISM: Artificial
<220> FEATURE:
<223> OTHER INFORMATION: PCR primer

<400> SEQUENCE: 53
actctcccgt gtcattcatt                                                 20

<210> SEQ ID NO 54
<211> LENGTH: 21
<212> TYPE: DNA
<213> ORGANISM: Artificial
<220> FEATURE:
<223> OTHER INFORMATION: PCR primer

<400> SEQUENCE: 54
gcacaattga acaacgggg a                                                21

<210> SEQ ID NO 55
<211> LENGTH: 20
<212> TYPE: DNA
<213> ORGANISM: Artificial
<220> FEATURE:
<223> OTHER INFORMATION: PCR primer

<400> SEQUENCE: 55
tgaaggatgg ggagatgtgc                                                 20

<210> SEQ ID NO 56
<211> LENGTH: 26
<212> TYPE: DNA
<213> ORGANISM: Artificial
<220> FEATURE:
<223> OTHER INFORMATION: PCR primer

<400> SEQUENCE: 56
tgacaggcag aggaagaaaa actctg                                          26

```
<210> SEQ ID NO 57
<211> LENGTH: 25
<212> TYPE: DNA
<213> ORGANISM: Artificial
<220> FEATURE:
<223> OTHER INFORMATION: PCR primer

<400> SEQUENCE: 57
tgcaaaatct gtggttgtgc atggg                                     25

<210> SEQ ID NO 58
<211> LENGTH: 26
<212> TYPE: DNA
<213> ORGANISM: Artificial
<220> FEATURE:
<223> OTHER INFORMATION: PCR primer

<400> SEQUENCE: 58
aggagagact gcagactgtg gacatc                                    26

<210> SEQ ID NO 59
<211> LENGTH: 25
<212> TYPE: DNA
<213> ORGANISM: Artificial
<220> FEATURE:
<223> OTHER INFORMATION: PCR primer

<400> SEQUENCE: 59
acttgggtca cttcagctgt gtcag                                     25

<210> SEQ ID NO 60
<211> LENGTH: 22
<212> TYPE: DNA
<213> ORGANISM: Artificial
<220> FEATURE:
<223> OTHER INFORMATION: PCR primer

<400> SEQUENCE: 60
gctgaccgtg aacgatacag gg                                        22

<210> SEQ ID NO 61
<211> LENGTH: 25
<212> TYPE: DNA
<213> ORGANISM: Artificial
<220> FEATURE:
<223> OTHER INFORMATION: PCR primer

<400> SEQUENCE: 61
gaatcggctg gttgtttctg gaacg                                     25

<210> SEQ ID NO 62
<211> LENGTH: 25
<212> TYPE: DNA
<213> ORGANISM: Artificial
<220> FEATURE:
<223> OTHER INFORMATION: PCR primer

<400> SEQUENCE: 62
cttccacatg agcgtggtca gggcc                                     25

<210> SEQ ID NO 63
<211> LENGTH: 25
<212> TYPE: DNA
<213> ORGANISM: Artificial
<220> FEATURE:
<223> OTHER INFORMATION: PCR primer
```

```
<400> SEQUENCE: 63
ccaagggact attttagatg ggcag                                          25

<210> SEQ ID NO 64
<211> LENGTH: 26
<212> TYPE: DNA
<213> ORGANISM: Artificial
<220> FEATURE:
<223> OTHER INFORMATION: PCR primer

<400> SEQUENCE: 64
gaagctacaa gctcctaggt aggggg                                         26

<210> SEQ ID NO 65
<211> LENGTH: 23
<212> TYPE: DNA
<213> ORGANISM: Artificial
<220> FEATURE:
<223> OTHER INFORMATION: PCR primer

<400> SEQUENCE: 65
acgggttggc tcaaaccatt aca                                            23

<210> SEQ ID NO 66
<211> LENGTH: 20
<212> TYPE: DNA
<213> ORGANISM: Artificial
<220> FEATURE:
<223> OTHER INFORMATION: PCR primer

<400> SEQUENCE: 66
cctggctcac agtgtcagag                                                20

<210> SEQ ID NO 67
<211> LENGTH: 20
<212> TYPE: DNA
<213> ORGANISM: Artificial
<220> FEATURE:
<223> OTHER INFORMATION: PCR primer

<400> SEQUENCE: 67
cagggctctc ctcgattttt                                                20

<210> SEQ ID NO 68
<211> LENGTH: 20
<212> TYPE: DNA
<213> ORGANISM: Artificial
<220> FEATURE:
<223> OTHER INFORMATION: PCR primer

<400> SEQUENCE: 68
ccctgctcgt ggtgaccgaa                                                20

<210> SEQ ID NO 69
<211> LENGTH: 20
<212> TYPE: DNA
<213> ORGANISM: Artificial
<220> FEATURE:
<223> OTHER INFORMATION: PCR primer

<400> SEQUENCE: 69
gcaggctctc tttgatctgc                                                20
```

GENETICALLY MODIFIED MOUSE COMPRISING A CHIMERIC TIGIT

CLAIM OF PRIORITY

This application claims the benefit of Chinese Patent Application App. No. 201610784998.8, filed on Aug. 31, 2016, and App. No. 201710757916.5, filed on Aug. 29, 2017 The entire contents of the foregoing are incorporated herein by reference.

TECHNICAL FIELD

This disclosure relates to genetically modified animal expressing human or chimeric (e.g., humanized) T cell immunoreceptor with Ig and ITIM domains (TIGIT), and methods of use thereof.

BACKGROUND

Cancer is currently one of the diseases that have the highest human mortality. According to the World Health Organization statistical data, in 2012 the number of global cancer incidence and death cases reached 14 million and 8.2 million, respectively. In China, the newly diagnosed cancer cases are 3.07 million, and the death toll is 2.2 million.

In recent years, antibody drug development for immunological checkpoints is considered to be a potential target for the treatment of various types of cancers. The traditional drug research and development typically use in vitro screening approaches. However, these screening approaches cannot provide the body environment (such as tumor microenvironment, stromal cells, extracellular matrix components and immune cell interaction, etc.), resulting in a higher rate of failure in drug development. In addition, in view of the differences between humans and animals, the test results obtained from the use of conventional experimental animals for in vivo pharmacological test may not be able to reflect the real disease state and the identification and interaction at the targeting sites, resulting in that the results in many clinical trials are significantly different from the animal experimental results. Therefore, the development of humanized animal models that are suitable for human antibody screening and evaluation will significantly improve the efficiency of new drug development and reduce the costs for drug research and development.

SUMMARY

This disclosure is related to TIGIT humanized animal model. The animal model can express human TIGIT or chimeric TIGIT (e.g., humanized TIGIT) protein in its body. It can be used in the studies on the function of TIGIT gene, and can be used in the screening and evaluation of anti-human TIGIT antibodies. In addition, the animal models prepared by the methods described herein can be used in drug screening, pharmacodynamics studies, treatments for immune-related diseases, and cancer therapy for human TIGIT target sites; in addition, they can be used to facilitate the development and design of new drugs, and save time and cost. In summary, this disclosure provides a powerful tool for studying the function of TIGIT protein and screening for cancer drugs.

Furthermore, the disclosure also provides TIGIT gene knockout mice. Moreover, the mice described in the present disclosure can be mated with the mice containing other human or chimeric genes (e.g., chimeric PD-1 or other immunomodulatory factors), so as to obtain a mouse having a human or chimeric protein at both alleles of the endogenous gene. The mice can also, e.g., be used for screening antibodies in the case of a combined use of drugs, as well as evaluating the efficacy of the combination therapy.

In one aspect, the disclosure relates to genetically-modified, non-human animals whose genome comprises at least one chromosome comprising a sequence encoding a human or chimeric T cell immunoreceptor with Ig and ITIM domains (TIGIT). In some embodiments, the sequence encoding the human or chimeric TIGIT is operably linked to an endogenous regulatory element at the endogenous TIGIT gene locus in the at least one chromosome. In some embodiments, the sequence encoding a human or chimeric TIGIT comprises a sequence encoding an amino acid sequence that is at least 70%, 75%, 80%, 85%, 90%, 95%, 99%, or 100% identical to human TIGIT (NP_776160.2 (SEQ ID NO: 30)). In some embodiments, the sequence encoding a human or chimeric TIGIT comprises a sequence encoding an amino acid sequence that is at least 70%, 75%, 80%, 85%, 90%, 95%, 99%, or 100% identical to SEQ ID NO: 34. In some embodiments, the sequence encoding a human or chimeric TIGIT comprises a sequence encoding an amino acid sequence that corresponds to amino acids 24-127 of SEQ ID NO: 30. In some embodiments, the animal is a mammal, e.g., a monkey, a rodent or a mouse. In some embodiments, the animal is a C57BL/6 mouse. In some embodiments, the animal does not express endogenous TIGIT. In some embodiments, the animal has one or more cells expressing human or chimeric TIGIT. In some embodiments, the animal has one or more cells expressing human or chimeric TIGIT, and human or endogenous CD155 can bind to the expressed human or chimeric TIGIT. In some embodiments, the animal has one or more cells expressing human or chimeric TIGIT, and human or endogenous CD112 can bind to the expressed human or chimeric TIGIT.

In another aspect, the disclosure relates to genetically-modified, non-human animals, wherein the genome of the animal comprises a replacement, at an endogenous TIGIT gene locus, of a sequence encoding a region of endogenous TIGIT with a sequence encoding a corresponding region of human TIGIT. In some embodiments, the sequence encoding the corresponding region of human TIGIT is operably linked to an endogenous regulatory element at the endogenous TIGIT locus, and one or more cells of the animal expresses a chimeric TIGIT. In some embodiments, the animal does not express endogenous TIGIT. In some embodiments, the region of endogenous TIGIT is the extracellular region of TIGIT. In some embodiments, the animal has one or more cells expressing a chimeric TIGIT having an extracellular region, a transmembrane region, and a cytoplasmic region, wherein the extracellular region comprises a sequence that is at least 50%, 60%, 70%, 80%, 90%, 95%, or 99% identical to the extracellular region of human TIGIT. In some embodiments, the extracellular region of the chimeric TIGIT has a sequence that has at least 10, 20, 30, 40, 50, 60, 70, 80, 90, or 100 contiguous amino acids that are identical to a contiguous sequence present in the extracellular region of human TIGIT. In some embodiments, the animal is a mouse, and the sequence encoding the region of endogenous TIGIT is Exon 1, Exon 2, Exon 3, and/or Exon 4 of the endogenous mouse TIGIT gene. In some embodiments, the animal is heterozygous with respect to the replacement at the endogenous TIGIT gene locus. In some embodiments, the animal is homozygous with respect to the replacement at the endogenous TIGIT gene locus.

In another aspect, the disclosure relates to methods for making a genetically-modified, non-human animal, including: replacing in at least one cell of the animal, at an endogenous TIGIT gene locus, a sequence encoding a region of an endogenous TIGIT with a sequence encoding a corresponding region of human TIGIT. In some embodiments, the sequence encoding the corresponding region of human TIGIT comprises exon 1, exon 2, exon 3, and/or exon 4 of a human TIGIT gene. In some embodiments, the sequence encoding the corresponding region of TIGIT comprises a portion of exon 2 of a human TIGIT gene. In some embodiments, the sequence encoding the corresponding region of human TIGIT encodes amino acids 24-127 of SEQ ID NO: 30. In some embodiments, the region is located within the extracellular region of TIGIT. In some embodiments, the animal is a mouse, and the sequence encoding the region of the endogenous TIGIT locus is exon 2 of mouse TIGIT gene.

In another aspect, the disclosure relates to non-human animals comprising at least one cell comprising a nucleotide sequence encoding a chimeric TIGIT polypeptide, wherein the chimeric TIGIT polypeptide comprises at least 50 contiguous amino acid residues that are identical to the corresponding contiguous amino acid sequence of a human TIGIT, wherein the animal expresses the chimeric TIGIT. In some embodiments, the chimeric TIGIT polypeptide has at least 50 contiguous amino acid residues that are identical to the corresponding contiguous amino acid sequence of a human TIGIT extracellular region. In some embodiments, the chimeric TIGIT polypeptide comprises a sequence that is at least 90%, 95%, or 99% identical to amino acids 24-127 of SEQ ID NO: 30. In some embodiments, the nucleotide sequence is operably linked to an endogenous TIGIT regulatory element of the animal. In some embodiments, the chimeric TIGIT polypeptide comprises an endogenous TIGIT transmembrane region and/or an endogenous TIGIT cytoplasmic region. In some embodiments, the nucleotide sequence is integrated to an endogenous TIGIT gene locus of the animal. In some embodiments, the chimeric TIGIT has at least one mouse TIGIT activity and/or at least one human TIGIT activity.

In another aspect, the disclosure relates to methods of making a genetically-modified mouse cell that expresses a chimeric TIGIT, the method including: replacing, at an endogenous mouse TIGIT gene locus, a nucleotide sequence encoding a region of mouse TIGIT with a nucleotide sequence encoding a corresponding region of human TIGIT, thereby generating a genetically-modified mouse cell that includes a nucleotide sequence that encodes the chimeric TIGIT, wherein the mouse cell expresses the chimeric TIGIT. In some embodiments, the chimeric TIGIT comprises an extracellular region of mouse TIGIT comprising a mouse signal peptide sequence; an extracellular region of human TIGIT; a transmembrane and/or a cytoplasmic region of a mouse TIGIT. In some embodiments, the nucleotide sequence encoding the chimeric TIGIT is operably linked to an endogenous TIGIT regulatory region, e.g., promoter. In some embodiments, the animal further comprises a sequence encoding an additional human or chimeric protein. In some embodiments, the additional human or chimeric protein is programmed cell death protein 1 (PD-1), CTLA-4, Lymphocyte Activating 3 (LAG-3), T-Cell Immunoglobulin And Mucin Domain-Containing Protein 3 (TIM-3), Programmed Cell Death 1 Ligand 1 (PD-L1), TNF Receptor Superfamily Member 9 (4-1BB), CD27, CD28, CD47, OX40, CD27, Glucocorticoid-Induced TNFR-Related Protein (GITR), or B And T Lymphocyte Associated (BTLA).

In some embodiments, the animal or mouse further comprises a sequence encoding an additional human or chimeric protein. In some embodiments, the additional human or chimeric protein is programmed cell death protein 1 (PD-1), CTLA-4, LAG-3, TIM-3, PD-L1, 4-1BB, CD27, CD28, CD47, OX40, CD27, GITR, or BTLA.

In another aspect, the disclosure relates to methods of determining effectiveness of an anti-TIGIT antibody for the treatment of cancer, including: administering the anti-TIGIT antibody to the animal of any one of the embodiments described herein, wherein the animal has a tumor; and determining the inhibitory effects of the anti-TIGIT antibody to the tumor. In some embodiments, the tumor comprises one or more tumor cells that express a TIGIT ligand. In some embodiments, the tumor comprises one or more cancer cells that are injected into the animal. In some embodiments, determining the inhibitory effects of the anti-TIGIT antibody to the tumor involves measuring the tumor volume in the animal. In some embodiments, the tumor cells are melanoma cells, non-small cell lung carcinoma (NSCLC) cells, small cell lung cancer (SCLC) cells, bladder cancer cells, prostate cancer cells (e.g., metastatic hormone-refractory prostate cancer), colorectal cancer cells, gastric cancer cells, and/or neuroblastoma cancer cells.

In some embodiments, the disclosure relates to methods of determining effectiveness of an anti-TIGIT antibody and an additional therapeutic agent for the treatment of a tumor, including administering the anti-TIGIT antibody and the additional therapeutic agent to the animals of any one of the embodiments described herein, wherein the animal has a tumor; and determining the inhibitory effects on the tumor. In some embodiments, the animal further comprises a sequence encoding a human or chimeric programmed cell death protein 1 (PD-1). In some embodiments, the additional therapeutic agent is an anti-PD-1 antibody. In some embodiments, the tumor comprises one or more tumor cells that express a TIGIT ligand. In some embodiments, the tumor comprises one or more tumor cells that express PD-L1 or PD-L2. In some embodiments, the tumor is caused by injection of one or more cancer cells into the animal. In some embodiments, determining the inhibitory effects of the treatment involves measuring the tumor volume in the animal. In some embodiments, the tumor comprises melanoma cells, non-small cell lung carcinoma (NSCLC) cells, small cell lung cancer (SCLC) cells, bladder cancer cells, prostate cancer cells (e.g., metastatic hormone-refractory prostate cancer cells), colorectal cancer cells, gastric cancer cells, and/or neuroblastoma cancer cells.

In another aspect, the disclosure relates to proteins comprising an amino acid sequence, wherein the amino acid sequence is one of the following: (a) an amino acid sequence set forth in SEQ ID NO: 34; (b) an amino acid sequence that is at least 90% identical to SEQ ID NO: 34; (c) an amino acid sequence that is at least 91%, 92%, 93%, 94%, 95%, 96%, 97%, 98%, or 99% identical to SEQ ID NO: 34; (d) an amino acid sequence that is different from the amino acid sequence set forth in SEQ ID NO: 34 by no more than 10, 9, 8, 7, 6, 5, 4, 3, 2 or 1 amino acid; and (e) an amino acid sequence that comprises a substitution, a deletion and/or insertion of one, two, three, four, five or more amino acids to the amino acid sequence set forth in SEQ ID NO: 34. In some embodiments, the disclosure relates to cells comprising the proteins provided herein. In some embodiments, the disclosure relates to animals comprising the proteins provided herein.

In another aspect, the disclosure relates to nucleic acids comprising a nucleotide sequence, wherein the nucleotide sequence is one of the following: (a) a sequence that encodes the protein of claim 54; (b) SEQ ID NO: 32; (c) SEQ ID NO: 33; (d) a sequence that is at least 90% identical to SEQ ID NO: 32 or SEQ ID NO: 33; (e) a sequence that is at least 91%, 92%, 93%, 94%, 95%, 96%, 97%, 98%, or 99% identical to SEQ ID NO: 32; and (f) a sequence that is at least 91%, 92%, 93%, 94%, 95%, 96%, 97%, 98%, or 99% identical to SEQ ID NO: 33. In some embodiments, the disclosure relates to cells comprising the nucleic acids provided herein. In some embodiments, the disclosure relates to animals comprising the nucleic acids provided herein.

In one aspect, the disclosure relates to a targeting vector, including a) a DNA fragment homologous to the 5' end of a region to be altered (5' arm), which is selected from the TIGIT gene genomic DNAs in the length of 100 to 10,000 nucleotides; b) a desired/donor DNA sequence encoding a donor region; and c) a second DNA fragment homologous to the 3' end of the region to be altered (3' arm), which is selected from the TIGIT gene genomic DNAs in the length of 100 to 10,000 nucleotides.

In some embodiments, a) the DNA fragment homologous to the 5' end of a region to be altered (5' arm/receptor) is selected from the nucleotide sequences that have at least 90% homology to the NCBI accession number NC_000082.6; c) the DNA fragment homologous to the 3' end of the region to be altered (3' arm/receptor) is selected from the nucleotide sequences that have at least 90% homology to the NCBI accession number NC_000082.6.

In some embodiments, a) the DNA fragment homologous to the 5' end of a region to be altered (5' arm/receptor) is selected from the nucleotides from the position 43662298 to the position 43663801 of the NCBI accession number NC_000082.6; c) the DNA fragment homologous to the 3' end of the region to be altered (3' arm/receptor) is selected from the nucleotides from the position 43660538 to the position 43661985 of the NCBI accession number NC_000082.6.

In some embodiments, a length of the selected genomic nucleotide sequence is 1.2 kb, 1.5 kb or 1 kb. In some embodiments, the region to be altered is exon 2 of TIGIT gene.

In some embodiments, the sequence of the 5' arm is shown in SEQ ID NO: 35. In some embodiments, the sequence of the 3' arm is shown in SEQ ID NO: 41.

In some embodiments, the targeting vector further includes a selectable gene marker.

In some embodiments, the target region is derived from human. In some embodiments, the target region is a part or entirety of the nucleotide sequence of a humanized TIGIT. In some embodiments, the nucleotide sequence is shown as one or more of the first exon, the second exon, the third exon, and/or the fourth exon of the DNA sequence of the human TIGIT.

In some embodiments, the nucleotide sequence of the human TIGIT encodes the human TIGIT protein with the NCBI accession number NP_776160.2 (SEQ ID NO: 30). In some embodiments, the target region is shown in SEQ ID NO: 38.

The disclosure also relates to a cell including the targeting vector as described herein.

In another aspect, the disclosure relates to an sgRNA sequence for constructing a humanized animal model, wherein the sgRNA sequence targets the TIGIT gene, the sgRNA is unique on the target sequence of the TIGIT gene to be altered, and meets the sequence arrangement rule of 5'-NNN (20)-NGG3' or 5'-CCN-N(20)-3'. In some embodiments, the targeting site of the sgRNA in the mouse TIGIT gene is located on the exon 2 of the mouse TIGIT gene.

In another aspect, the disclosure relates to an sgRNA sequence for constructing a humanized animal model, wherein an upstream sequence thereof is shown as SEQ ID NO: 18, and a downstream sequence thereof is shown as SEQ ID NO: 20, and the sgRNA sequence recognizes a 5' targeting site.

The disclosure also relates to an sgRNA sequence for constructing a humanized animal model, wherein an upstream sequence thereof is shown as SEQ ID NO: 19, which is obtained by adding TAGG to the 5' end of SEQ ID NO: 18; a downstream sequence thereof is shown as SEQ ID NO: 21, which is obtained by adding AAAC to the 5' end of SEQ ID NO: 20, and the sgRNA sequence recognizes a 5' targeting site.

The disclosure also relates to an sgRNA sequence for constructing a humanized animal model, wherein an upstream sequence thereof is shown as SEQ ID NO: 22, and a downstream sequence thereof is shown as SEQ ID NO: 24, and the sgRNA sequence recognizes a 3' targeting site.

The disclosure further relates to an sgRNA sequence for constructing a humanized animal model, wherein an upstream sequence thereof is shown as SEQ ID NO: 23, which is obtained by adding TAGG to the 5' end of SEQ ID NO: 22; a downstream sequence thereof is shown as SEQ ID NO: 25, which is obtained by adding AAAC to the 5' end of SEQ ID NO: 24, and the sgRNA sequence recognizes a 3' targeting site.

In one aspect, the disclosure relates to a construct including the sgRNA sequence as described herein.

The disclosure also relates to a cell comprising the construct as described herein.

In another aspect, the disclosure relates to a non-human mammalian cell, comprising the targeting vector as described herein, and one or more in vitro transcripts of the sgRNA construct.

In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell. In some embodiments, the cell is a germ cell. In some embodiments, the cell is a blastocyst. In some embodiments, the cell is a lymphocyte (e.g., a B-cell or a T-cell).

In another aspect, the disclosure relates to a method for establishing a TIGIT gene humanized animal model. The methods include the steps of (a) providing the cell, and preferably the cell is a fertilized egg cell;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the establishment of a humanized animal model of TIGIT gene using a gene editing technique is based on CRISPR/Cas9.

In some embodiments, the non-human mammal is mouse. In some embodiments, the mouse is a C57BL/6 mouse. In some embodiments, the non-human mammal in step (c) is a female with false pregnancy.

The disclosure also relates to a method for establishing a genetically-modified non-human animal expressing two human or chimeric (e.g., humanized) genes. The method includes the steps of (a) using the method for establishing a TIGIT gene humanized animal model to obtain a TIGIT gene genetically modified humanized mouse;

(b) mating the TIGIT gene genetically modified humanized mouse obtained in step (a) with another humanized mouse, and then screening to obtain a double humanized mouse model.

In some embodiments, in step (b), the TIGIT gene genetically modified humanized mouse obtained in step (a) is mated with a PD-1 humanized mouse to obtain a TIGIT and PD-1 double humanized mouse model.

The disclosure also relates to non-human mammal generated through the methods as described herein.

In some embodiments, the genome thereof contains human gene(s).

In some embodiments, the non-human mammal is a rodent. In some embodiments, the non-human mammal is a mouse.

In some embodiments, the non-human mammal expresses a protein encoded by a humanized TIGIT gene.

The disclosure also relates to an offspring of the non-human mammal.

In another aspect, the disclosure relates to a tumor bearing non-human mammal model, characterized in that the non-human mammal model is obtained through the method as described herein.

In some embodiments, the non-human mammal is a rodent. In some embodiments, the non-human mammal is a mouse.

The disclosure also relates to a cell or cell line, or a primary cell culture thereof derived from the non-human mammal or an offspring thereof, or the tumor bearing non-human mammal.

The disclosure further relates to the tissue, organ or a culture thereof derived from the non-human mammal or an offspring thereof, or the tumor bearing non-human mammal.

In another aspect, the disclosure relates to a tumor tissue derived from the non-human mammal or an offspring thereof when it bears a tumor, or the tumor bearing non-human mammal.

In one aspect, the disclosure relates to a TIGIT amino acid sequence of a humanized mouse, wherein the amino acid sequence is selected from the group consisting of:

a) an amino acid sequence shown in SEQ ID NO: 34;

b) an amino acid sequence having a homology of at least 90% with the amino acid sequence shown in SEQ ID NO: 34;

c) an amino acid sequence encoded by a nucleic acid sequence, wherein the nucleic acid sequence is able to hybridize to a nucleotide sequence encoding the amino acid shown in SEQ ID NO: 34 under a low stringency condition;

d) an amino acid sequence having a homology of at least 90%, 91%, 92%, 93%, 94%, 95%, 96%, 97%, 98%, or at least 99% with the amino acid sequence shown in SEQ ID NO: 34;

e) an amino acid sequence that is different from the amino acid sequence shown in SEQ ID NO: 34 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 34.

The disclosure also relates to a TIGIT DNA sequence of a humanized mouse, wherein the DNA sequence is selected from the group consisting of:

a) a DNA sequence that encodes the TIGIT amino acid sequence of a humanized mouse;

b) a DNA sequence that is shown in SEQ ID NO: 33;

c) a DNA sequence having a CDS encoding sequence as shown in SEQ ID NO: 32;

d) a DNA sequence that is able to hybridize to the nucleotide sequence as shown in SEQ ID NO: 33 or SEQ ID NO: 32 under a low stringency condition;

e) a DNA sequence that has a homology of at least 90% with the nucleotide sequence as shown in SEQ ID NO: 33 or SEQ ID NO: 32;

f) a DNA sequence that encodes an amino acid sequence, wherein the amino acid sequence has a homology of at least 90% with the amino acid sequence shown in SEQ ID NO: 34;

g) a DNA sequence that encodes an amino acid sequence, wherein the amino acid sequence has a homology of at least 90%, 91%, 92%, 93%, 94%, 95%, 96%, 97%, 98%, or at least 99% with the amino acid sequence shown in SEQ ID NO: 34;

h) a DNA sequence that encodes an amino acid sequence, wherein the amino acid sequence is different from the amino acid sequence shown in SEQ ID NO: 34 by no more than 10, 9, 8, 7, 6, 5, 4, 3, 2 or no more than 1 amino acid; and/or i) a DNA sequence that encodes an amino acid sequence, wherein the amino acid sequence comprises a substitution, a deletion and/or insertion of 1, 2, 3, 4, 5, 6, 7, 8, 9, or more amino acids to the amino acid sequence shown in SEQ ID NO: 34.

j) and optimized SEQ ID NO: 33.

The disclosure further relates to a TIGIT genomic DNA sequence of a humanized mouse, a DNA sequence obtained by a reverse transcription of the mRNA obtained by transcription thereof is consistent with or complementary to the DNA sequence; a construct expressing the amino acid sequence thereof; a cell comprising the construct thereof; a tissue comprising the cell thereof.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the tumor bearing non-human mammal, the animal model generated through the method as described herein in the production and utilization of an animal experimental disease model of an immunization processes involving human cells, the study on a pathogen, or the development of a new diagnostic strategy and/or a therapeutic strategy.

The disclosure further relates to the use of the non-human mammal or an offspring thereof, or the tumor bearing non-human mammal, the animal model generated through the methods as described herein, in the screening, verifying, evaluating or studying the TIGIT gene function, human TIGIT antibodies, the drugs or efficacies for human TIGIT targeting sites, and the drugs for immune-related diseases and antitumor drugs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 18. Mouse tail PCR identification result, where + is positive control, − is negative control (FIGS. 18A, 18B); WT is wild type, −/− is humanized PD-1 homozygous mouse, +/− is PD-1 gene humanized heterozygous mouse (FIGS. 18C, 18D).

Mouse PD-1 mRNA was detected in C57BL/6 mice; and human PD-1 mRNA was detected in humanized TIGIT/PD-1 homozygous mouse.

Figure 22:
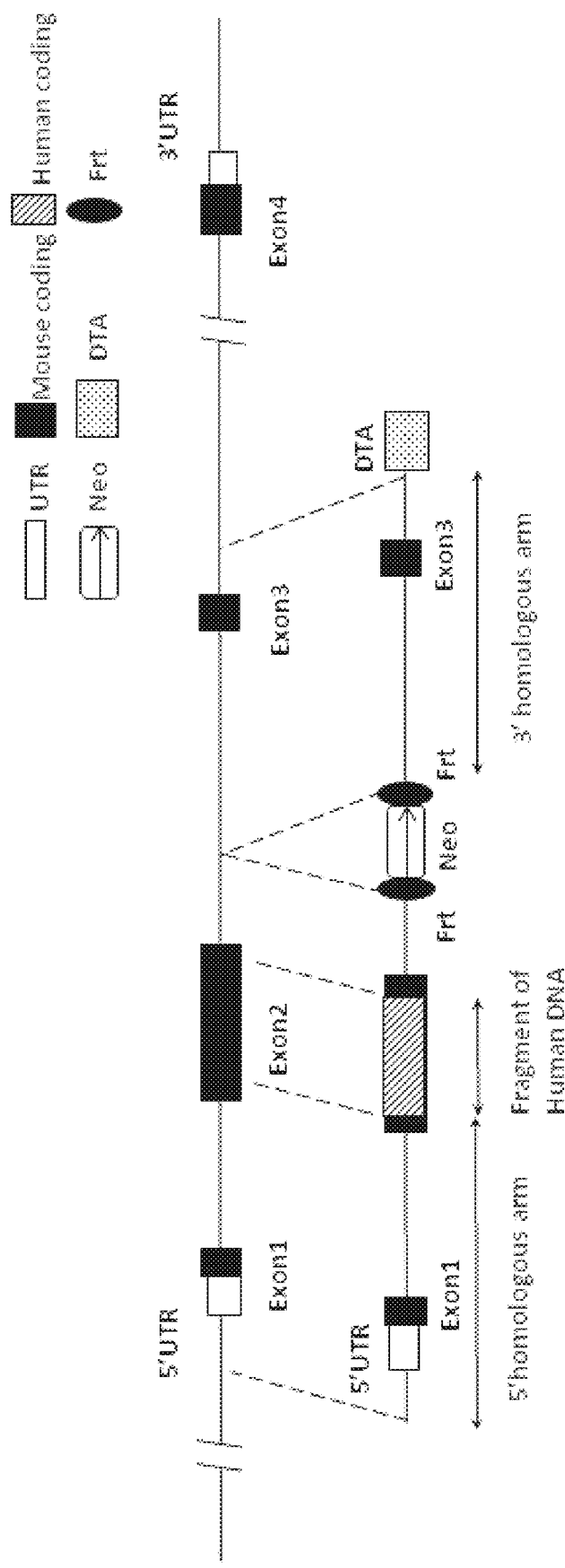

FIG. 22 is a schematic diagram of the targeting strategy for embryonic stem cells.

FIG. 23 shows the alignment between mouse TIGIT amino acid sequence (NP_001139797.1; SEQ ID NO: 28) and human TIGIT amino acid sequence (NP_776160.2; SEQ ID NO: 30).

DETAILED DESCRIPTION

This disclosure relates to transgenic non-human animal with human or chimeric (e.g., humanized) T cell immunoreceptor with Ig and ITIM domains (TIGIT), and methods of use thereof.

TIGIT is a type I transmembrane protein expressed on the surface of T cells and NK cells. It has immunoglobulin domain, transmembrane region and immunoreceptor protein tyrosine inhibitory motif. It is an immunosuppressive co-stimulatory molecule. Immunotherapy is an important area in tumor research. Clinical studies have shown that the treatment targeting the inhibitory receptors of T cells can have significant treatment effect. It has been shown in a lot of studies that TIGIT can be used as a potential target for tumor immunotherapy. When receiving the stimulation from an anti-TIGIT agonistic monoclonal antibody, TIGIT, as a receptor, is able to inhibit the activity of T cells and NK cells. TIGIT can also act as a ligand functioning on the dendritic cell (DC) surface of the poliovirus receptor (PVR), promote DC secretion of IL-10, and thus inhibiting the immune response.

TIGIT is highly expressed in chronic viral infections and in cancers. When compared with normal tissue, the ratio of TIGIT:T3 increases in T cells in cancer tissues, indicating that TIGIT is up-regulated in tumor-infiltrating T cells. Therefore, anti-TIGIT antibodies can be used in cancer treatment. Although the inhibition of PD-L1 or TIGIT alone does not yield good result, but an inhibition of both at the same time can significantly improve CD8-mediated inhibition of tumor proliferation. More importantly, only when PD-L1 and TIGIT are inhibited at the same time, IFN and TNF expression can be induced, which may be the reason for using anti-TIGIT antibody in combination with other drugs.

TIGIT was able to negatively regulate the immune response of T cells in the autoimmune response. In the TIGIT-deficient mouse models, T cells have higher reproductive capacity and can produce more pro-inflammatory cytokines. In the disease model of collagen-induced arthritis, soluble TIGIT-Fc protein can significantly inhibit the deterioration of the disease. In addition, blocking the function of anti-TIGIT will accelerate the occurrence of the disease. Therefore, TIGIT can negatively regulate the immune response of T cells, and thus participate in the inhibition of autoimmune diseases. In addition, TIGIT ligands CD155 and CD112 are overexpressed in some tumor cells, such as colorectal cancer, gastric cancer, neuroblastoma and so on. TIGIT binds to its ligand to inhibit the immune response of T cells, leading to tumor cell escape.

Both TIGIT and PD-1 have been shown to be over expressed on tumor antigen-specific (TA-specific) CD8+ T cells and CD8+ tumor infiltrating lymphocytes (TILs) from individuals with melanoma. Blockade of TIGIT and PD-1 led to increased cell proliferation, cytokine production, and degranulation of TA-specific CD8+ T cells and TIL CD8+ T cells. It can be considered an immune checkpoint.

Therefore, TIGIT antibody has great application values in the field of tumor immunotherapy. In order to make the clinical trial more effective and minimize treatment failures, the present disclosure provides methods for establishing a humanized TIGIT genetically modified animal model.

Experimental animal disease model is an indispensable research tool for studying the etiology, pathogenesis of the disease, as well as the development of prevention and control techniques and therapeutic drugs for the disease. Common experimental animals include mice, rats, guinea pigs, hamsters, rabbits, dogs, monkeys, pigs, fish and so on. However, there are many differences between human and animal genes and protein sequences, and many human proteins cannot bind to the animal's homologous proteins to produce biological activity, leading to that the results of many clinical trials do not match the results obtained from animal experiments. A large number of clinical studies are in urgent need of better animal models. With the continuous development and maturation of genetic engineering technologies, the use of human cells or genes to replace or substitute an animal's endogenous similar cells or genes to establish a biological system or disease model closer to human, and establish the humanized experimental animal models (humanized animal model) has provided an important tool for new clinical approaches or means. In this context, the genetically engineered animal model, that is, the use of genetic manipulation techniques, the use of human normal or mutant genes to replace animal homologous genes, can be used to establish the genetically modified animal models that are closer to human gene systems. The humanized animal models not only have various important applications. Due to the presence of human or humanized genes, the animals can express or express in part of the proteins with human functions, so as to greatly reduce the differences in clinical trials between humans and animals, and provide the possibility of drug screening at animal levels.

Unless otherwise specified, the practice of the methods described herein can take advantage of the techniques of cell biology, cell culture, molecular biology, transgenic biology, microbiology, recombinant DNA and immunology. These techniques are explained in detail in the following literature, for examples: Molecular Cloning A Laboratory Manual, 2nd Ed., ed. By Sambrook, Fritsch and Maniatis (Cold Spring Harbor Laboratory Press: 1989); DNA Cloning, Volumes I and II (D. N. Glovered, 1985); Oligonucleotide Synthesis (M. J. Gaited, 1984); Mullis et al U.S. Pat. No. 4,683,195; Nucleic Acid Hybridization (B. D. Hames & S. J. Higginseds. 1984); Transcription And Translation (B. D. Hames & S. J. Higginseds. 1984); Culture Of Animal Cell (R. I. Freshney, Alan R. Liss, Inc., 1987); Immobilized Cells And Enzymes (IRL Press, 1986); B. Perbal, A Practical Guide To Molecular Cloning (1984), the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calosedss, 1987, Cold Spring Harbor Laboratory); Immunochemical Methods In Cell And Molecular Biology (Mayer and Walker, eds., Academic Press, London, 1987); Hand book Of Experimental Immunology, Volumes V (D. M. Weir and C. C. Blackwell, eds., 1986); and Manipulating the Mouse Embryo, (Cold Spring Harbor Laboratory Press, Cold Spring Harbor, N.Y., 1986), each of which is incorporated herein in its entirety by reference.

T Cell Immunoreceptor with Ig and ITIM Domains (TIGIT)

TIGIT is an immune receptor present on certain T cells and Natural Killer Cells (NK). TIGIT can bind to CD155 (PVR) on dendritic cells (DCs), macrophages, etc. with high affinity, and also to CD112 (PVRL2) with lower affinity. TIGIT has been shown to be over expressed on tumor antigen-specific (TA-specific) CD8+ T cells and CD8+ tumor infiltrating lymphocytes. Blockade of TIGIT can lead to increased cell proliferation, cytokine production, and degranulation of TA-specific CD8+ T cells and TIL CD8+ T cells.

Figure 3:
FIG. 3 is a schematic diagram showing comparison of human and mouse TIGIT genes.

In human genomes, TIGIT gene locus has 4 exons, exon 1, exon 2, exon 3, and exon 4 (FIG. 3). The TIGIT protein also has an extracellular region, a transmembrane region, and a cytoplasmic region, and the signal peptide is located at the extracellular region of TIGIT. The nucleotide sequence for human TIGIT mRNA is NM_173799.3 (SEQ ID NO: 29), the amino acid sequence for human TIGIT is NP_776160.2 (SEQ ID NO: 30). The location for each exon and each region in human TIGIT nucleotide sequence and amino acid sequence is listed below:

TABLE 1

| Human TIGIT (approximate location) | NM_173799.3 (SEQ ID NO: 29) | NP_776160.2 (SEQ ID NO: 30) |
|---|---|---|
| Exon 1 | 1-137 | 1-20 |
| Exon 2 | 138-467 | 21-130 |
| Exon 3 | 468-574 | 131-166 |
| Exon 4 | 575-2394 | 167-244 |
| Signal peptide | 77-139 | 1-21 |
| Extracellular region (excluding signal peptide region) | 140-499 | 22-141 |
| Transmembrane region | 500-562 | 142-162 |
| Cytoplasmic region | 563-808 | 163-244 |
| Donor region | 146-457 (Position 157 has A to T mutation) | 24-127 |

Similarly, in mice, TIGIT gene locus has 4 exons, exon 1, exon 2, exon 3, and exon 4 (FIG. 3). The TIGIT protein also has an extracellular region, a transmembrane region, and a cytoplasmic region, and the signal peptide is located at the extracellular region of TIGIT. The nucleotide sequence for mouse TIGIT mRNA is NM_001146325.1 (SEQ ID NO: 27), the amino acid sequence for mouse TIGIT is NP_001139797.1 (SEQ ID NO: 28). The location for each exon and each region in the mouse TIGIT cDNA is listed below:

TABLE 2

| Mouse TIGIT (approximate location) | NM_001146325.1 (SEQ ID NO: 27) | NP_001139797.1 (SEQ ID NO: 28) |
|---|---|---|
| Exon 1 | 1-161 | 1-21 |
| Exon 2 | 162-491 | 22-131 |
| Exon 3 | 492-589 | 132-164 |
| Exon 4 | 590-963 | 165-241 |
| Signal peptide | 98-145 | 1-16 |
| Extracellular region (excluding signal peptide region) | 146-514 | 17-139 |
| Transmembrane region | 515-583 | 140-162 |
| Cytoplasmic region | 584-820 | 163-241 |
| Replaced region | 170-481 | 25-128 |

The mouse TIGIT gene (Gene ID: 100043314) is located in Chromosome 16 of the mouse genome, which is located from 43648861 to 43664416 of NC_000082.6 (GRCm38.p4 (GCF_000001635.24)). The 5'-UTR is from 43664184 to 43664088, exon 1 is from 43664087 to 43664024, the first intron is from 43664023 to 43662306, exon 2 is from 43662305 to 43661976, the second intron is from 43661975 to 443659537, exon 3 is from 43659536 to 43659439, the third intron is from 43659438 to 43,649235, exon 4 is from 43649234 to 43649001, the 3'-UTR is from 43649000 to 43648861, base on transcript NM_001146325.1. All relevant information for mouse TIGIT locus can be found in the NCBI website with Gene ID: 100043314, which is incorporated by reference herein in its entirety.

FIG. 23 shows the alignment between mouse TIGIT amino acid sequence (NP_001139797.1; SEQ ID NO: 28) and human TIGIT amino acid sequence (NP_776160.2 (SEQ ID NO: 30). Thus, the corresponding amino acid residue or region between human and mouse TIGIT can also be found in FIG. 23.

TIGIT genes, proteins, and locus of the other species are also known in the art. For example, the gene ID for TIGIT in *Rattus norvegicus* is 363784, the gene ID for TIGIT in *Macaca mulatta* (Rhesus monkey) is 710941, the gene ID for TIGIT in *Sus scrofa* (pig) is 100624099. The relevant information for these genes (e.g., intron sequences, exon sequences, amino acid residues of these proteins) can be found, e.g., in NCBI database.

The present disclosure provides human or chimeric (e.g., humanized) TIGIT nucleotide sequence and/or amino acid sequences. In some embodiments, the entire sequence of mouse exon 1, exon 2, exon 3, exon 4, signal peptide, extracellular region, transmembrane region, and/or cytoplasmic region are replaced by the corresponding human sequence. In some embodiments, a "region" or "portion" of mouse exon 1, exon 2, exon 3, exon 4, signal peptide, extracellular region, transmembrane region, and/or cytoplasmic region are replaced by the corresponding human sequence. The term "region" or "portion" can refer to at least 1, 2, 3, 4, 5, 6, 7, 8, 9, 10, 20, 30, 40, 50, 60, 70, 80, 90, 100, 110, 120, 130, 150, 200, 250, 300, 350, or 400 nucleotides, or at least 1, 2, 3, 4, 5, 6, 7, 8, 9, 10, 20, 30, 40, 50, 60, 70, 80, 90, 100, 110, 120, 130, or 150 amino acid residues. In some embodiments, the "region" or "portion" can be at least 50%, 55%, 60%, 65%, 70%, 75%, 80%, 85%, 90%, 95%, or 99% identical to exon 1, exon 2, exon 3, exon 4, signal peptide, extracellular region, transmembrane region, or cytoplasmic region. In some embodiments, a region, a portion, or the entire sequence of mouse exon 1, exon 2, exon 3, and/or exon 4 (e.g., exon 2) are replaced by the human exon 1, exon 2, exon 3, and/or exon 4 (e.g., exon 2) sequence.

In some embodiments, the present disclosure also provides a chimeric (e.g., humanized) TIGIT nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse TIGIT mRNA sequence (e.g., SEQ ID NO: 27), or mouse TIGIT amino acid sequence (e.g., SEQ ID NO: 28); and in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human TIGIT mRNA sequence (e.g., SEQ ID NO: 29), or human TIGIT amino acid sequence (e.g., SEQ ID NO: 30).

In some embodiments, the sequence encoding amino acids 25-128 of mouse TIGIT (SEQ ID NO: 28) is replaced.

In some embodiments, the sequence is replaced by a sequence encoding a corresponding region of human TIGIT (e.g., amino 24-127 of human TIGIT (SEQ ID NO: 30)).

In some embodiments, the nucleic acids as described herein are operably linked to a promotor or regulatory element, e.g., an endogenous mouse TIGIT promotor, an inducible promoter, an enhancer, and/or mouse or human regulatory elements.

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from a portion of or the entire mouse TIGIT nucleotide sequence (e.g., NM_001146325.1 (SEQ ID NO: 27)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire mouse TIGIT nucleotide sequence (e.g., NM_001146325.1 (SEQ ID NO: 27)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from a portion of or the entire human TIGIT nucleotide sequence (e.g., NM_173799.3 (SEQ ID NO: 29)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire human TIGIT nucleotide sequence (e.g., NM_173799.3 (SEQ ID NO: 29)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire mouse TIGIT amino acid sequence (e.g., NP_001139797.1 (SEQ ID NO: 28)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire mouse TIGIT amino acid sequence (e.g., NP_001139797.1 (SEQ ID NO: 28)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire human TIGIT amino acid sequence (e.g., NP_776160.2 (SEQ ID NO: 30)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire human TIGIT amino acid sequence (e.g., NP_776160.2 (SEQ ID NO: 30)).

The present disclosure also provides a humanized TIGIT mouse amino acid sequence, wherein the amino acid sequence is selected from the group consisting of:

a) an amino acid sequence shown in SEQ ID NO: 34;

b) an amino acid sequence having a homology of at least 90% with or at least 90% identical to the amino acid sequence shown in SEQ ID NO: 34;

c) an amino acid sequence encoded by a nucleic acid sequence, wherein the nucleic acid sequence is able to hybridize to a nucleotide sequence encoding the amino acid shown in SEQ ID NO: 34 under a low stringency condition;

d) an amino acid sequence having a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the amino acid sequence shown in SEQ ID NO: 34;

e) an amino acid sequence that is different from the amino acid sequence shown in SEQ ID NO: 34 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 34.

The present disclosure also relates to a TIGIT DNA sequence, wherein the DNA sequence can be selected from the group consisting of:

a) a DNA sequence as shown in SEQ ID NO: 32, or a DNA sequence encoding a homologous TIGIT amino acid sequence of a humanized mouse;

b) a DNA sequence that is shown in SEQ ID NO: 33;

c) a DNA sequence that is able to hybridize to the nucleotide sequence as shown in SEQ ID NO: 32 or SEQ ID NO: 33 under a low stringency condition;

d) a DNA sequence that has a homology of at least 90% or at least 90% identical to the nucleotide sequence as shown in SEQ ID NO: 32 or SEQ ID NO: 33;

e) a DNA sequence that encodes an amino acid sequence, wherein the amino acid sequence has a homology of at least 90% with or at least 90% identical to the amino acid sequence shown in SEQ ID NO: 34;

f) a DNA sequence that encodes an amino acid sequence, wherein the amino acid sequence has a homology of at least 90%, 91%, 92%, 93%, 94%, 95%, 96%, 97%, 98%, or 99% with, or at least 90%, 91%, 92%, 93%, 94%, 95%, 96%, 97%, 98%, or 99% identical to the amino acid sequence shown in SEQ ID NO: 34;

g) a DNA sequence that encodes an amino acid sequence, wherein the amino acid sequence is different from the amino acid sequence shown in SEQ ID NO: 34 by no more than 10, 9, 8, 7, 6, 5, 4, 3, 2 or no more than 1 amino acid; and/or h) a DNA sequence that encodes an amino acid sequence, wherein the amino acid sequence comprises a substitution, a deletion and/or insertion of one or more amino acids to the amino acid sequence shown in SEQ ID NO: 34.

The present disclosure further relates to a TIGIT genomic DNA sequence of a humanized mouse. The DNA sequence is obtained by a reverse transcription of the mRNA obtained by transcription thereof is consistent with or complementary to the DNA sequence homologous to the sequence shown in SEQ ID NO: 33 or SEQ ID NO: 32.

The disclosure also provides an amino acid sequence that has a homology of at least 90% with, or at least 90% identical to the sequence shown in SEQ ID NO: 34, and has protein activity. In some embodiments, the homology with the sequence shown in SEQ ID NO: 34 is at least about 90%, 91%, 92%, 93%, 94%, 95%, 96%, 97%, 98%, or at least 99%. In some embodiments, the foregoing homology is at least about 50%, 51%, 52%, 53%, 54%, 55%, 56%, 57%, 58%, or at least about 59%.

In some embodiments, the percentage identity with the sequence shown in SEQ ID NO: 34 is at least about 90%, 91%, 92%, 93%, 94%, 95%, 96%, 97%, 98%, or at least 99%. In some embodiments, the foregoing percentage identity is at least about 50%, 51%, 52%, 53%, 54%, 55%, 56%, 57%, 58%, or at least about 59%.

In some embodiments, the amino acid sequence (i) comprises an amino acid sequence; or (ii) consists of an amino acid sequence, wherein the amino acid sequence comprises any one of the sequences mentioned above.

The disclosure also provides a nucleotide sequence that has a homology of at least 90%, or at least 90% identical to the sequence shown in SEQ ID NO: 33, and has protein activity. In some embodiments, the homology with the sequence shown in SEQ ID NO: 33 is at least about 90%, 91%, 92%, 93%, 94%, 95%, 96%, 97%, 98%, or at least 99%. In some embodiments, the foregoing homology is at least about 50%, 51%, 52%, 53%, 54%, 55%, 56%, 57%, 58%, or at least about 59%.

In some embodiments, the percentage identity with the sequence shown in SEQ ID NO: 33 is at least about 90%, 91%, 92%, 93%, 94%, 95%, 96%, 97%, 98%, or at least 99%. In some embodiments, the foregoing percentage identity is at least about 50%, 51%, 52%, 53%, 54%, 55%, 56%, 57%, 58%, or at least about 59%.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, or 500 nucleotides. In some embodiments, the amino acid sequence is less than 5, 6, 7, 8, 9, 10, 20, 30, 40, 50, 60, 70, 80, 90, 100, 110, 120, 130, or 150 amino acid residues.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The term "percent homology" is often used to mean "sequence similarity." The percentage of identical residues (percent identity) and the percentage of residues conserved with similar physicochemical properties (percent similarity), e.g. leucine and isoleucine, are both used to "quantify the homology". Residues conserved with similar physicochemical properties are well known in the art. The percent homology, in many cases, is higher than the percent identity.

Cells, tissues, and animals (e.g., mouse) are also provided that comprise the nucleotide sequences as described herein, as well as cells, tissues, and animals (e.g., mouse) that express human or humanized TIGIT from an endogenous non-human TIGIT locus.

Genetically Modified Animals

As used herein, the term "genetically-modified non-human animal" refers to a non-human animal having exogenous DNA in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the exogenous DNA in its genome. The cell having exogenous DNA can be various kinds of cells, e.g., an endogenous cell, a somatic cell, an immune cell, a T cell, a B cell, a germ cell, a blastocyst, or an endogenous tumor cell. In some embodiments, genetically-modified non-human animals are provided that comprise a modified endogenous TIGIT locus that comprises an exogenous sequence (e.g., a human sequence), e.g., a replacement of one or more non-human sequences with one or more human sequences. The animals are generally able to pass the modification to progeny, i.e., through germline transmission.

As used herein, the term "chimeric gene" or "chimeric nucleic acid" refers to a gene or a nucleic acid, wherein two or more portions of the gene or the nucleic acid are from different species, or at least one of the sequences of the gene or the nucleic acid does not correspond to the wildtype nucleic acid in the animal. In some embodiment, the chimeric gene or chimeric nucleic acid has at least one portion of the sequence that is derived from two or more different sources, e.g., sequences encoding different proteins or sequences encoding the same (or homologous) protein of two or more different species. In some embodiments, the chimeric gene or the chimeric nucleic acid is a humanized gene or humanized nucleic acid.

As used herein, the term "chimeric protein" or "chimeric polypeptide" refers to a protein or a polypeptide, wherein two or more portions of the protein or the polypeptide are from different species, or at least one of the sequences of the protein or the polypeptide does not correspond to wildtype amino acid sequence in the animal. In some embodiments, the chimeric protein or the chimeric polypeptide has at least one portion of the sequence that is derived from two or more different sources, e.g., same (or homologous) proteins of different species. In some embodiments, the chimeric protein or the chimeric polypeptide is a humanized protein or a humanized polypeptide.

In some embodiments, the chimeric gene or the chimeric nucleic acid is a humanized TIGIT gene or a humanized TIGIT nucleic acid. In some embodiments, at least one or more portions of the gene or the nucleic acid is from the human TIGIT gene, at least one or more portions of the gene or the nucleic acid is from a non-human TIGIT gene. In some embodiments, the gene or the nucleic acid comprises a sequence that encodes a TIGIT protein. The encoded TIGIT protein is functional or has at least one activity of the human TIGIT protein or the non-human TIGIT protein, e.g., binding to human or non-human CD155 on dendritic cells, macrophages (e.g., with high affinity), binding to CD112 (PVRL2) (e.g., with lower affinity), decreasing T cell proliferation, and/or decreasing T cell cytokine production. Thus, blockade of TIGIT can lead to increased cell proliferation, cytokine production, and degranulation of TA-specific CD8+ T cells and TIL CD8+ T cells.

In some embodiments, the chimeric protein or the chimeric polypeptide is a humanized TIGIT protein or a humanized TIGIT polypeptide. In some embodiments, at least one or more portions of the amino acid sequence of the protein or the polypeptide is from a human TIGIT protein, and at least one or more portions of the amino acid sequence of the protein or the polypeptide is from a non-human TIGIT protein. The humanized TIGIT protein or the humanized TIGIT polypeptide is functional or has at least one activity of the human TIGIT protein or the non-human TIGIT protein The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiment, the rodent is selected from the superfamily Muroidea. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, *Malagasy* rats and mice), Platacanthomyidae (e.g., spiny dormice), and Spalacidae (e.g., mole rats, bamboo rats, and zokors). In some embodiments, the genetically modified rodent is selected from a true mouse or rat (family Muridae), a gerbil, a spiny mouse, and a crested rat. In one embodiment, the non-human animal is a mouse.

In some embodiments, the animal is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. These mice are described, e.g., in Festing et al., Revised nomenclature for strain 129 mice, Mammalian Genome 10:836 (1999); Auerbach et al., Establishment and Chimera Analysis of 129/SvEv- and C57BL/6-Derived Mouse Embryonic Stem Cell Lines (2000), which is incorporated by reference in its entirety. In some embodiments, the genetically modified mouse is a mix of the 129 strain and the C57BL/6 strain. In some embodiments, the mouse is a mix of the 129 strains, or a mix of the BL/6 strains. In some embodiment, the mouse is a BALB strain, e.g., BALB/c strain. In some embodiments, the mouse is a mix of a BALB strain and another strain. In some embodiments, the mouse is from a hybrid line (e.g., 50% BALB/c-50% 129S4/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized TIGIT animal is made. For example, suitable mice for maintaining a xenograft (e.g., a human cancer or tumor), can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes). Non-limiting examples of such mice include, e.g., NOD mice, SCID mice, NON/SCID mice, IL2Rγ knockout mice, NOD/SCID/γcnull mice (Ito, M. et al., NOD/SCID/γcnull mouse: an excellent recipient mouse model for engraftment of human cells, Blood 100(9):3175-3182, 2002), nude mice, and Rag1 and/or Rag2 knockout mice. These mice can optionally be irradiated, or otherwise treated to destroy one or more immune cell type. Thus, in various embodiments, a genetically modified mouse is provided that can include a humanization of at least a portion of an endogenous non-human TIGIT locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/SCID mice, IL-2Rγ knockout mice, NOD/SCID/γc null mice, nude mice, Rag1 and/or Rag2 knockout mice, and a combination thereof. These genetically modified animals are described, e.g., in US20150106961, which is incorporated by reference in its entirety. In some embodiments, the mouse can include a replacement of all or part of mature TIGIT coding sequence with human mature TIGIT coding sequence.

Genetically modified non-human animals that comprise a modification of an endogenous non-human TIGIT locus. In some embodiments, the modification can comprise a human nucleic acid sequence encoding at least a portion of a mature TIGIT protein (e.g., at least 10%, 20%, 30%, 40%, 50%, 60%, 70%, 80%, 90%, 95%, 96%, 97%, 98%, or 99% identical to the mature TIGIT protein sequence). Although genetically modified cells are also provided that can comprise the modifications described herein (e.g., ES cells, somatic cells), in many embodiments, the genetically modified non-human animals comprise the modification of the endogenous TIGIT locus in the germline of the animal.

Genetically modified animals can express a human TIGIT and/or a chimeric (e.g., humanized) TIGIT from endogenous mouse loci, wherein the endogenous mouse TIGIT gene has been replaced with a human TIGIT gene and/or a nucleotide sequence that encodes a region of human TIGIT sequence or an amino acid sequence that is at least 10%, 20%, 30%, 40%, 50%, 60%, 70&, 80%, 90%, 95%, 96%, 97%, 98%, or 99% identical to the human TIGIT sequence. In various embodiments, an endogenous non-human TIGIT locus is modified in whole or in part to comprise human nucleic acid sequence encoding at least one protein-coding sequence of a mature TIGIT protein.

In some embodiments, the genetically modified mice express the human TIGIT and/or chimeric TIGIT (e.g., humanized TIGIT) from endogenous loci that are under control of mouse promoters and/or mouse regulatory elements. The replacement(s) at the endogenous mouse loci provide non-human animals that express human TIGIT or chimeric TIGIT (e.g., humanized TIGIT) in appropriate cell types and in a manner that does not result in the potential pathologies observed in some other transgenic mice known in the art. The human TIGIT or the chimeric TIGIT (e.g., humanized TIGIT) expressed in animal can maintain one or more functions of the wildtype mouse or human TIGIT in the animal. Furthermore, in some embodiments, the animal does not express endogenous TIGIT. As used herein, the term "endogenous TIGIT" refers to TIGIT protein that is expressed from an endogenous TIGIT nucleotide sequence of the genetically modified non-human animal (e.g., mouse) before the genetic modification.

The genome of the animal can comprise a sequence encoding an amino acid sequence that is at least 70%, 75%, 80%, 85%, 90%, 95%, 99%, or 100% identical to human TIGIT (NP_776160.2) (SEQ ID NO: 30). In some embodiments, the genome comprises a sequence encoding an amino acid sequence that is at least 70%, 75%, 80%, 85%, 90%, 95%, 99%, or 100% identical to SEQ ID NO: 34.

The genome of the genetically modified animal can comprise a replacement at an endogenous TIGIT gene locus of a sequence encoding a region of endogenous TIGIT with a sequence encoding a corresponding region of human TIGIT. In some embodiments, the sequence that is replaced is any sequence within the endogenous TIGIT gene locus, e.g., exon 1, exon 2, exon 3, exon 4, 5'-UTR, 3'UTR, the first intron, the second intron, and the third intron, etc. In some embodiments, the sequence that is replaced is within the regulatory region of the endogenous TIGIT gene. In some embodiments, the sequence that is replaced is exon 1, exon 2, exon 3, and/or exon 4 of an endogenous mouse TIGIT gene locus.

The genetically modified animal can have one or more cells expressing a human or chimeric TIGIT (e.g., humanized TIGIT) having an extracellular region and a cytoplasmic region, wherein the extracellular region comprises a sequence that is at least 50%, 60%, 70%, 80%, 90%, 95%, 99% identical to the extracellular region of human TIGIT. In some embodiments, the extracellular region of the humanized TIGIT has a sequence that has at least 10, 20, 30, 40, 50, 60, 70, 80, 90, or 100 amino acids (e.g., contiguously or non-contiguously) that are identical to human TIGIT. Because human TIGIT and non-human TIGIT (e.g., mouse TIGIT) sequences, in many cases, are different, antibodies that bind to human TIGIT will not necessarily have the same binding affinity with mouse TIGIT or have the same effects to mouse TIGIT. Therefore, the genetically modified animal having a human or a humanized extracellular region can be used to better evaluate the effects of anti-human TIGIT antibodies in an animal model. In some embodiments, the genome of the genetically modified animal comprises a sequence encoding an amino acid sequence that corresponds to part or the entire sequence of exon 1, exon 2, exon 3, and/or exon 4 of human TIGIT, part or the entire sequence of extracellular region of human TIGIT (with or without signal peptide), or part or the entire sequence of amino acids 24-127 of SEQ ID NO: 30.

In some embodiments, the non-human animal can have, at an endogenous TIGIT gene locus, a nucleotide sequence encoding a chimeric human/non-human TIGIT polypeptide, wherein a human portion of the chimeric human/non-human TIGIT polypeptide comprises a portion of human TIGIT extracellular domain, and wherein the animal expresses a functional TIGIT on a surface of a cell of the animal. The human portion of the chimeric human/non-human TIGIT polypeptide can comprise a portion of exon 1, exon 2, exon 3, and/or exon 4 (e.g., exon 2) of human TIGIT. In some embodiments, the human portion of the chimeric human/non-human TIGIT polypeptide can comprise a sequence that is at least 80%, 85%, 90%, 95%, or 99% identical to amino acids 24-127 of SEQ ID NO: 30.

In some embodiments, the non-human portion of the chimeric human/non-human TIGIT polypeptide comprises transmembrane and/or cytoplasmic regions of an endogenous non-human TIGIT polypeptide. There may be several advantages that are associated with the transmembrane and/or cytoplasmic regions of an endogenous non-human TIGIT polypeptide. For example, once TIGIT ligand binds to TIGIT, they can properly transmit extracellular signals into the cells and regulate the downstream pathway. A human or humanized transmembrane and/or cytoplasmic regions may not function properly in non-human animal cells. In some embodiments, a few extracellular amino acids that are close to the transmembrane region of TIGIT are also derived from endogenous sequence.

Furthermore, the genetically modified animal can be heterozygous with respect to the replacement at the endogenous TIGIT locus, or homozygous with respect to the replacement at the endogenous TIGIT locus.

In some embodiments, the humanized TIGIT locus lacks a human TIGIT 5'-UTR. In some embodiment, the humanized TIGIT locus comprises a rodent (e.g., mouse) 5'-UTR. In some embodiments, the humanization comprises a human 3'-UTR. In appropriate cases, it may be reasonable to presume that the mouse and human TIGIT genes appear to be similarly regulated based on the similarity of their 5'-flanking sequence. As shown in the present disclosure, humanized TIGIT mice that comprise a replacement at an endogenous mouse TIGIT locus, which retain mouse regulatory elements but comprise a humanization of TIGIT encoding sequence, do not exhibit pathologies. Both genetically modified mice that are heterozygous or homozygous for human TIGIT are grossly normal.

The present disclosure further relates to a non-human mammal generated through the method mentioned above. In some embodiments, the genome thereof contains human gene(s).

In some embodiments, the non-human mammal is a rodent, and preferably, the non-human mammal is a mouse.

In some embodiments, the non-human mammal expresses a protein encoded by a humanized TIGIT gene.

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains the DNA encoding human TIGIT in the genome of the animal.

Figure 2:
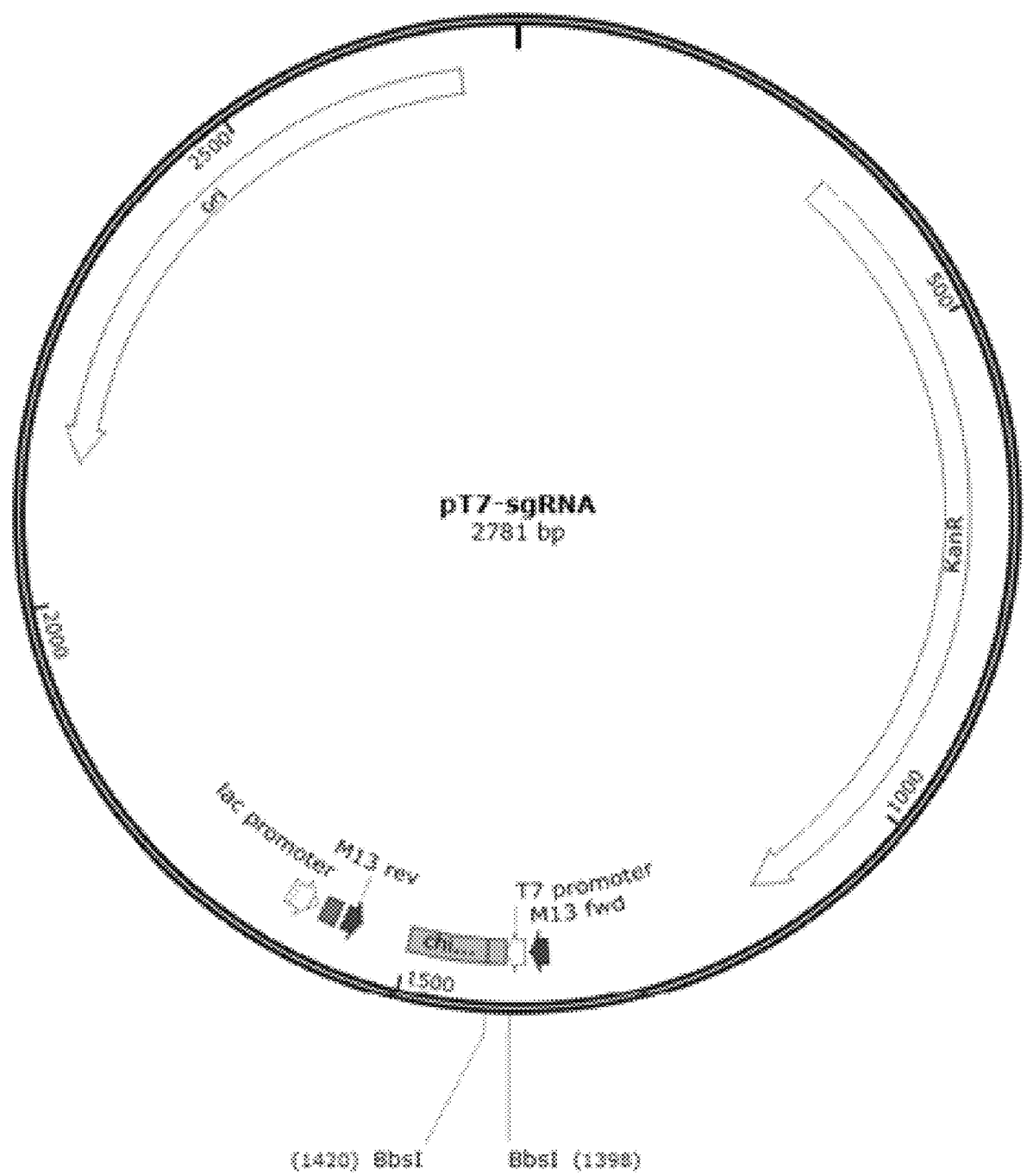
FIG. 2 is a schematic diagram showing pT7-sgRNA plasmid map.

In some embodiments, the non-human mammal comprises the genetic construct as shown in FIG. 2. In some embodiments, a non-human mammal expressing human TIGIT is provided. In some embodiments, the tissue-specific expression of human TIGIT protein is provided.

In some embodiments, the expression of human TIGIT in a genetically modified animal is controllable, as by the addition of a specific inducer or repressor substance.

Non-human mammals can be any non-human animal known in the art and which can be used in the methods as described herein. Preferred non-human mammals are mammals, (e.g., rodents). In some embodiments, the non-human mammal is a mouse.

Genetic, molecular and behavioral analyses for the non-human mammals described above can performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The integration of genetic constructs containing DNA sequences encoding human TIGIT protein can be detected by a variety of methods.

There are many analytical methods that can be used to detect exogenous DNA expression, including methods at the level of RNA (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human TIGIT protein.

Vectors

The present disclosure relates to a targeting vector, comprising: a) a DNA fragment homologous to the 5' end of a region to be altered (5' arm), which is selected from the TIGIT gene genomic DNAs in the length of 100 to 10,000 nucleotides; b) a desired/donor DNA sequence encoding a donor region; and c) a second DNA fragment homologous to the 3' end of the region to be altered (3' arm), which is selected from the TIGIT gene genomic DNAs in the length of 100 to 10,000 nucleotides.

In some embodiments, a) the DNA fragment homologous to the 5' end of a conversion region to be altered (5' arm) is selected from the nucleotide sequences that have at least 90% homology to the NCBI accession number NC_000082.6; c) the DNA fragment homologous to the 3' end of the region to be altered (3' arm) is selected from the nucleotide sequences that have at least 90% homology to the NCBI accession number NC_000082.6.

In some embodiments, a) the DNA fragment homologous to the 5' end of a region to be altered (5' arm) is selected from the nucleotides from the position 43662298 to the position 43663801 of the NCBI accession number NC_000082.6; c) the DNA fragment homologous to the 3' end of the region to be altered (3' arm) is selected from the nucleotides from the position 43660538 to the position 43661985 of the NCBI accession number NC_000082.6.

In some embodiments, the length of the selected genomic nucleotide sequence in the targeting vector can be 1.2 kb, 1.5 kb, or 1 kb.

In some embodiments, the region to be altered is exon 1, exon 2, exon 3, and/or exon 4 of TIGIT gene (e.g., exon 2 of TIGIT gene).

The targeting vector can further include a selected gene marker.

In some embodiments, the sequence of the 5' arm is shown in SEQ ID NO: 35; and the sequence of the 3' arm is shown in SEQ ID NO: 41.

In some embodiments, the target region is derived from human. For example, the target region in the targeting vector is a part or entirety of the nucleotide sequence of a human TIGIT, preferably the nucleotide sequence is shown as a first exon, a second exon, a third exon, and/or a fourth exon of the DNA sequence of the human TIGIT. In some embodiments, the nucleotide sequence of the humanized TIGIT encodes the humanized TIGIT protein with the NCBI accession number NP_776160.2 (SEQ ID NO: 30). For example, the sequence of the target region can have the sequence as shown in SEQ ID NO: 38.

The disclosure also relates to a cell comprising the targeting vectors as described above.

Moreover, the disclosure also relates to an sgRNA sequence for constructing a humanized animal model, wherein the sgRNA sequence targets the TIGIT gene, the sgRNA is unique on the target sequence of the TIGIT gene to be altered, and meets the sequence arrangement rule of 5'-NNN (20)-NGG3' or 5'-CCN-N(20)-3'; and in some embodiments, the targeting site of the sgRNA in the mouse TIGIT gene is located on the exon 1, exon 2, exon 3, or exon 4 of the mouse TIGIT gene (e.g., exon 2 of the mouse TIGIT gene).

In some embodiments, an upstream sequence thereof is shown as SEQ ID NO: 18, and a downstream sequence thereof is shown as SEQ ID NO: 20, and the sgRNA sequence recognizes a 5' targeting site. In some embodiments, the forward oligonucleotide sequence is obtained by adding TAGG to the 5' end of SEQ ID NO: 18; and the reverse oligonucleotide sequence is obtained by adding AAAC to the 5' end of SEQ ID NO: 20.

In some embodiments, the disclosure provides an sgRNA sequence for constructing a humanized animal model, wherein an upstream sequence thereof is shown as SEQ ID NO: 22, and a downstream sequence thereof is shown as SEQ ID NO: 24, and the sgRNA sequence recognizes a 3' targeting site. In some embodiments, the forward oligonucleotide sequence is obtained by adding TAGG to the 5' end of SEQ ID NO: 22; and the reverse oligonucleotide sequence is obtained by adding AAAC to the 5' end of SEQ ID NO: 24.

In some embodiments, the disclosure relates to a construct including the sgRNA sequence, and/or a cell including the construct.

In addition, the present disclosure further relates to a non-human mammalian cell, having any one of the foregoing targeting vectors, and one or more in vitro transcripts of the sgRNA construct as described herein. In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin, Hao, Kevin J. Kauffman, and Daniel G. Anderson. "Delivery technologies for genome editing." Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides replacing in at least one cell of the animal, at an endogenous TIGIT gene locus, a sequence encoding a region of an endogenous TIGIT with a sequence encoding a corresponding region of human or chimeric TIGIT. In some embodiments, the replacement occurs in a germ cell, a somatic cell, a blastocyst, or a fibroblast, etc. The nucleus of a somatic cell or the fibroblast can be inserted into an enucleated oocyte.

Figure 5:
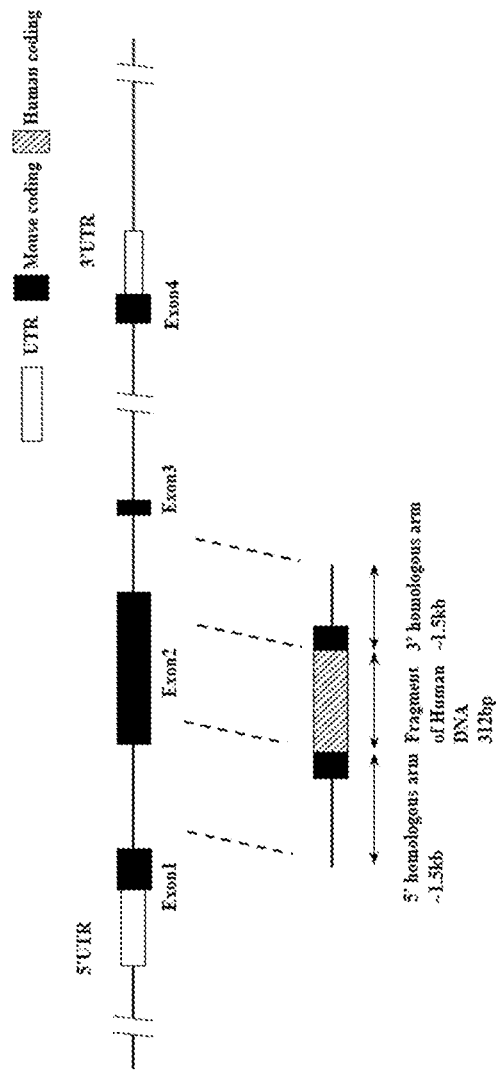
FIG. 5 is a schematic diagram showing mouse TIGIT gene targeting strategy.

FIG. 5 shows a humanization strategy for a mouse TIGIT locus. In FIG. 5, the targeting strategy involves a vector comprising the 5' end homologous arm, human TIGIT gene fragment, 3' homologous arm. The process can involve replacing endogenous TIGIT sequence with human sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous TIGIT sequence with human TIGIT sequence.

Thus, in some embodiments, the methods for making a genetically modified, humanized animal, can include the step of replacing at an endogenous TIGIT locus (or site), a nucleic acid encoding a sequence encoding a region of endogenous TIGIT with a sequence encoding a corresponding region of human TIGIT. The sequence can include a region (e.g., a part or the entire region) of exon 1, exon 2, exon 3, and/or exon 4 of a human TIGIT gene. In some embodiments, the sequence includes a region of exon 2 of a human TIGIT gene (e.g., amino acids 24-127 of SEQ ID NO: 30). In some embodiments, the region is located within the extracellular region of TIGIT. In some embodiments, the endogenous TIGIT locus is exon 1 to exon 4 of mouse TIGIT.

In some embodiments, the methods of modifying a TIGIT locus of a mouse to express a chimeric human/mouse TIGIT peptide can include the steps of replacing at the endogenous mouse TIGIT locus a nucleotide sequence encoding a mouse TIGIT with a nucleotide sequence encoding a human TIGIT, thereby generating a sequence encoding a chimeric human/mouse TIGIT.

In some embodiments, the nucleotide sequence encoding the chimeric human/mouse TIGIT can include a first nucleotide sequence encoding an extracellular region of mouse TIGIT (with or without the mouse signal peptide sequence); a second nucleotide sequence encoding an extracellular region of human TIGIT; a third nucleotide sequence encoding a transmembrane and a cytoplasmic region of a mouse TIGIT.

In some embodiments, the nucleotide sequences as described herein do not overlap with each other (e.g., the first nucleic tide sequence, the second nucleotide sequence, and/or the third nucleotide sequence do not overlap). In some embodiments, the amino acid sequences as described herein do not overlap with each other.

The present disclosure further provides a method for establishing a TIGIT gene humanized animal model, comprising the following steps:

(a) providing the cell (e.g. a fertilized egg cell) based on the methods described herein;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the non-human mammal in the foregoing method is a mouse (e.g., a C57BL/6 mouse).

In some embodiments, the non-human mammal in step (c) is a female with pseudopregnancy (or false pregnancy).

In some embodiments, the fertilized eggs for the methods described above are C57BL/6 fertilized eggs. Other fertilized eggs that can also be used in the methods as described herein include, but are not limited to, FVB/N fertilized eggs, BALB/c fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the method described above.

Methods of Using Genetically Modified Animals

Replacement of non-human genes in a non-human animal with homologous or orthologous human genes or human sequences, at the endogenous non-human locus and under control of endogenous promoters and/or regulatory elements, can result in a non-human animal with qualities and characteristics that may be substantially different from a typical knockout-plus-transgene animal. In the typical knockout-plus-transgene animal, an endogenous locus is removed or damaged and a fully human transgene is inserted into the animal's genome and presumably integrates at random into the genome. Typically, the location of the integrated transgene is unknown; expression of the human protein is measured by transcription of the human gene and/or protein assay and/or functional assay. Inclusion in the human transgene of upstream and/or downstream human sequences are apparently presumed to be sufficient to provide suitable support for expression and/or regulation of the transgene.

In some cases, the transgene with human regulatory elements expresses in a manner that is unphysiological or otherwise unsatisfactory, and can be actually detrimental to the animal. The disclosure demonstrates that a replacement with human sequence at an endogenous locus under control of endogenous regulatory elements provides a physiologically appropriate expression pattern and level that results in a useful humanized animal whose physiology with respect to the replaced gene are meaningful and appropriate and context of the humanized animal's physiology.

Genetically modified animals that express human or humanized TIGIT protein, e.g., in a physiologically appropriate manner, provide a variety of uses that include, but are not limited to, developing therapeutics for human diseases and disorders, and assessing the efficacy of these human therapeutics in the animal models.

In various aspects, genetically modified animals are provided that express human or humanized TIGIT, which are useful for testing agents that can decrease or block the interaction between TIGIT and TIGIT ligands, testing agents that can increase or decrease the immune response, and/or determining whether an agent is a TIGIT agonist or antagonist. The genetically modified animals can be, e.g., an animal model of a human disease, e.g., the disease is induced genetically (a knock-in or knockout). In various embodiments, the genetically modified non-human animals further comprise an impaired immune system, e.g., a non-human animal genetically modified to sustain or maintain a human xenograft, e.g., a human solid tumor or a blood cell tumor (e.g., a lymphocyte tumor, e.g., a B or T cell tumor).

In some embodiments, the genetically modified animals can be used for determining effectiveness of an anti-TIGIT antibody for the treatment of cancer. The methods involving administering the anti-TIGIT antibody to the animal as described herein, wherein the animal has a tumor; and determining the inhibitory effects of the anti-TIGIT antibody to the tumor. The inhibitor effects that can be determined include, e.g., a decrease of tumor size or tumor volume, a decrease of tumor growth, a reduction of the increase rate of tumor volume in a subject (e.g., as compared to the rate of increase in tumor volume in the same subject prior to treatment or in another subject without such treatment), a decrease in the risk of developing a metastasis or the risk of developing one or more additional metastasis, an increase of survival rate, and an increase of life expectancy, etc. The tumor volume in the subject can be determined by various methods, e.g., as determined by direct measurement, MRI or CT.

In some embodiments, the tumor comprises one or more tumor cells that express TIGIT ligands. In some embodiments, the tumor comprises one or more cancer cells (e.g., human or mouse cancer cells) that are injected into the animal. In some embodiments, the anti-TIGIT antibody can increase immune response.

In some embodiments, the genetically modified animals can be used for determining whether an anti-TIGIT antibody is a TIGIT agonist or antagonist. In some embodiments, the methods as described herein are also designed to determine the effects of the agent (e.g., anti-TIGIT antibodies) on TIGIT, e.g., whether the agent can stimulate T cells or inhibit T cells, whether the agent can upregulate the immune response or downregulate immune response. In some embodiments, the genetically modified animals can be used for determining the effective dosage of a therapeutic agent for treating a disease in the subject, e.g., cancer.

The inhibitory effects on tumors can also be determined by methods known in the art, e.g., measuring the tumor volume in the animal, and/or determining tumor (volume) inhibition rate ($TGI_{TV}$). The tumor growth inhibition rate can be calculated using the formula $TGI_{TV}$ (%)=(1−TVt/TVc)×100, where TVt and TVc are the mean tumor volume (or weight) of treated and control groups.

In some embodiments, the anti-TIGIT antibody is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the anti-TIGIT antibody is designed for the treating melanoma, non-small cell lung carcinoma (NSCLC), small cell lung cancer (SCLC), bladder cancer, and/or prostate cancer (e.g., metastatic hormone-refractory prostate cancer). Anit-TIGIT antibodies are known in the art, and are described in, e.g., US 20160176963, WO 2016028656, and WO 2017053748, each of which is incorporated by reference in its entirety.

The present disclosure also relates to the use of the animal model generated through the method as described herein in the development of a product related to an immunization processes of human cells, the manufacturing of a human antibody, or the model system for a research in pharmacology, immunology, microbiology and medicine.

In some embodiments, the disclosure provides the use of the animal model generated through the method as described herein in the production and utilization of an animal experimental disease model of an immunization processes involving human cells, the study on a pathogen, or the development of a new diagnostic strategy and/or a therapeutic strategy.

The disclosure also relates to the use of the animal model generated through the method mentioned above in the screening, verifying, evaluating or studying the TIGIT gene function, human TIGIT antibodies, drugs for human TIGIT targeting sites, the drugs or efficacies for human TIGIT targeting sites, the drugs for immune-related diseases and antitumor drugs.

Genetically Modified Animal Model with Two or More Human or Chimeric Genes

The present disclosure further relates to methods for genetically modified animal model with two or more human or chimeric genes. The animal can comprise a human or chimeric TIGIT gene and a sequence encoding an additional human or chimeric protein.

In some embodiments, the additional human or chimeric protein can be programmed cell death protein 1 (PD-1), cytotoxic T-lymphocyte-associated protein 4 (CTLA-4), Lymphocyte Activating 3 (LAG-3), T-Cell Immunoglobulin And Mucin Domain-Containing Protein 3 (TIM-3), Programmed Cell Death 1 Ligand 1 (PD-L1), TNF Receptor Superfamily Member 9 (4-1BB), CD27, CD28, CD47, OX40, CD27, Glucocorticoid-Induced TNFR-Related Protein (GITR), or B And T Lymphocyte Associated (BTLA).

The methods of generating genetically modified animal model with two or more human or chimeric genes (e.g., humanized genes) can include the following steps:

(a) using the methods of introducing human TIGIT gene or chimeric TIGIT gene as described herein to obtain a genetically modified non-human animal;

(b) mating the genetically modified non-human animal with another genetically modified non-human animal, and then screening the progeny to obtain a genetically modified non-human animal with two or more human or chimeric genes.

In some embodiments, in step (b) of the method, the genetically modified animal can be mated with a genetically modified non-human animal with human or chimeric PD-1, CTLA-4, LAG-3, TIM-3, PD-L1, 4-1BB, CD27, CD28, CD47, OX40, CD27, GITR, or BTLA.

In some embodiments, the TIGIT humanization is directly performed on a genetically modified animal having a human or chimeric PD-1, CTLA-4, LAG-3, TIM-3, PD-L1, 4-1BB, CD27, CD28, CD47, OX40, CD27, GITR, or BTLA gene.

As these proteins may involve different mechanisms, a combination therapy that targets two or more of these proteins thereof may be a more effective treatment. In fact, many related clinical trials are in progress and have shown a good effect. The genetically modified animal model with two or more human or humanized genes can be used for determining effectiveness of a combination therapy that targets two or more of these proteins, e.g., an anti-TIGIT antibody and an additional therapeutic agent for the treatment of cancer. The methods include administering the anti-TIGIT antibody and the additional therapeutic agent to the animals of any of the embodiments described above, wherein the animal has a tumor; and determining the inhibitory effects of the combined treatment to the tumor.

In some embodiments, the animal further comprises a sequence encoding a human or humanized programmed cell death protein 1 (PD-1). In some embodiments, the additional therapeutic agent is an anti-PD-1 antibody (e.g., nivolumab, pembrolizumab, avelumab, durvalumab, atezolizumab). In some embodiments, the tumor comprises one or more tumor cells that express CD155, CD112, CD80, CD86, PD-L1 or PD-L2.

In some embodiments, the combination treatment is designed for treating various cancer as described herein, e.g., melanoma, non-small cell lung carcinoma (NSCLC), small cell lung cancer (SCLC), bladder cancer, prostate cancer (e.g., metastatic hormone-refractory prostate cancer), colorectal cancer, gastric cancer, and/or neuroblastoma.

In some embodiments, the methods described herein can be used to evaluate the combination treatment with some other methods. The methods of treating a cancer that can be used alone or in combination with methods described herein, include, e.g., treating the subject with chemotherapy, e.g., campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verampil, podophyllotoxin, tamoxifen, taxol, transplatinum, 5-flurouracil, vincristin, vinblastin, and/or methotrexate. Alternatively or in addition, the methods can include performing surgery on the subject to remove at least a portion of the cancer, e.g., to remove a portion of or all of a tumor(s), from the patient.

EXAMPLES

The invention is further described in the following examples, which do not limit the scope of the invention described in the claims.

Materials and Methods

The following materials were used in the following examples.

Ambion™ in vitro transcription kit was purchased from Ambion.Catalog number is AM1354.

*E. coli* TOP10 competent cells were purchased from the Tiangen Biotech (Beijing) Co. Catalog number is CB104-02.

XbaI, XhoI, HindIII, ScaI, BamHI, BglII, BbsI, MfeI, EcoNI were purchased from NEB. Catalog numbers are R0145M, R0146M, R3104M, R3122M, R0136M, R0144M, R0539S, R0589S, R3101M.

Kanamycin was purchased from Amresco.Catalog number is 0408.

Cas9 mRNA was obtained from SIGMA.Catalog number is CAS9MRNA-1EA.

AIO kit was obtained from Beijing Biocytogen Co., Ltd. Catalog number is BCG-DX-004.

UCA kit was obtained from Beijing Biocytogen Co., Ltd. Catalog number is BCG-DX-001.

C57BL/6 mice were purchased from the China Food and Drugs Research Institute National Rodent Experimental Animal Center.

Mouse colon cancer cell line MC38 was purchased from Shanghai Enzyme Research Biotechnology Co., Ltd.

Mouse CD3 antibody was obtained from BD.Catalog number is 563123.

mPD-1 Ab was obtained from BIO X CELL. Catalog number is BE0146.

mTcRβ PerCP was obtained from Biolegend.Catalog number is 109228.

mPD-1_PE was obtained from Biolegend.Catalog number is 109104.

hTIGIT APC was obtained from eBioscience. Catalog number is 17-9500-42.

mTIGIT PE was obtained from eBioscience.Catalog number is 12-9501-82.

hPD-1 FITC was obtained from Biolegend.Catalog number is 329904.

Example 1: Construction of pT7-B2-6 and pT7-B2-10

The target sequence determines the targeting specificity of small guide RNA (sgRNA) and the efficiency of Cas9 cleavage at the target gene. Therefore, target sequence selection is important for sgRNA vector construction.

The 5'-terminal targeting sites (sgRNA1 to sgRNA8) and the 3'-terminal targeting sites (sgRNA9 to sgRNA17) were designed and synthesized. The targeting site sequence on TIGIT of each sgRNA is as follows:

```
sgRNA-1 targeting sequence (SEQ ID NO: 1):
5'-ctgaagtgacccaagtcgactgg-3' sgRNA-2 targeting sequence (SEQ ID NO: 2):
5'-ctgctgcttccagtcgacttggg-3' sgRNA-3 targeting sequence (SEQ ID NO: 3):
5'-ggccatttatagtgttgacctgg-3' sgRNA-4 targeting sequence (SEQ ID NO: 4):
5'-ccccaggtcaacactataaatgg-3' sgRNA-5 targeting sequence (SEQ ID NO: 5):
5'-caggcacgatagatacaaagagg-3' sgRNA-6 targeting sequence (SEQ ID NO: 6):
5'-tgtatctatcgtgcctgctgtgg-3' sgRNA-7 targeting sequence (SEQ ID NO: 7):
5'-ccaagtcgactggaagcagcagg-3' sgRNA-8 targeting sequence (SEQ ID NO: 8):
5'-ggtcacttcagctgtgtcagagg-3' sgRNA-9 targeting sequence (SEQ ID NO: 9):
5'-cccaccaggatacgtatgatagg-3' sgRNA-10 targeting sequence (SEQ ID NO: 10):
5'-tgtacctatcatacgtatcctgg-3' sgRNA-11 targeting sequence (SEQ ID NO: 11):
5'-cctatcatacgtatcctggtggg-3' sgRNA-12 targeting sequence (SEQ ID NO: 12):
5'-ttcagtgatcgggtggtcccagg-3' sgRNA-13 targeting sequence (SEQ ID NO: 13):
5'-atcctggtgggatttacaagggg-3' sgRNA-14 targeting sequence (SEQ ID NO: 14):
5'-ctccccttgtaaatcccaccagg-3' sgRNA-15 targeting sequence (SEQ ID NO: 15):
5'-caaggggagaatattcctgaagg-3' sgRNA-16 targeting sequence (SEQ ID NO: 16):
5'-tgtcattcattgtcagagactgg-3' sgRNA-17 targeting sequence (SEQ ID NO: 17):
5'-ctgagctttcttggaccttcagg-3'
```

Figure 1:
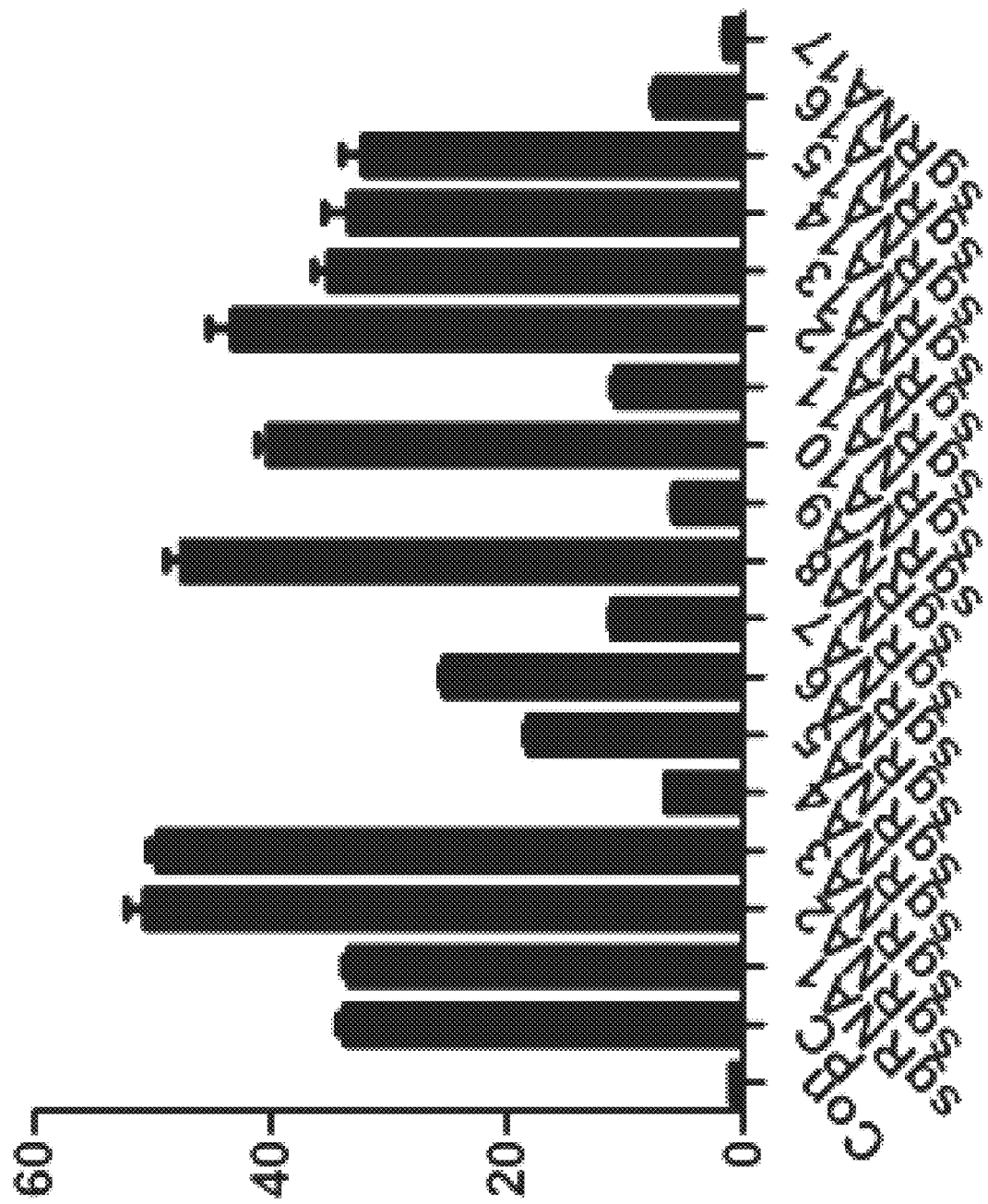
FIG. 1 is a graph showing the sgRNA activity test results (Con is a negative control; and PC is a positive control).

The UCA kit was used to detect the activities of sgRNAs (FIG. 1). The results show that the guide sgRNAs have different activities. Two of them (sgRNA6 and sgRNA10) were selected for follow-up experiments. TAGG was added to the 5' end to obtain a forward oligonucleotide sequence, and its complementary strand was added with AAAC to obtain a reverse oligonucleotide sequence. After annealing, they were respectively digested by restriction enzyme (BbsI) and ligated to pT7-sgRNA plasmid to obtain the expression vectors pT7-B2-6 and pT7-B2-10.

TABLE 3 sgRNA6 and sgRNA10 sequences

| sgRNA6 sequences | | |
|---|---|---|
| SEQ ID NO: 18 | | Upstream:<br>5'-TATCTATCGTG<br>CCTGCTG-3' |
| SEQ ID NO: 19 (adding TAGG to obtain a forward oligonucleotide sequence) | | Upstream:<br>5'-TAGGTATCTAT<br>CGTGCCTGCTG-3' |
| SEQ ID NO: 20 | | Downstream:<br>5'-CAGCAGGCACG<br>ATAGATA-3' |
| SEQ ID NO: 21 (complementary strand was added with AAAC to obtain a reverse oligonucleotide sequence) | | Downstream:<br>5'-AAACCAGCAGG<br>CACGATAGATA-3' |
| sgRNA10 sequences | | |
| SEQ ID NO: 22 | | Upstream:<br>5'-TACCTATCATA<br>CGTATCC-3' |
| SEQ ID NO: 23 (adding TAGG to obtain a forward oligonucleotide sequence) | | Upstream:<br>5'-TAGGTACCTAT<br>CATACGTATCC-3' |
| SEQ ID NO: 24 | | Downstream:<br>5'-GGATACGTATG<br>ATAGGTA-3' |
| SEQ ID NO: 25 (complementary strand was added with AAAC to obtain a reverse oligonucleotide sequence) | | Downstream:<br>5'-AAACGGATACG<br>TATGATAGGTA-3' |

TABLE 4

| The ligation reaction conditions | |
|---|---|
| Double stranded fragment | 1 μL (0.5 μM) |
| pT7-sgRNA vector | 1 μL (10 ng) |
| T4 DNA Ligase | 1 μL (5U) |
| 10×T4 DNA Ligase buffer | 1 μL |
| 50% PEG4000 | 1 μL |
| H₂O | Add to to 10 μL |

Reaction Conditions:

The ligation reaction was carried out at room temperature for 10 to 30 min. The ligation product was then transferred to 30 μL of TOP10 competent cells. The cells were then plated on a petri dish with Kanamycin, and then cultured at 37° C. for at least 12 hours and then two clones were selected and added to LB medium with Kanamycin (5 ml), and then cultured at 37° C. at 250 rpm for at least 12 hours.

Randomly selected clones were sequenced, so as to verify their sequences. The correct expression vectors pT7-B2-6 and pT7-B2-10 were selected for subsequent experiments.
Source of pT7-sgRNA Plasmid pT7-sgRNA vector map is shown in FIG. 2. The plasmid backbone was obtained from Takara (Catalog No. 3299). The DNA fragment containing T7 promoter and sgRNA scaffold was synthesized by a plasmid synthesis company, and linked to the backbone vector by restriction enzyme digestion (EcoRI and BamHI) and ligation. The target plasmid was confirmed by the sequencing results.
The DNA fragment containing the T7 promoter and sgRNA scaffold:

(SEQ ID NO: 26)
gaattctaatacgactcactatagggggtcttcgagaagacctgtt ttagagctagaaatagcaagttaaaataaggctagtccgttatcaa cttgaaaaagtggcaccgagtcggtgcttttaaaggatcc

Example 2. Construction of pClon-4G-TIGIT Vector

Figure 4:
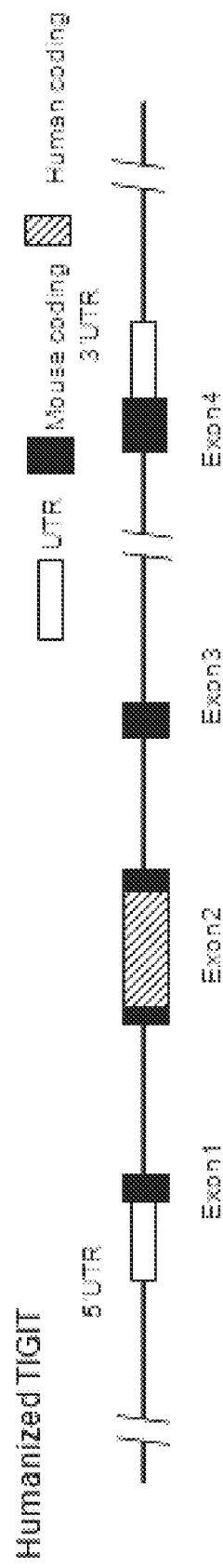
FIG. 4 is a schematic diagram showing humanized TIGIT mouse gene map.

A partial coding sequence of the TIGIT gene (Gene ID: 100043314) exon 2 (based on the transcript of NCBI accession number NM_001146325.1→NP_001139797.1, whose mRNA sequence is shown in SEQ ID NO: 27, and the corresponding protein sequence is shown in SEQ ID NO: 28) was replaced with a corresponding coding sequence of human homologous TIGIT gene (Gene ID: 201633) (based on the transcript of NCBI accession number NM_173799.3→NP_776160.2, whose mRNA sequence was shown in SEQ ID NO: 29, and the corresponding protein sequence is shown in SEQ ID NO: 30). The comparison between the mouse TIGIT and human TIGIT is shown in FIG. 3, and the finally obtained humanized TIGIT gene is shown in FIG. 4. The humanized mouse TIGIT gene DNA sequence (chimeric TIGIT gene DNA) is shown in SEQ ID NO: 31.

CCTCACCCATAGGAGCCACA*ACAGGCACAATTGAAACAACGGGGAA*

*CATTTCTGCAGAGAAAGGTGGCTCTATCATCTTACAATGTCACCTC*

*TCCTCCACCACGGCACAAGTGACCCAGGTCAACTGGGAGCAGCAGG*

*ACCAGCTTCTGGCCATTTGTAATGCTGACTTGGGGTGGCACATCTC*

*CCCATCCTTCAAGGATCGAGTGGCCCCAGGTCCCGGCCTGGGCCTC*

*ACCCTCCAGTCGCTGACCGTGAACGATACAGGGGAGTACTTCTGCA*

*TCTATCACACCTACCCTGATGGGACGTACACTGGGAGAATCTTCCT*

*GGAGGTCCTA*GAAAGCTCAGGTATGTCCTT

SEQ ID NO: 31 lists only the portion of DNA sequence involved in the modification, wherein the italicized underlined region is the human TIGIT gene sequence fragment.

The coding region sequence, mRNA sequence and the encoded protein sequence thereof of the modified human TIGIT are respectively shown in SEQ ID NO: 32, SEQ ID NO: 33 and SEQ ID NO: 34.

A targeting strategy involving a vector comprising the 5' end homologous arm, human TIGIT gene fragment, 3' homologous arm as shown in FIG. 5 is also developed. The process is as follows:

(1). Design upstream primers of homologous recombination fragments, and downstream primers matching therewith, as well as other related sequences. Specifically:

5' end homologous arm (SEQ ID NO: 35), nucleotide sequence of the positions from 43662298 to 43663801 of the NCBI accession number NC_000082.6 as follows:

CTGGGTTAGGGACTCTGACTGGACAGCTGTTCAAGAGGGAAGCTGG

GGAATAGACTAAGATTGGGAGCCAAGAAATCTCCTGGAAACCCATT

TCTCTCCTGCTCCATTTTCTTTTCTGTTTCTGAGGAACTCCTAGAA

CAATGTTCCAGTTAGTTCTCTGTTGGTCAGAAATACCTGCTTCTCA

GATTTTCATAGTCTACCACTAATATGAGAGACTAAATTCTGTTGTT

-continued
TCTATTCTATTACAAATTGTAGATAAACATTTCTGAGGGAAGGAAA

CAAAATATTTAGAGACTATACTACAAATTAGTTTAAAGGCTGAACT

TATAAGACTGAAGGTAGAGAGGAGCCAAGGTGGGGCAGGCTGGTAG

GTAGCAAAGAAGTTGGCTTCATCTAGGAGAAGGCCTTTCTTCCCCT

CTTACCTCTCCTCTACTGTCTTCCCTTCCTCTCCCCTCCCCTTCCT

TCTTCTCCCTTCTTCCCCTCCCCTTCCCTCCCCTCCCCTCCCCTCT

CCTCCCCTCCCCTCCCCTCCCCTCTCCTCCCCTCCCCTCCTATTTT

CTATGTTTCCCTCCCCTTCTCTTCCCTTCCATTACTTCTCCTTTCC

CTTCTTTCCCTCTTTCTCATTGTCCTCTCTTCCCCTTCCCTCTCTC

TTTTGCTTTAGTTTGTTTCTTTGACAGATACATGGTCTTTCTATGT

TTCCAAGGCTGGTCTGGAATGCACTATGATCCTCCTGCCTCATCCT

CCCATGTACTTGGATTAAAAATATATGCTGCTACTTCTGGCTGAGA

AGTAGATTCAAGTTTCCTTTCTCTGTGTTCTCTCTCTCTCTCTCTC

TCTCTCTCTCTCTCTCTCTCTCTCTCATTTTCCTGACATCCCAA

ATGCCAATCAAATAGCCCAGTTCTATTTTCAAAACATAGGGCTAGA

CACAAGGCTAGACTGCTGGAACCTAGAGAGAAGTACAAGATATGTT

GGTGTCGGGCTGATAGTCTAAGTGGGAAAGTTAAATAAGTTCATTG

AAAGCAATCAGCCACCTAGCCAGGAAGCCGAGCGGAACATCCTGAG

CGGACAAAGTGCTAGAAGCCTTGTAGTAAGAAGCCAGACATCTAAT

AAGACAACATTTAATAATACATCGCATGCAGGGGAAAAGGAAGGGC

TTAAAGCTAGGGTCCTCAGGTAAGGAGGAAGCACAGCTCTGACTGA

TGGGTGAGGATGAGGCAGGTTGGCAGGAGCAAGCTTCAGAAGCAGC

CATGGGGAGCAGGATGGGAACAGAGTCCATGGGAAAGGGACCATGG

CTGGGGCTTCAGGCCTCGAGTGACAGGCAGAGGAAGAAAAACTCTG

GAAATCAATGATGGTCTCTATGGGGGGCACCAGGAGAGACTGCAGA

CTGTGGACATCTGTTCCTAGAGCCAGATCTGGACTCTGAACCCTCT

GGGATTCTTCAGGAAGGTTGAAGGGCAGCTGCTGGCCAGAGACTCA

CGTGTGCTTTTCCCTCACCCATAGGAGCCACA

Upstream primer (F):
(SEQ ID NO: 36)
5'-TTTAAGAAGGAGATATACATGGAATTCCTGGGTTAGGGACTCT

GACTGGACAG-3'

Downstream primer (R): R:
(SEQ ID NO: 37)
5'-TTTCAATTGTGCCTGTTGTGGCTCCTATGGGTGAGGGAAAAG

C-3'

(2). Design the primers and related sequences of the desired conversion region. The human DNA fragment is the nucleotide sequence from positions 114295553 to 114295864 of the NCBI accession number NC_000003.12:

(SEQ ID NO: 38)
ACAGGCACAATTGAAACAACGGGGAACATTTCTGCAGAGAAAGGTG

GCTCTATCATCTTACAATGTCACCTCTCCTCCACCACGGCACAAGT

GACCCAGGTCAACTGGGAGCAGCAGGACCAGCTTCTGGCCATTTGT

AATGCTGACTTGGGGTGGCACATCTCCCCATCCTTCAAGGATCGAG

TGGCCCCAGGTCCCGGCCTGGGCCTCACCCTCCAGTCGCTGACCGT

GAACGATACAGGGGAGTACTTCTGCATCTATCACACCTACCCTGAT

GGGACGTACACTGGGAGAATCTTCCTGGAGGTCCTA

Upstream primer: F:
(SEQ ID NO: 39)
5'-ACCCATAGGAGCCACAACAGGCACAATTGAAACAACGGGGA

AC-3'

Downstream primer: R:
(SEQ ID NO: 40)
5'-GACATACCTGAGCTTTCTAGGACCTCCAGGAAGATTCTCCC

AG-3'

(3). Design the upstream primers of the homologous recombination fragment and the downstream primers matching therewith, as well as other related sequences. Specifically:

3' homologous arm (SEQ ID NO: 41), which was the nucleotide sequence from positions 43660538-43661985 of the NCBI accession number NC_000082.6:

GAAAGCTCAGGTATGTCCTTTGAGGCAAGGTGGTAGTGAGCCACTT

TCTCTCACATAGGAAACACCACCCTGACACACTCTAGGAAGTAGAG

TGTCTCAATCTTGGAGCACTTTGAACTCATTAGAGGATCTTTCGGG

GCATAGTAAAGATAGAACAACTGAAAGTGATGAACGTAGAACCTTG

TGGGGGCAGAGCTAGGATCTGATACGTTCCAGAAACAACCAGCCGA

TTCCCATGCACAACCACAGATTTTGCATAGGAAATCCATCTTATCT

AAAATGAGGTGACTTGCAGATGAGGTCATACATGAAAGGTGCTCAT

TTAATGACTTAGTATCACTCATGCAAATTAGAATTAGCTCTTAACA

GAGGATGGCCTAGTCAGCCATCAATGGGAGGAGAGGCGGCCCTTGG

TCTTTCAAAGATCATATGCCCCAGTACAGGGGAATGCCAGGGCCAG

GAAGCGGGAGTGGGTGGGTTGGGGATCAGGGTAGGGGAGGGTATA

GGGGACTTTCAGGATAGCATTTGAAATGCAAATGAAGAAAATATAT

AATTAAAAAAAAAGAATTAGCTCTTAAGTTTGAGCTGATTTAAAAC

AGGCCACAGCAGGTGCTGAGTGAAAAAGTATAATAGTCACCCACCT

TTGCATGATGACTATTTGGAAGCTTCAAAGCTTCCAAATGCCCTCA

TAAATGATTATTCTTCTACAAACATGAGCCAATTTTACTGAGGAAA

GGGATTATGAAAATCGTATCTGAAAGATAGTTTAGCAAGGTAGTAA

AGTGCTCAGCCTCTAATGCCAGACATCATAGGTCCAAACCTTGCTG

ATGGATTAATTTGTCCAGTCAGTATGGCTATAAGATTTTATGAGCT

GCTAATGTGGGCTTGGATAACCTACTATAAGAAAAAGCCCTTAGCA

TGATGCCAGCCATATAGCAAGTGCCATGTTAGGTGTTGATCATTCC

CATCTGATTGATGGTTGTGGAAGCTAAGGCTTGGAATTGCTCAGGG

TGAGAAAGCTGATTTTAAATCAGATGTTCTGGCTCCATGGATCACC

ACACTCAGAGCTGCATACTATCAGTTATATTGGAGTTTAGGTTAAG

AACATATATGAATTGAAATTATGTTGGAGTTTAGGTTTCATGAGTT

TTAAGAATAAATATACTTTGAAACGATAAAAGTTTACCTTAATGTT

TCCTTTCAAACACTGCTTCCTGGCACCTGTGCAGTGTGCATGCTAT

GGTCTTCTATCCCTGTTCTTCCTGAGTGAGCCATGGCTATGACCAG

GAAGGGGTCAGCCTGGCCTATCATGTCTAAGTCCTCAGAGCAGGAG

GAGCATGCTGGGACTTTGGAGTTCCCAGGCATGGTCTTTGTCCTGA

GGGATCAGATACTGGAGTCTCCTTTCCTATGATCCCTTGTGTTCAG

GGATGTGGGACAGGCTTTTTCT

Upstream primer: F:
(SEQ ID NO: 42)
5'-TCTTCCTGGAGGTCCTAGAAAGCTCAGGTATGTCCTTTGAG

GC-3'

Downstream primer: R:
(SEQ ID NO: 43)
5'-TTGTTAGCAGCCGGATCTCAGGATCCAGAAAAAGCCTGTCCCA

CATCCCTG-3'

C57BL/6 mouse DNA is used as the template to carry out PCR amplification for the 5'-terminal homologous arm fragment (SEQ ID NO: 1) and the 3'-terminal homologous arm fragment (SEQ ID NO: 2) of exon 2. Human DNA is used as the template to carry out PCR amplification for the DNA fragment (SEQ ID NO: 3), and the AIO kit is used to ligate the fragments to the pClon-4G plasmid provided by the kit, so as to obtain the vector pClon-4G-TIGIT.

Example 3. Verification of Vector pClon-4G-TIGIT

Figure 6:
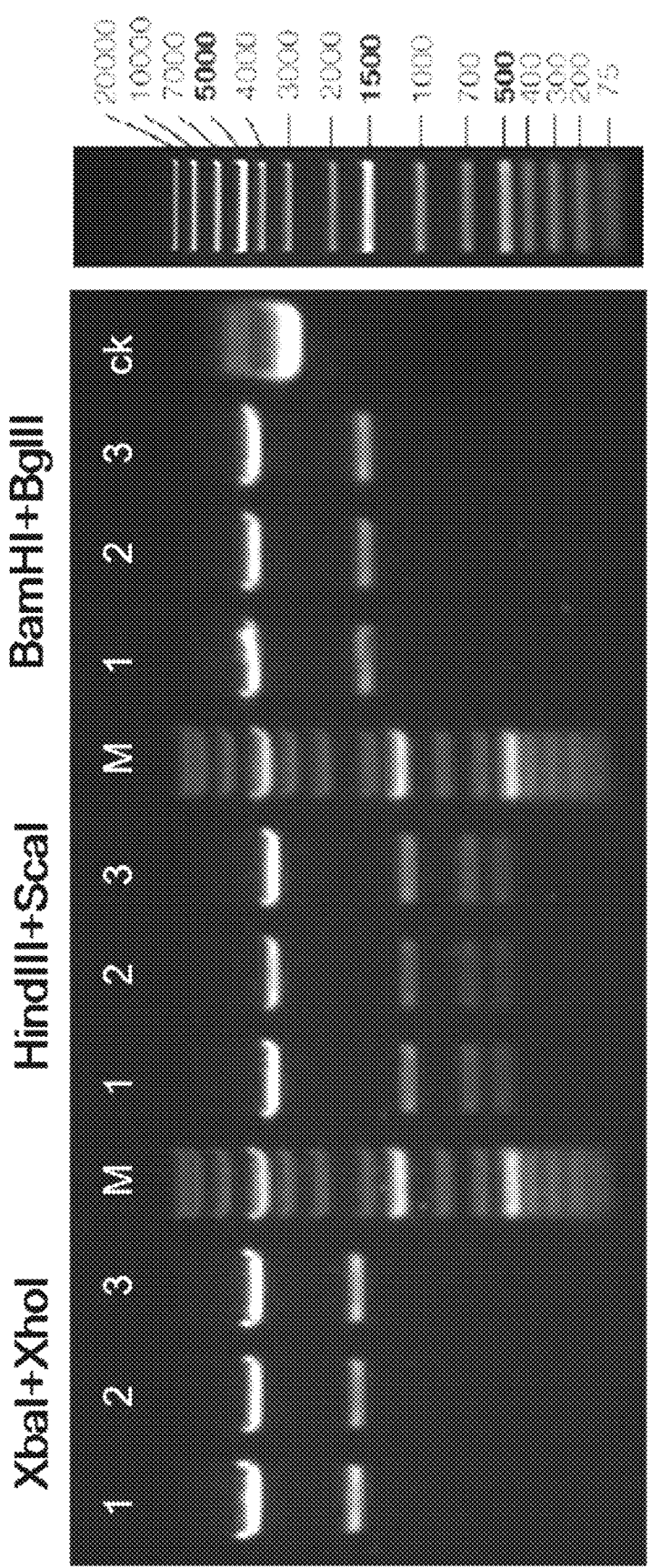
FIG. 6 shows pClon-4G-TIGIT plasmid digestion result (M is the Marker, ck is the undigested plasmid control).

Three pClon-4G-TIGIT clones were randomly selected and identified by three sets of enzymes. Among them, XbaI+XhoI should generate 4766 bp+2011 bp fragments, HindIII+ScaI should generate 4233 bp+1283 bp+729 bp+524 bp+8 bp fragments, BamHI+BglII should generate 4917 bp+1860 bp fragments. The results obtained were in line with the expectations (FIG. 6). The sequences of Plasmids 1 and 2 were verified by sequencing. Plasmid 1 was selected for subsequent experiments.

Example 4. Microinjection and Embryo Transfer

The pre-mixed in vitro transcription products of Cas9 mRNA, pClon-4G-TIGIT plasmid and pT7-B2-6, pT7-B2-10 plasmids were injected into the cytoplasm or nucleus of mouse fertilized eggs (C57BL/6 background) with a microinjection instrument (using Ambion in vitro transcription kit to carry out the transcription according to the method provided in the product instruction). The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected fertilized eggs were then transferred to a culture medium for a short time culture, and then was transplanted into the oviduct of the recipient mouse to produce the genetically modified humanized mice. The mice population was further expanded by cross-mating and self-mating to establish stable mouse lines. The humanized mouse obtained was named B-hTIGIT.

Example 5. Identification of Genetically Modified Humanized Mouse Model

1. Genotype Detection

PCR analysis was performed for mouse tail genomic DNA using 18 F0 generation mice. Primers were designed for exon 2 of TIGIT gene; the primers for PCR-1 were located on the left side of the 5' homologous arm, the primers for PCR-4 were located on the right side of the 3' homologous arm; in addition, the primers for PCR-2 and PCR-3 were located on the humanized fragment, which are shown below:

```
5' terminus primers:
PCR-1:
                                 (SEQ ID NO: 44)
5'-CAGAGACACCTAGCTTGGCACAGAC-3';

PCR-2:
                                 (SEQ ID NO: 45)
5'-GATTCTCCCAGTGTACGTCCCATCAG-3'

3' terminus primers:
PCR-3:
                                 (SEQ ID NO: 46)
5'-TACAATGTCACCTCTCCTCCACCAC-3';

PCR-4:
                                 (SEQ ID NO: 47)
5'-CAGTTGTGAGACCCTGGAAGGAGTG-3'
```

If the recombinant vector has the correct insertion, there should be only one PCR band. The length of the 5' terminus product should be 1999 bp, and the length of the 3' terminus product should be 1900 bp.

TABLE 5

| The PCR reaction system (20 μL) | |
| --- | --- |
| 10× buffer | 2 μL |
| dNTP (2 mM) | 2 μL |
| MgSO$_4$ (25 mM) | 0.8 μL |
| Upstream primer (10 μM) | 0.6 μL |
| Downstream primer (10 μM) | 0.6 μL |
| Mouse tail gDNA | 200 ng |
| KOD-Plus-(1 U/μL) | 0.6 μL |

TABLE 6

| The PCR reaction conditions | | |
| --- | --- | --- |
| Temperature | Time | Cycles |
| 94° C. | 5 min | 1 |
| 94° C. | 30 sec | 15 |
| 67° C.* | 30 sec | |
| 68° C. | 1 kb/min | |
| 94° C. | 30 sec | 25 |
| 56° C. | 30 sec | |
| 68° C. | 1 kb/min | |
| 68° C. | 10 min | 1 |
| 4° C. | 10 min | 1 |

(*each cycle has a temperature drop of 0.7° C.)

Figure 7A:
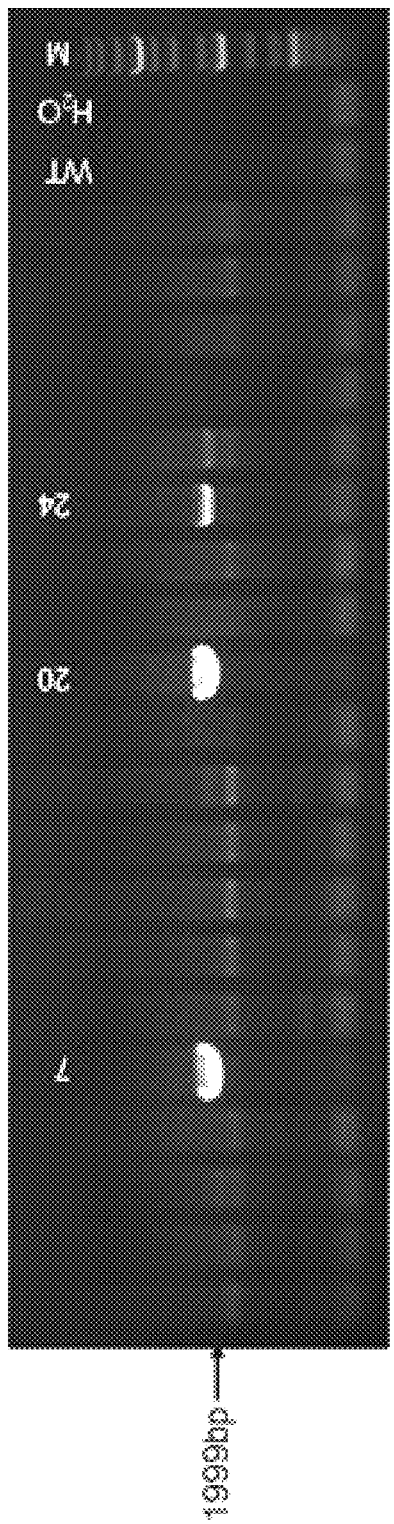
FIG. 7A shows PCR identification result (5' terminus) of samples from mouse tails (WT is wild type; M is Marker; Mice with No. 7, 20, and 24 are positive. Other mice (unlabeled) are negative).
Figure 7B:
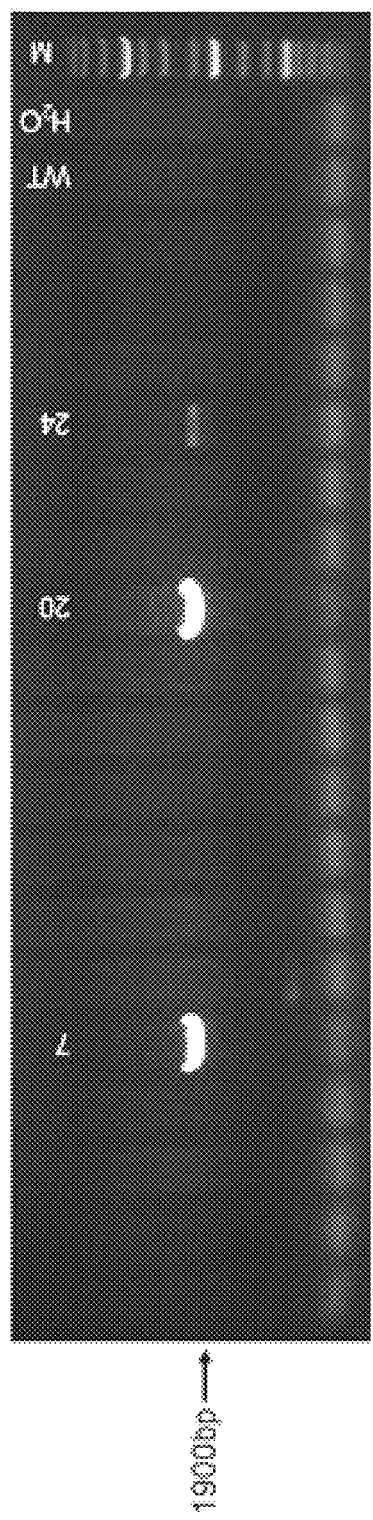
FIG. 7B shows PCR identification result (3' terminus) of samples from mouse tails (WT is wild type; M is Marker; Mice with No. 7, 20, and 24 are positive. Other mice (unlabeled) are negative).

Among the 18 mice, 3 of them were identified as positive mice. The identification results of the 3 mice are provided in FIGS. 7A-7B.

Figure 8A:
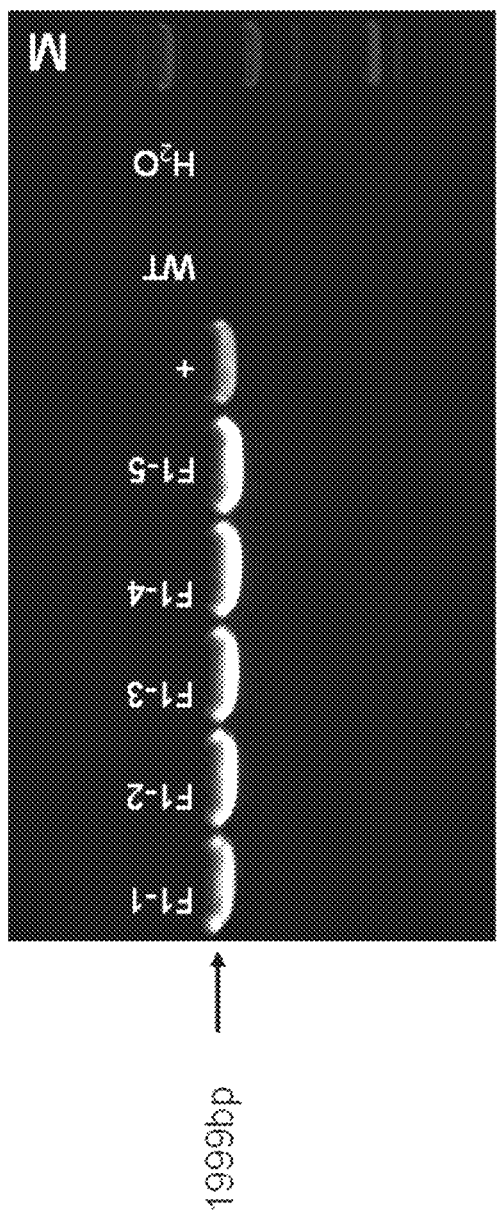
FIGS. 8A and 8B show mouse tail PCR identification result (WT is wild type, M is Marker, + is the positive control, F1-1 to F1-5 are the F1 generation B-hTIGIT positive mice).
Figure 8B:
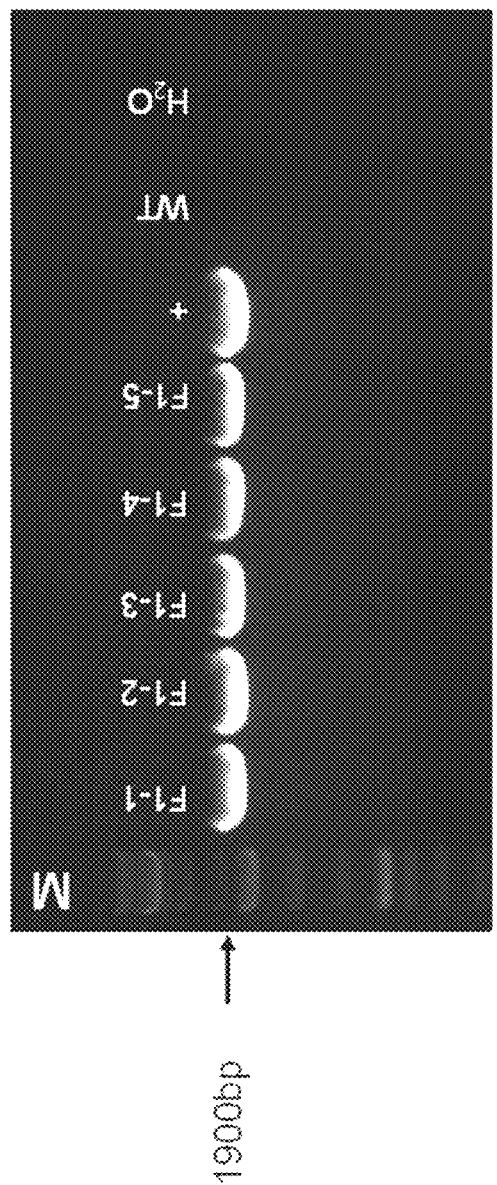

Furthermore, F1 generation mice were obtained by mating the F0 mice with wild type mice. PCR analysis was then performed on genomic DNA of F1 mice tails. PCR conditions and primers are the same with those used for F0 genotype detection. The results of PCR for F1 mice were shown in FIGS. 8A-8B, indicating that there were 5 positive F1 mice, and these mice are as follows: F1-1, F1-2, F1-3, F1-4, and F1-5.

These 5 mice were further examined by Southern blotting to determine whether they had a random insertion. The genomic DNA was extracted from the mouse tail, and MfeI and EcoNI were used to digest the genomic DNA, the digestion products were transferred to membrane and hybridized. The probes P1 and P2 were located respectively on the outside of the 5' homologous arm and the humanized fragment. The primers for probe synthesis are as follows:

```
P1-F (SEQ ID NO: 48):
5'-CTGGCTACCCAAGTAGTCAAT-3'

P1-R (SEQ ID NO: 49):
5'-CTGGTGTCTGTGCCAAGCTAG-3'

P2-F (SEQ ID NO: 50):
5'-CCCTTAGCATGATGCCAGCCAT-3'

P2-R (SEQ ID NO: 51):
5'-CATGCCTGGGAACTCCAAAGTCC-3'
```

The genetically engineered mice should have the 12.9 kb or 12.1 kb band with probe hybridization; whereas the wild type C56BL/6 mice would have the 16.9 kb or 12.1 kb band.

Figure 9:
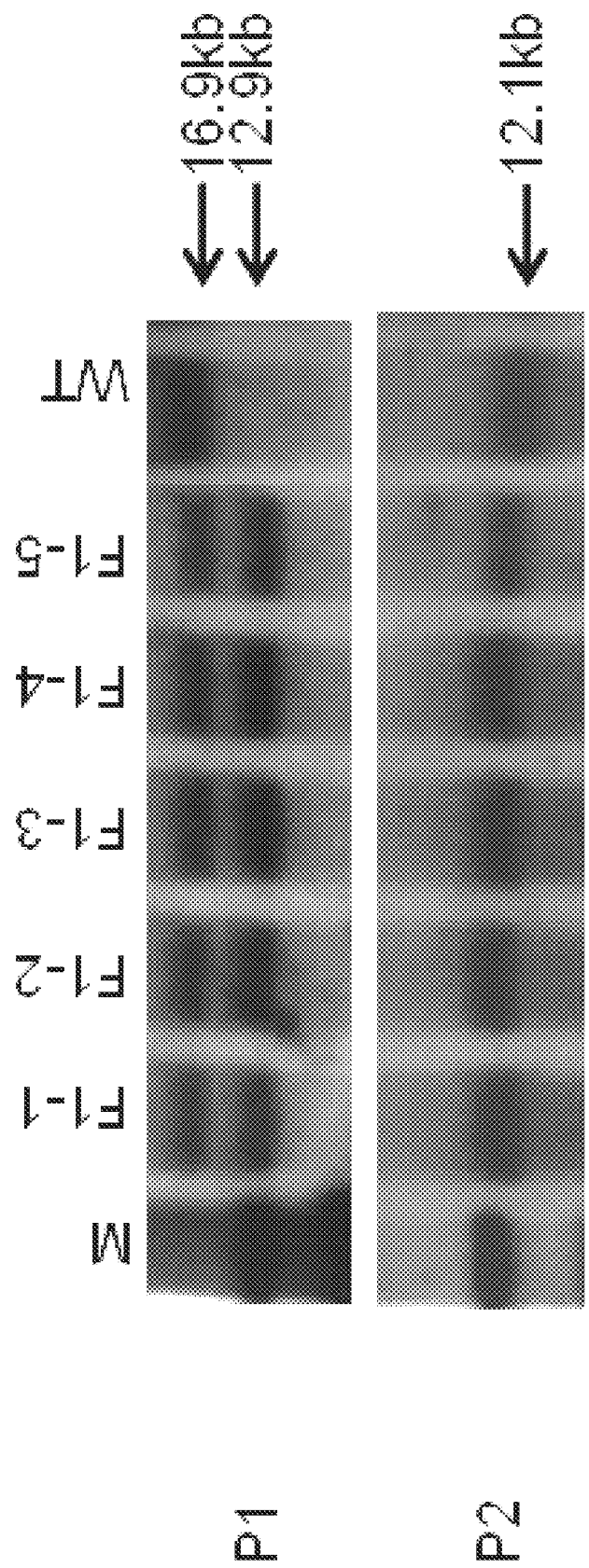
FIG. 9 shows Southern blot results for F1 generation mice (M is the marker, WT is wild type, F1-1 to F1-5 mice have no random insertion).

The results showed that the bands were consistent with the expected results. It was confirmed that the 5 mice were positive hybrids that did not have random insertions. Southern blot results are shown in FIG. 9.

It thus shows that this method can be used to construct B-hTIGIT humanized genetically engineered mice that have no random insertion.

2. Protein Identification

Figures 10A, 10B, 10C, 10D, 10E:
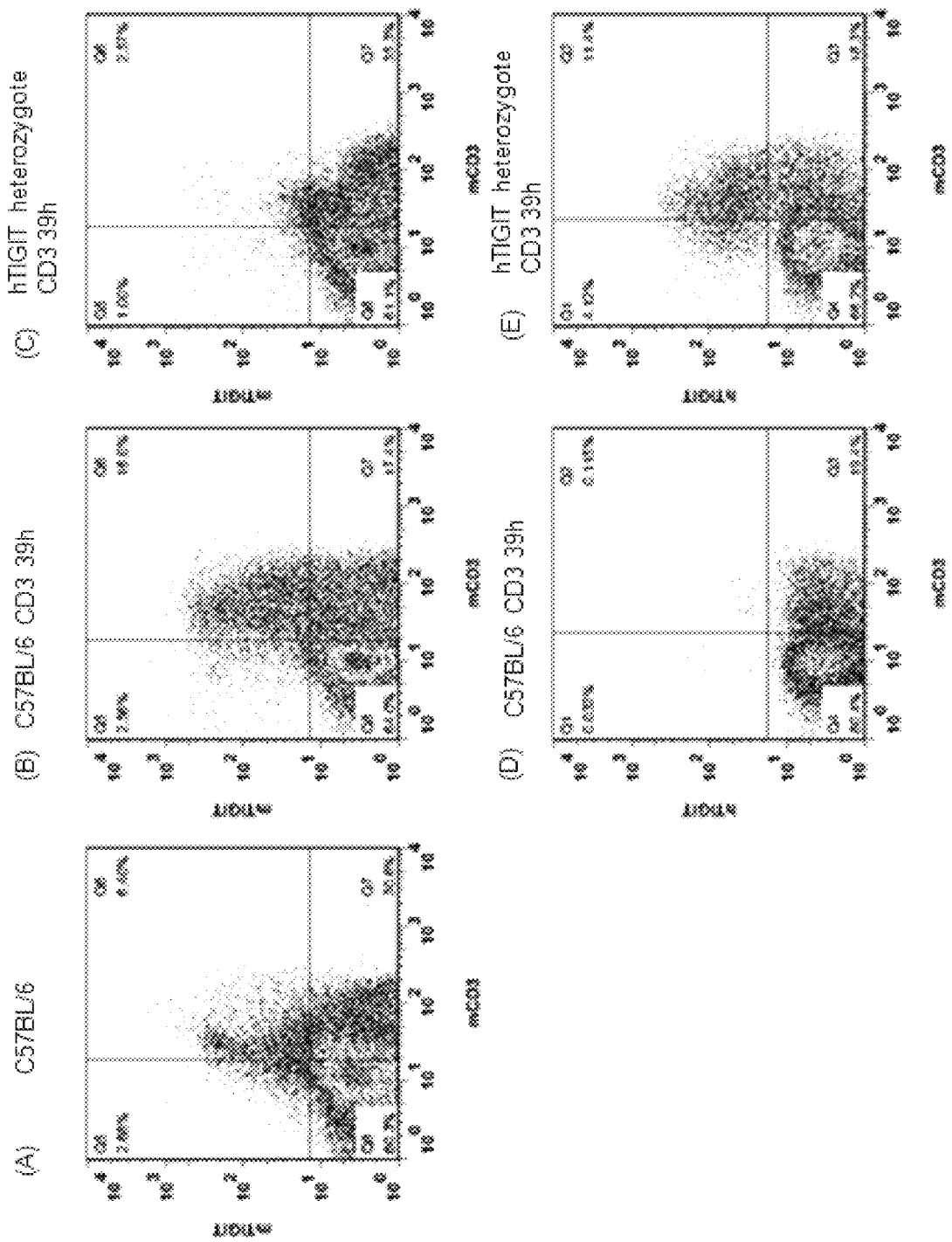
FIGS. 10A-10E are graphs showing flow cytometry analysis results for C57BL/6 mice and humanized TIGIT heterozygous mice. Anti-mouse CD3 antibody was used to stimulate their T cell activation in the spleen, and then anti-mouse (FIGS. 10B and 10C) and anti-human (FIGS. 10D and 10E) TIGIT antibodies with fluorescent labels were used for cell labeling. Compared with the control group (FIG. 10A), the cells with the expression of humanized TIGIT protein can be detected in the spleen of humanized TIGIT F1 heterozygous mice; whereas in the spleens of C57BL/6 mice, no cells expressing humanized TIGIT protein were detected.

One of the humanized heterozygous F1 mice identified by PCR was selected for the study. One wild type C57BL/6 mouse was used as the control. 15 μg of CD3 were injected intraperitoneally to the mice, and in 24 h 15 μg of CD3 were further injected intraperitoneally to the mice. The spleens were collected at the end of 39 h, and the spleen samples were grinded. The ground samples were then passed through 70 μm cell mesh, the filtered cell suspensions were centrifuged and the supernatants were discarded; the erythrocyte lysis solution was added for lysis of 5 min, and then PBS solution was added to neutralize the lysis reaction. The solution was centrifuged again and the supernatants were discarded. The cells were washed once with PBS. The antibody staining was performed for 30 to 45 min in darkness; and the cells were washed once again with PBS. Flow cytometry was carried out to detect protein expression. Flow cytometry analysis results (FIG. 10) show when compared with the C57BL/6 mice with or without the stimulation of CD3 antibody for T cell activation in spleen, the humanized mouse spleen has the cells of human TIGIT protein expression as detected by anti-human TIGIT antibody, while the spleen of the C57BL/6 control mice does not have detectable cells of human TIGIT protein expression. The foregoing results indicate that the TIGIT genetically modified humanized mouse is able to express human TIGIT protein, which can be detected by an anti-human antibody.

The B-hTIGIT humanized genetically engineered homozygous mice were obtained by mating the previously obtained F1 positive mice with each other. One B-hTIGIT mouse was selected, and two wild type C57BL/6 mouse were selected as a control. 7.5 μg of mouse CD3 antibody was injected intraperitoneally to the mice, and the spleens of the mice were collected after 24 h. The spleen samples were ground and then filtered through a 70 μm cell filter, the obtained cell suspensions were centrifuged and the resulting supernatants were discarded. The cell samples were added with erythrocyte lysis solution for lysis of 5 min, and then added PBS solution to neutralize the lysis reaction, centrifuged again and the supernatants were discarded, the cells were washed once with PBS. The obtained samples were used in FACS detection and RT-PCR detection.

Figure 11:
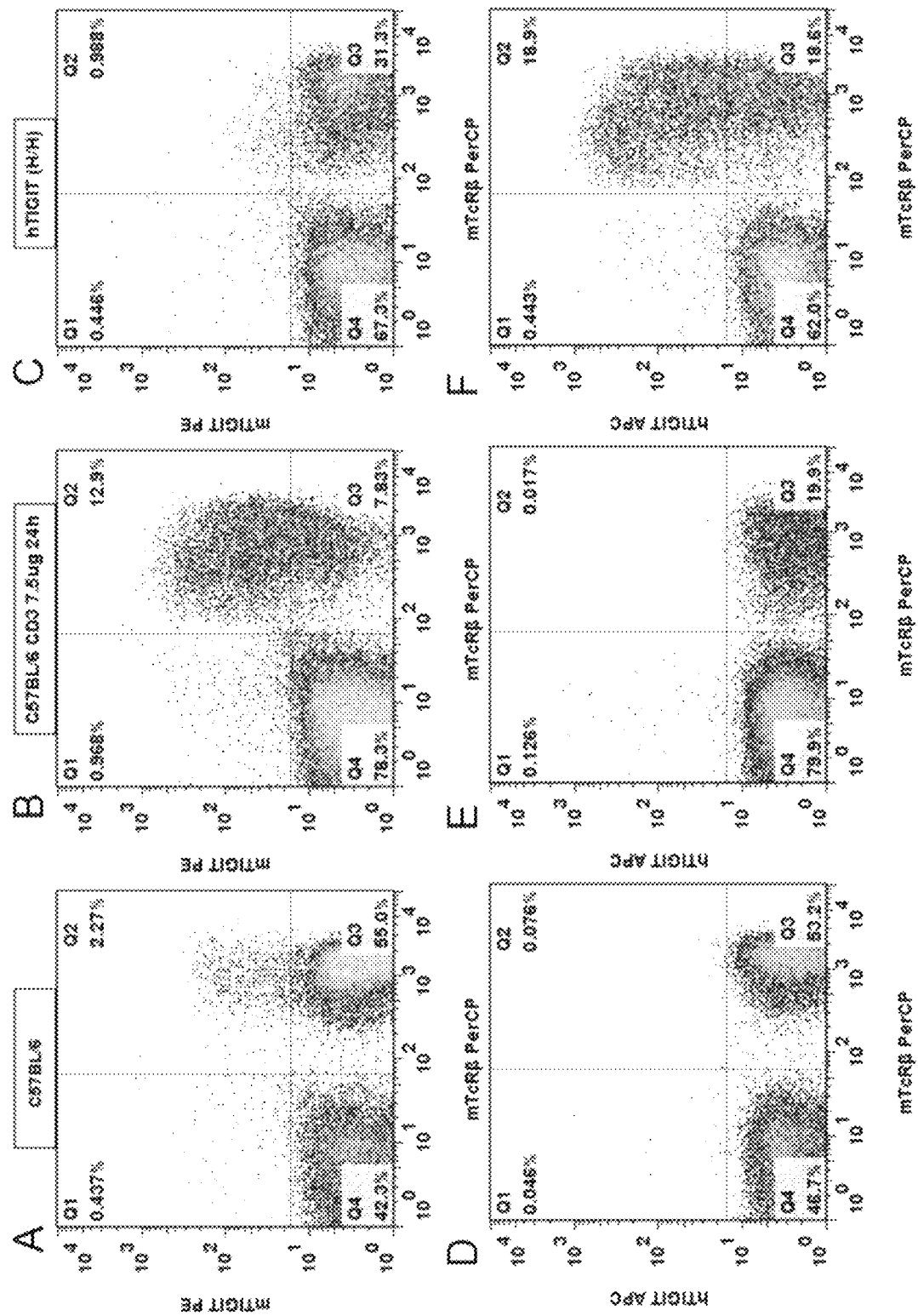
FIGS. 11A-11F are graphs showing flow cytometry analysis results for wild type C57BL/6 mouse and B-hTIGIT homozygous mouse. The mice were respectively stimulated by anti-mouse CD3 antibody to stimulate T cell activation in their spleens, and then anti-mouse TIGIT antibody mTIGIT PE (FIGS. 11A, 11B, 11C), anti-human TIGIT antibody hTIGIT APC (FIGS. 11D, 11E, 11F), and mouse T cell surface antibody mTcRβ were used for cell labeling. The cells with the expression of humanized TIGIT protein can be detected in the spleens of B-hTIGIT homozygous mouse (FIG. 11F); whereas in the spleen of C57BL/6 mouse, no cells expressing human TIGIT protein were detected (FIGS. 11D and 11E).

FACS detection: The T cells extracellular proteins were simultaneously stained with mouse TIGIT antibody mTIGIT PE and mouse T cell surface antibody mTcRβ, as well as human TIGIT antibody hTIGIT APC and mouse T cell surface antibody mTcRβ; the cells were then washed with PBS and then detected for protein expression by FACS detection. Flow cytometry analysis results are shown in FIG. 11, when compared with the C57BL/6 mice with or without the stimulation of CD3 antibody for T cell activation in spleen, the mouse TIGIT antibody is able to detect the cells expressing mouse TIGIT protein in the spleen samples from the C57BL/6 control mice; while the mouse TIGIT antibody is unable to detect the cells expressing mouse TIGIT protein in the spleen samples from B-hTIGIT homozygote. Moreover, the human TIGIT antibody is able to detect the cells expressing human TIGIT protein in the spleen samples from B-hTIGIT homozygote; while the human TIGIT antibody is unable to detect the cells expressing human TIGIT protein in the spleen samples from the C57BL/6 control mice.

RT-PCR detection: total RNA was extracted from the spleen cells of wild-type C57BL/6 mice and B-hTIGIT homozygotes, and cDNA were then obtained by reverse transcription using a reverse transcription kit.

```
Primers for mTIGIT RT-PCR:
mTIGIT RT-PCR F1:
                                  (SEQ ID NO: 52)
5'-tcctctgacacagctgaagtg-3',
and mTIGIT RT-PCR R1:
                                  (SEQ ID NO: 53)
5'-actctcccgtgtcattcatt-3'
were used to amplify mouse TIGIT fragment
of 175 bp.

Primers for hTIGIT RT-PCR:
hTIGIT RT-PCR F1:
                                  (SEQ ID NO: 54)
5'-gcacaattgaaacaacgggga-3',
and hTIGIT RT-PCR R1:
                                  (SEQ ID NO: 55)
5'-tgaaggatggggagatgtgc-3'
were used to amplify human TIGIT fragment
of 171 bp.
```

PCR reaction system is 20 μL, reaction conditions: 95° C., 5 min; (95° C., 30 sec; 60° C., 30 sec; 72° C., 30 sec, 35 cycles); 72° C., 10 min; and 4° C. GAPDH was used as an internal reference.

Figure 12:
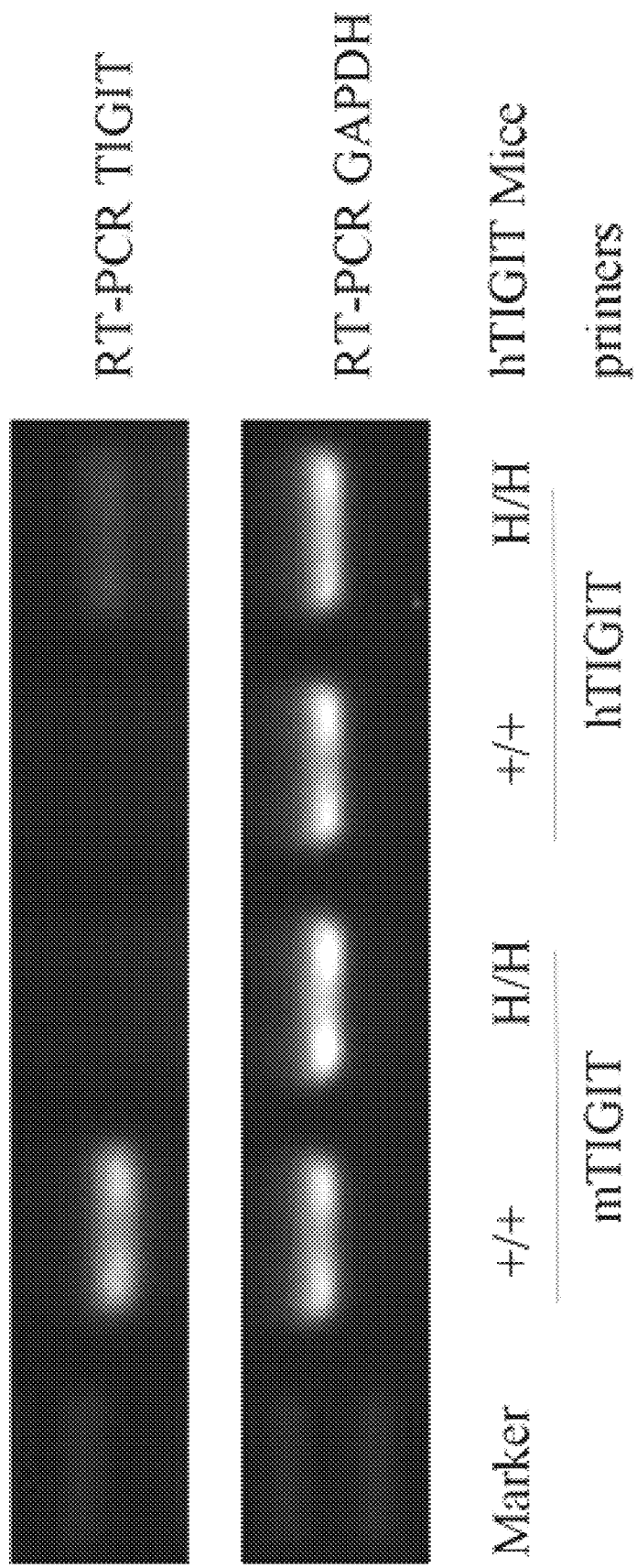
FIG. 12 shows RT-PCR detection results, wherein +/+ is wild type C57BL/6 mouse; H/H is B-hTIGIT homozygous mouse; and GAPDH is an internal control.

The results are shown in FIG. 12. The mRNA expression of mouse TIGIT could be detected in the activated cells of wild-type C57BL/6 mice; while the mRNA expression of human TIGIT could be detected in the activated cells of B-hTIGIT homozygous mice (FIG. 12B).

Example 6. Identification of Gene Knockout Mice

Since the cleavage of Cas9 results in DNA double strands break, and the homologous recombination repair may result in insertion/deletion mutations, it is possible to obtain TIGIT gene-disrupted gene knockout (exon 2 knock out) mouse while preparing the TIGIT gene humanized mouse. A pair of primers was thus designed. They are located on the left side of the 5' end target site, and to the right side of the 3' end target site, which are shown as follows:

```
                                  (SEQ ID NO: 56)
5'-TGACAGGCAGAGGAAGAAAAACTCTG-3'

(SEQ ID NO: 57)
5'-TGCAAAATCTGTGGTTGTGCATGGG-3'
```

Figure 13:
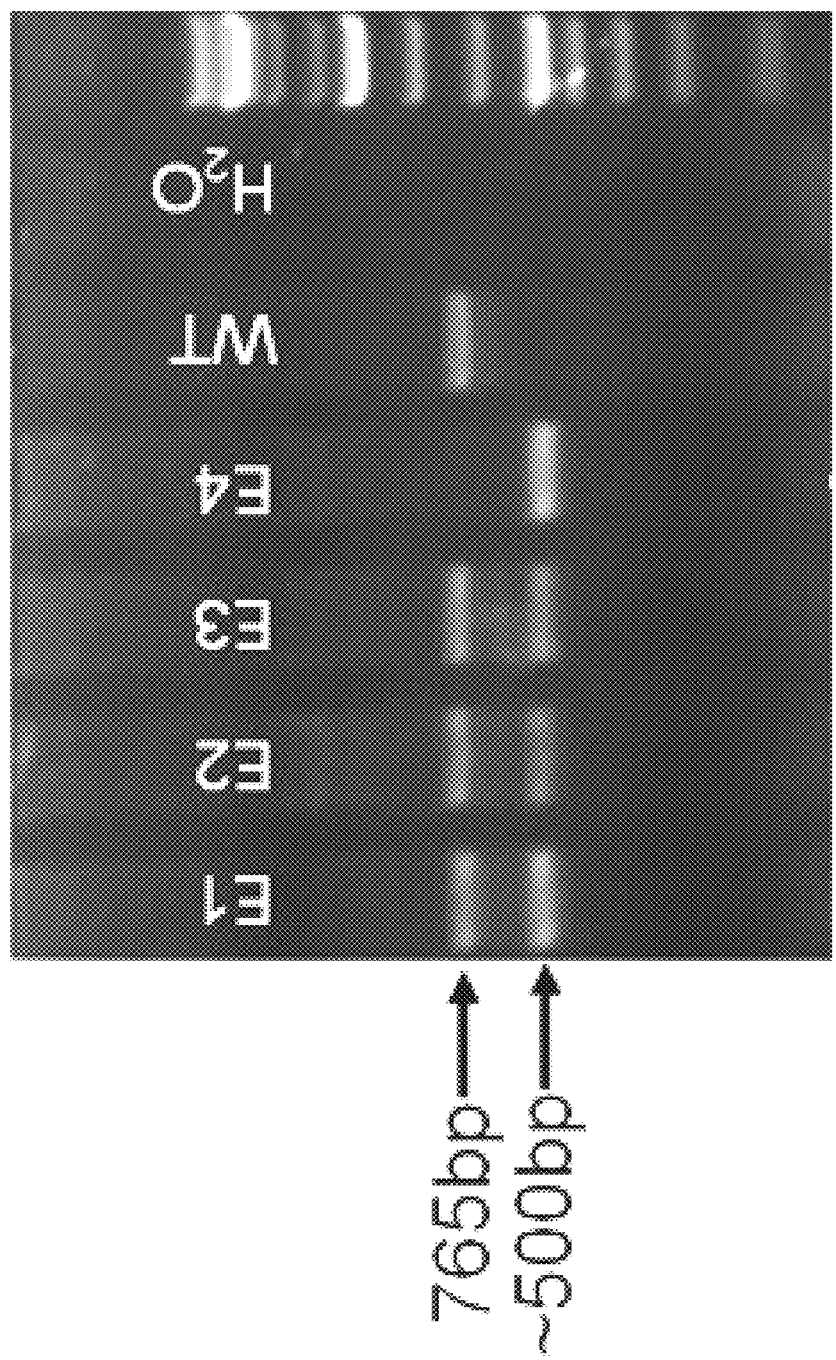
FIG. 13 shows PCR identification results for gene knock-out mice, wherein WT is wild type, the mice with no. E1, E2, E3 are heterozygous mice, while E4 may be a homozygous mouse.

The wild-type mice should have only one PCR band, and the product length should be 765 bp; the heterozygous mice should have another PCR band, and the product length should be about 500 bp; the homozygous mice should also have only one PCR band. The PCR reaction system and conditions were identical to those of Example 5, the obtained mice were identified as knockout mice, and the PCR results are shown in FIG. 13.

Example 7. Pharmacological Validation of B-hTIGIT Gene Humanized Animal Model

B-hTIGIT homozygous mice (4-6 weeks) were subcutaneously injected with mouse colon cancer cell MC38 ($5 \times 10^5$/100 μl PBS), and when the tumor volume grew to about 100 mm³, the mice were divided to a control group and a treatment group based on tumor size (n=5/group). The treatment group was randomly selected for anti-human TIGIT antibody B1 and anti-human TIGIT antibody B2 treatment (3 mg/kg); the control group was injected with an equal volume of blank solvent. The frequency of administration was once every 3 days. A total of 6 times of administrations were provided. The tumor volume was measured twice a week and the body weight of the mice was weighed as well. Euthanasia was performed when the tumor volume of the mouse reached 3000 mm³.

Figure 14:
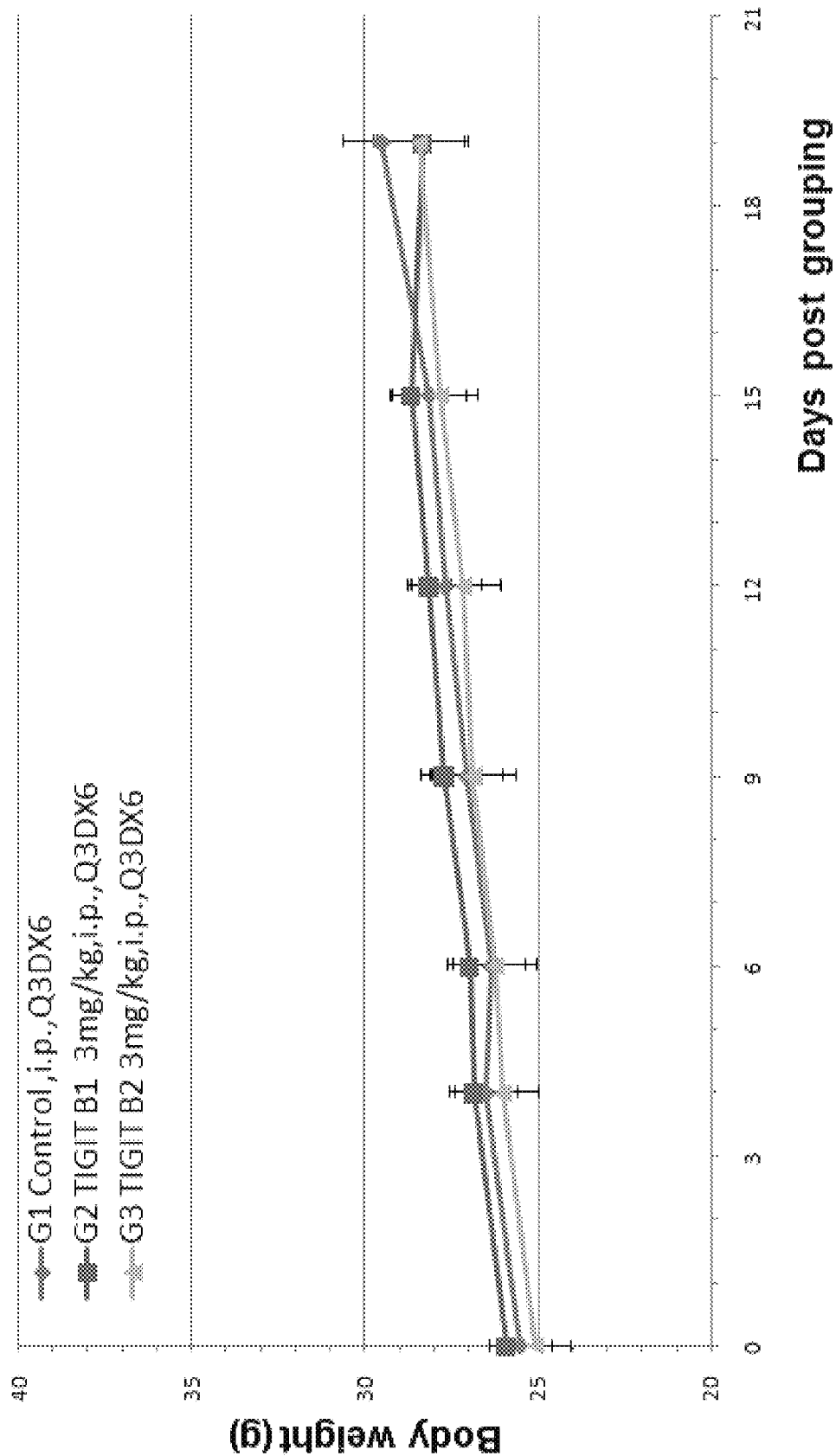
FIG. 14. Mouse colon cancer cells MC38 were injected into B-hTIGIT mice and antitumor efficacy studies were performed using human TIGIT antibodies TIGIT B1 and TIGIT B2 (3 mg/kg). There was no significant difference in mean weight gain between different groups.
Figure 15:
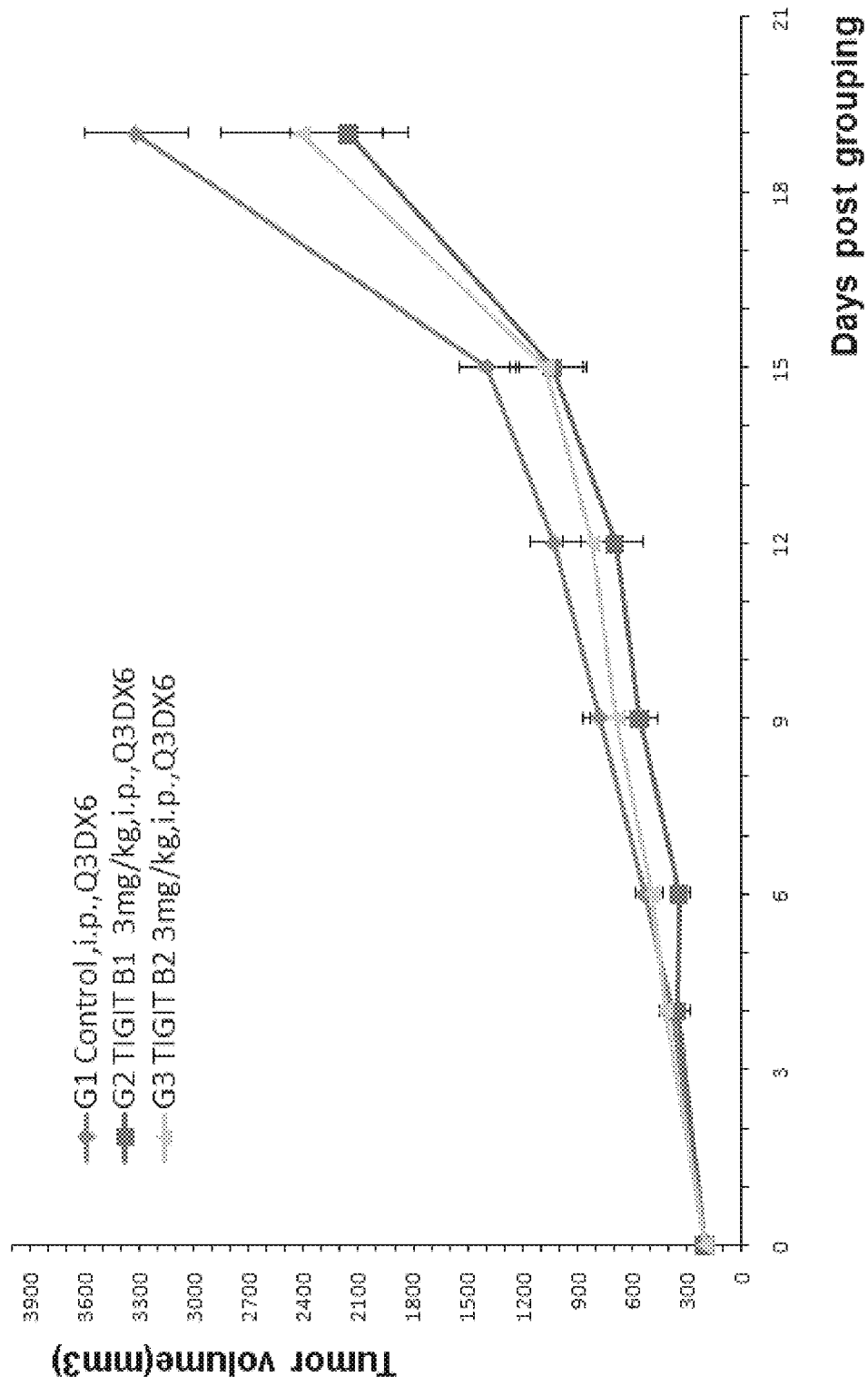
FIG. 15. Mouse colon cancer cells MC38 were injected into B-hTIGIT mice and antitumor efficacy studies were performed using human TIGIT antibodies TIGIT B1 and TIGIT B2 (3 mg/kg). The average volume of tumor in the G2 and G3 groups were significantly smaller than that in G1 control group.

Overall, the animals in each group were healthy, and the body weights of all the treatment and control group mice increased, and were not significantly different from each other (FIG. 14). The tumor in the control group continued growing during the experimental period; when compared with the control group mice, the tumor volumes in the treatment group were smaller (FIG. 15). It thus can be determined that the use of anti-TIGIT antibodies can inhibit the tumor growth in mice.

Table 5 shows results for this experiment, including the tumor volumes at the day of grouping, 15 days after the grouping, and at the end of the experiment (day 19), the survival rate of the mice, the Tumor Growth Inhibition value ($TGI_{TV}$), and the statistical differences (P value) in mouse body weights and tumor volume between the treatment and control groups.

At the end of the experiment (day 19), the body weight of each group increased and there was no significant difference between the groups (p>0.05), indicating that the animals tolerated TIGIT B1 and TIGIT B2 well. Concerning tumor volume, in the control group (G1), the average tumor volume was 3319±637 mm³. In the treatment groups, the average tumor volume was 2150±742 mm³ in G2, and 2413±987 mm³ in G3. The tumor volumes of all the treated mice were smaller than those in the control group, and the differences between the G2 group and the control group were statistically significant (p<0.5). The results show that both anti-human TIGIT antibody B1 and anti-human TIGIT antibody B2 have tumor inhibitor effects in B-hTIGIT mouse, and the inhibitor effects of anti-human TIGIT antibody B1 are better than anti-human TIGIT antibody B2, and they had no obvious toxic effects in mice.

Figure 16:
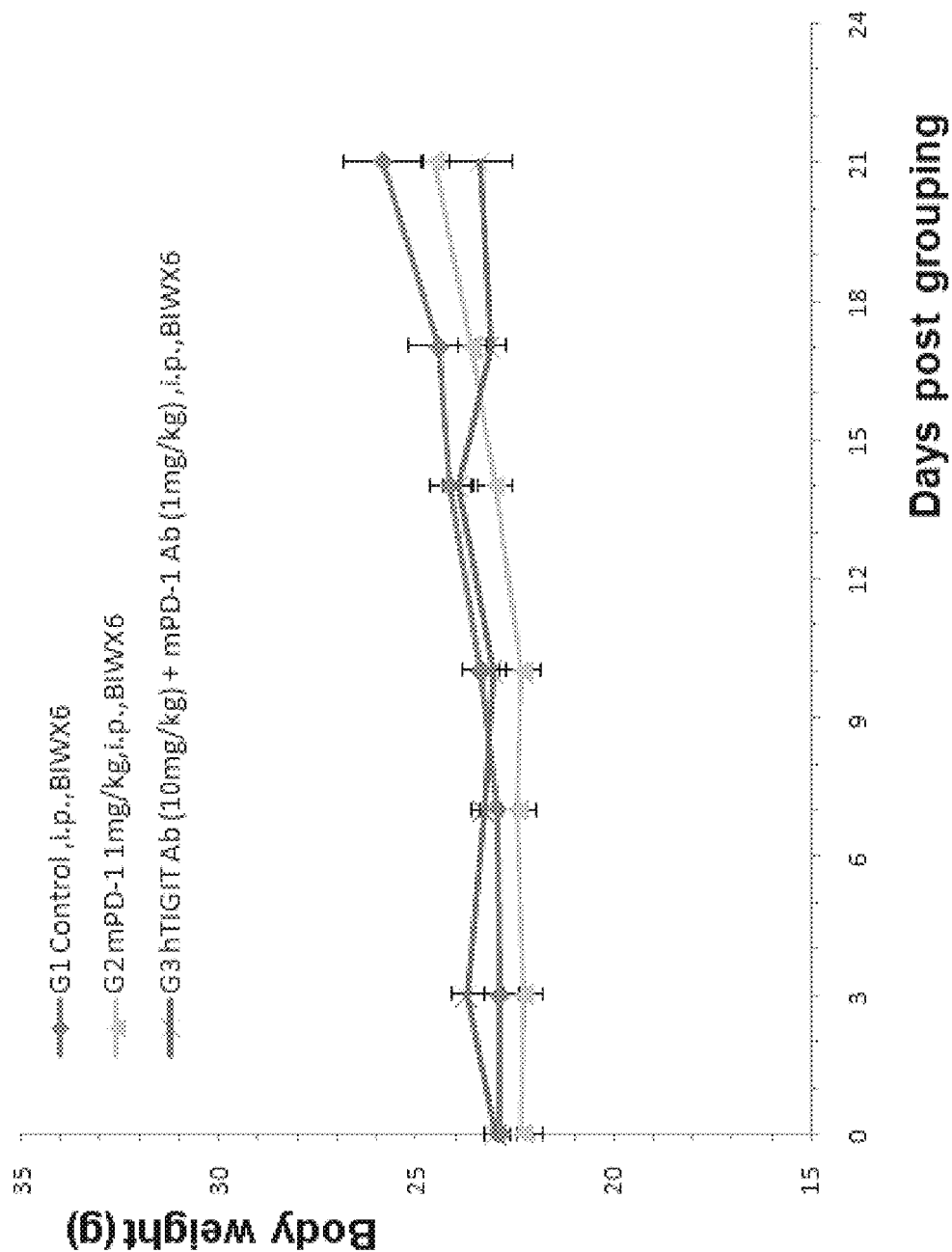
FIG. 16. Mouse colon cancer cells MC38 were injected into B-hTIGIT mice. Experiments were performed to test anti-tumor efficacy of anti-mouse PD-1 antibody mPD-1 Ab (G2) and the combination of mPD-1 Ab and anti-human TIGIT antibody hTIGIT Ab (G3). There was no significant difference in mean weight gain between different groups.
Figure 17:
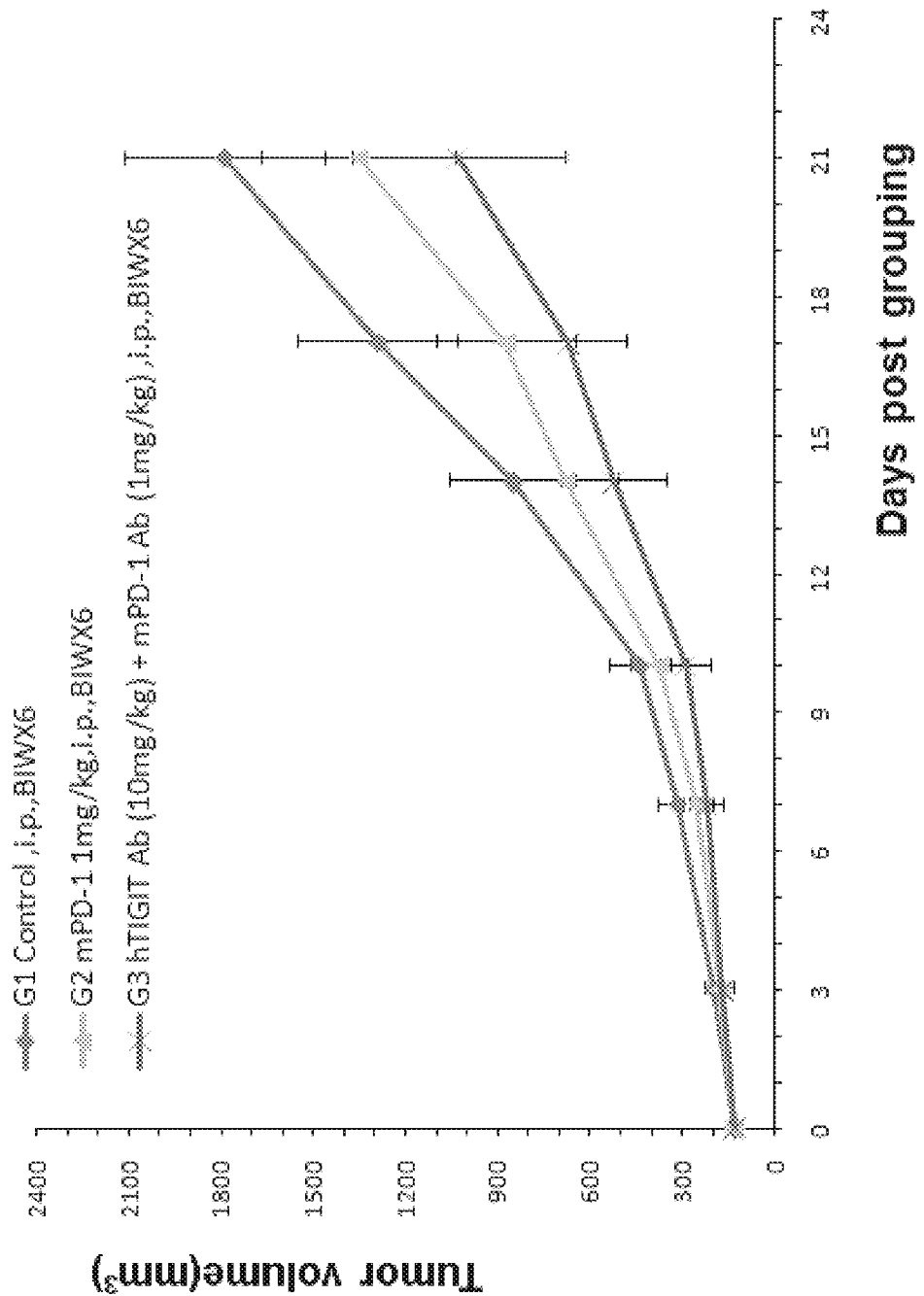
FIG. 17. Mouse colon cancer cells MC38 were injected into B-hTIGIT mice. Experiments were performed to test anti-tumor efficacy of anti-mouse PD-1 antibody mPD-1 Ab (G2) and the combination of mPD-1 Ab and anti-human TIGIT antibody hTIGIT Ab (G3). The average volumes of tumor in the G2 and G3 groups were smaller than that in G1 control group, and the average volume of tumor in the G3 group was smaller than that in the G2 group.

The above example has demonstrated that the B-hTIGIT mouse model can be used as an in vivo animal model for screening, evaluation and study of human TIGIT signaling pathway regulators, and test the efficacy of multiple anti-human TIGIT antibodies.

gains of the animals in each group were good. There was no significant difference in body weight (FIG. 16) between the treatment group and the control group (P>0.05). However, concerning the tumor volume (FIG. 17), the tumors of all of the control mice were growing continuously during the experimental period. In the treatment groups (G2 and G3), the tumor volume of each mouse became smaller by a

TABLE 7

|  |  | Tumor volume (mm³) | | | Survival | $TGI_{TV}\%$ | P value | |
|---|---|---|---|---|---|---|---|---|
|  |  | Day 0 | Day 15 | Day 19 |  |  | Body weight | Tumor Volume |
| Control | G1 | 200 ± 39 | 1395 ± 340 | 3319 ± 637 | 100% | N/A | N/A | N/A |
| Treatment | G2 TIGIT B1 | 201 ± 37 | 1036 ± 413 | 2150 ± 742 | 100% | 37.5 | 0.526 | 0.027 |
|  | G3 TIGIT B1 | 203 ± 33 | 1075 ± 199 | 2413 ± 987 | 100% | 29.2 | 0.559 | 0.123 |

Example 8. B-hTIGIT Humanized Animal Model for Combination Therapy Study

It has been shown in some studies that blocking TIGIT and other immunological checkpoints (such as PD-1, TIM-3) can produce synergistic effects, promote anti-tumor immunity and induce tumor regression (Anderson A C et al., Immunity. 2016 May 17; 44 (5): 989-1004). In this example, the anti-human TIGIT antibody was used in combination with anti-mouse PD-1 antibody to verify that the B-hTIGIT mice were useful for the study of combination therapy. B-hTIGIT homozygous mice (4-6 weeks old) were injected subcutaneously on right body side with 5×10⁵ mice colon cancer cell MC38. When the tumor volume has reached about 100 mm³, the mice were randomly divided into control group and treatment group (n=7/group). The treatment group mice received random injections of one or two of the anti-mouse PD-1 antibody mPD-1 Ab and the anti-human TIGIT antibody hTIGIT Ab at a dose of 1 to 10 mg/kg. The control group received blank solvent. The specific drug combinations and dosages were as follows: G1 was the control group, G2 received the injection of mPD-1 Ab (1 mg/kg), G3 received the injection of mPD-1 Ab (1 mg/kg) and hTIGIT Ab (10 mg/kg). The administration frequency was 2 times per week and a total of 6 times of administrations were provided. The tumor volume was measured twice a week and the mouse body weight was measured as well; euthanasia was performed when the tumor volume of the mouse reached 3000 mm³ after injection.

Overall, during the experiment the animals were in good health condition. At the end of the experiment, the weight certain degree, indicating with the treatments of various drugs and a combination thereof, the tumor growth in mouse body was clearly inhibited.

Table 6 lists the main data and analysis results for each experiment, including the tumor volume at the time of grouping and at 17 days after the grouping, the tumor volume at the end of the experiment (21 days after the grouping), the survival of the mice, the Tumor Growth Inhibition value ($TGI_{TV}$) and the difference between the body weight and the tumor volume of the treatment group and the control group (P value).

TABLE 8

|  |  | Tumor volume (mm³) | | | Survival | $TGI_{TV}\%$ | P value | |
|---|---|---|---|---|---|---|---|---|
|  |  | Day 0 | Day 17 | Day 21 |  |  | Body weight | Tumor volume |
| Control group | G1 | 130 ± 37 | 1290 ± 690 | 1790 ± 865 | 100% | N/A | N/A | N/A |
| Treatment group | G2 | 129 ± 45 | 877 ± 601 | 1354 ± 841 | 100% | 26.2 | 0.24 | 0.358 |
|  | G3 | 129 ± 47 | 670 ± 489 | 1030 ± 917 | 100% | 45.7 | 0.076 | 0.137 |

As shown in Table 6, each mouse in the control group and the treatment group was alive at the end of the experiment (21 days after grouping). In addition, there was no significant difference in body weight between the treatment group mice and the control group mice (P>0.05), indicating that the animals had good tolerance to anti-mouse PD-1 antibody mPD-1 Ab and anti-human TIGIT antibody hTIGIT Ab. At the end of the experiment, the average tumor volume of the control group (G1) was 1790±865 mm³, the average tumor volume of the treatment group (G2) with anti-mouse PD-1 antibody mPD-1 Ab alone was 1354±841 mm³, the average tumor volume of the treatment group (G3) with a combination of anti-mouse PD-1 antibody mPD-1 Ab and anti-human TIGIT antibody hTIGIT Ab was 1030±917 mm³, which show that the tumor volume of the treatment group (G3) with the combined treatment was significantly smaller than that of the mPD-1 Ab alone treatment group (G2). In addition, the $TGI_{TV}$ values also show that under the condition of the same administration frequency, the efficacy of the two antibodies in combination is superior to that of the individual antibody. Moreover, the co-treatment of anti-human TIGIT antibody hTIGIT Ab and anti-mouse PD-1 antibody mPD-1 Ab can more efficiently inhibit the tumor growth in mouse body.

The examples demonstrate that the B-hTIGIT mouse model is responsive to the combination of targeting human TIGIT antibodies and another antibody, confirming that B-hTIGIT mice can be used in the study of the combination of the modulators of human TIGIT signaling pathway with other drugs.

Example 9. Preparation and Identification of Double Humanized or Multiple Humanized Mice Mice containing the human TIGIT gene (such as the B-hTIGIT animal model prepared using the methods as described in the present disclosure) can also be used to prepare a double-humanized or multi-humanized animal model. For example, in Example 4, the fertilized egg cells used in the microinjection and embryo transfer process can be selected from the fertilized egg cells of other genetically modified mice or the fertilized egg cells of B-hTIGIT mice, so as to obtain TIGIT humanized and other gene modified double or multiple gene modified mouse models.

In addition, the B-hTIGIT animal model homozygote or heterozygote can be mated with other genetically modified homozygous or heterozygous animal models, and the progeny is then screened; according to the Mendelian law, there is a chance to obtain the TIGIT humanized and other gene modified double genes or multiple genes modified heterozygous animal models, and then the obtained heterozygous can be mated with each other to finally obtain the double genes or multiple genes modified homozygote.

In the case of the generating double humanized TIGIT/PD-1 mouse, since the mouse TIGIT gene and Pd-1 gene are located on different chromosomes, the double humanized TIGIT/PD-1 mouse was obtained by mating the B-hTIGIT mouse with B-hPD-1 mouse.

Figures 18A, 18B, 18C, 18D:
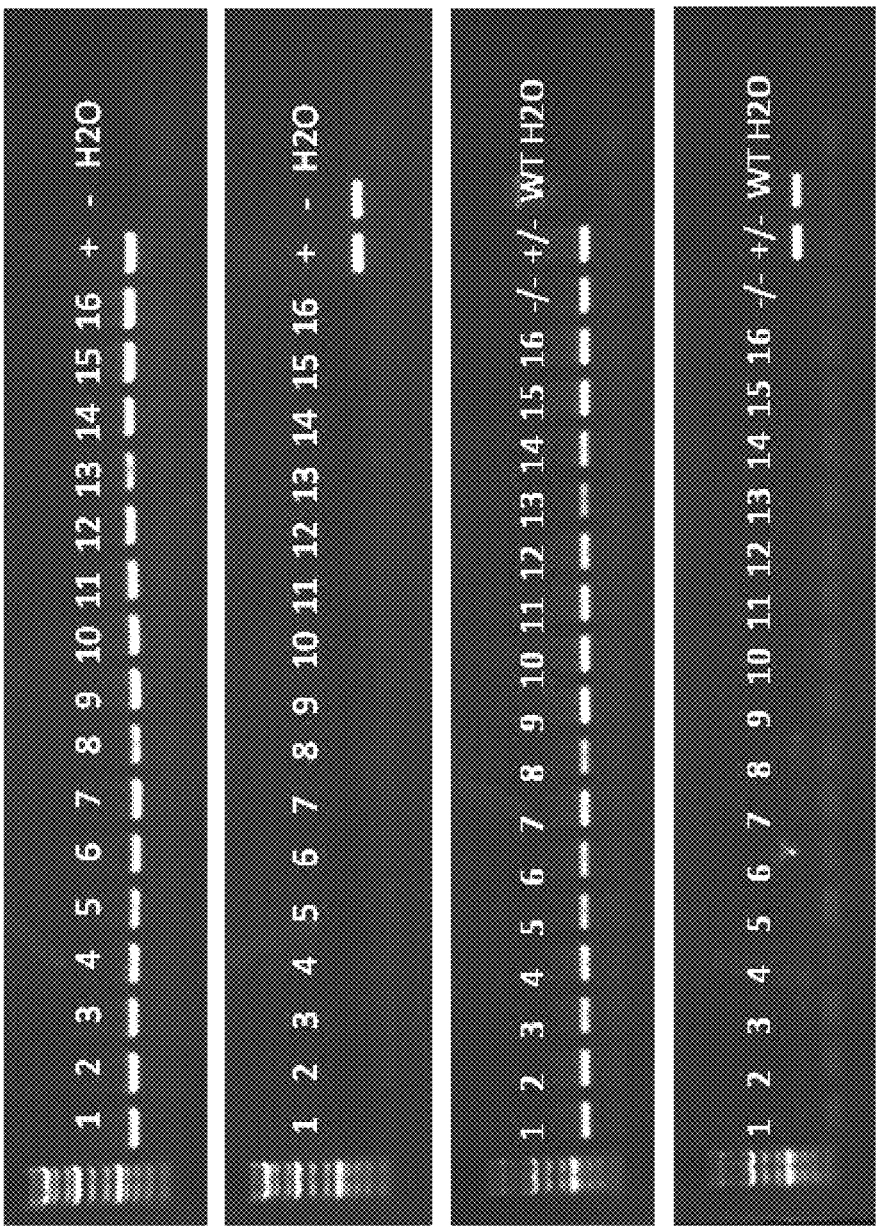
FIGS. 18A and 18B show that the mice numbered D-1 to D-16 are homozygous for humanized TIGIT gene.
FIGS. 18C and 18D show that the mice numbered D-1 to D-16 are homozygous for humanized PD-1 gene. The results show that the 16 mice numbered D-1 to D-16 are homozygous for both humanized genes.
Figures 19A, 19B, 19C, 19D, 19E, 19F:
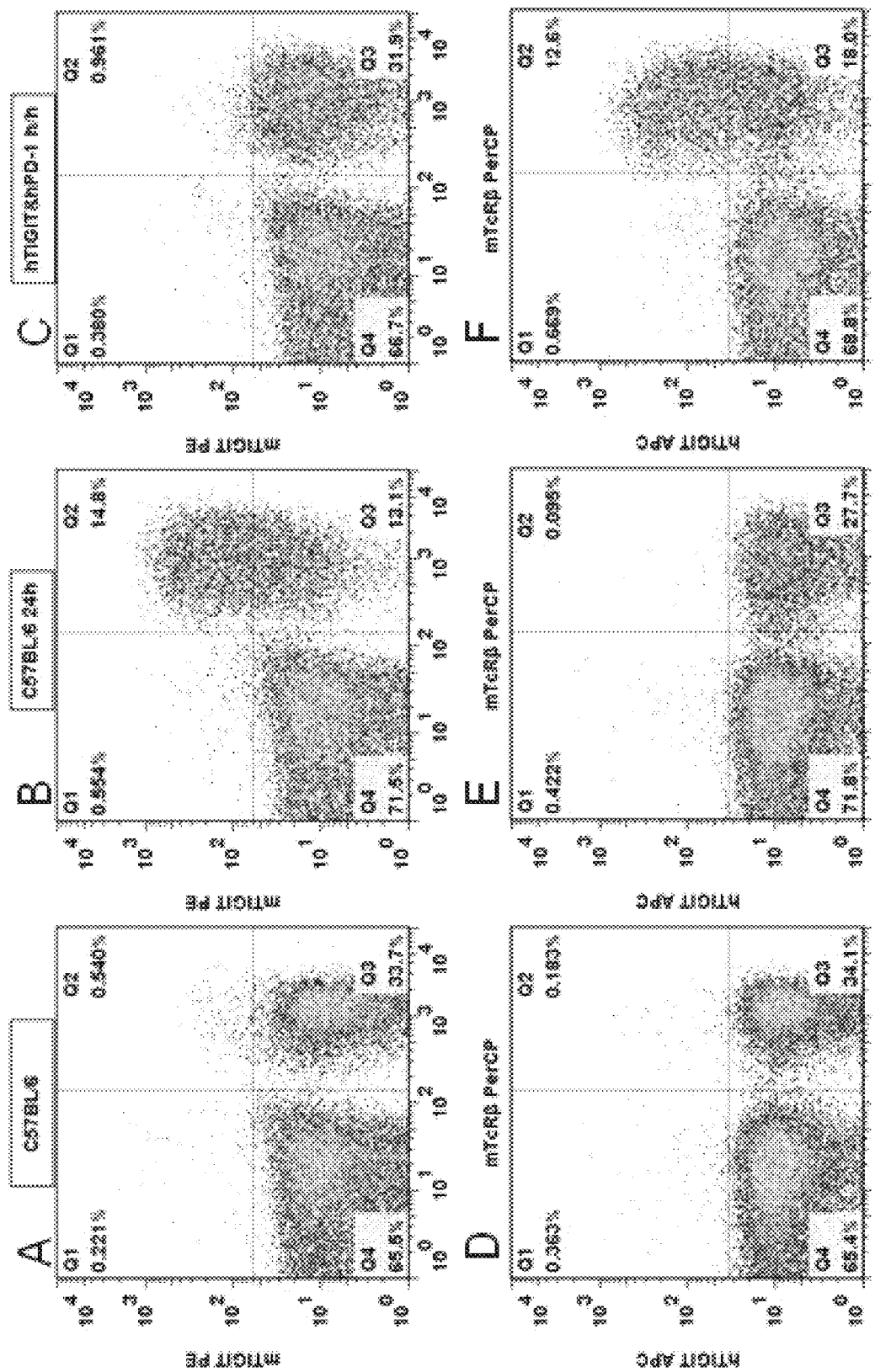
FIGS. 19A-19L are graphs showing flow cytometry analysis results for C57BL/6 mice and double humanized TIGIT/PD-1 homozygous mice. Anti-mouse CD3 antibody was used to stimulate T cell activation in the spleens of the mice, and then the mouse TIGIT antibody mTIGIT PE (FIGS. 19A, 19B, 19C), human TIGIT antibody hTIGIT APC (FIGS. 19D, 19E, 19F), mouse PD-1 antibody mPD-1 PE (FIGS. 19G, 19H, 19I), or human PD-1 antibody hPD-1 FITC (FIGS. 19I, 19K, 19L), and mouse T cell surface antigen antibody mTcRβ were used to label T cell proteins. The results show that the cells expressing humanized TIGIT and PD-1 proteins were detected in the spleens of double humanized TIGIT/PD-1 homozygous mouse, while no cells expressing humanized TIGIT or PD-1 protein were detected in the spleen of C57BL/6 control mice.
Figures 19G, 19H, 19I, 19J, 19K, 19L:
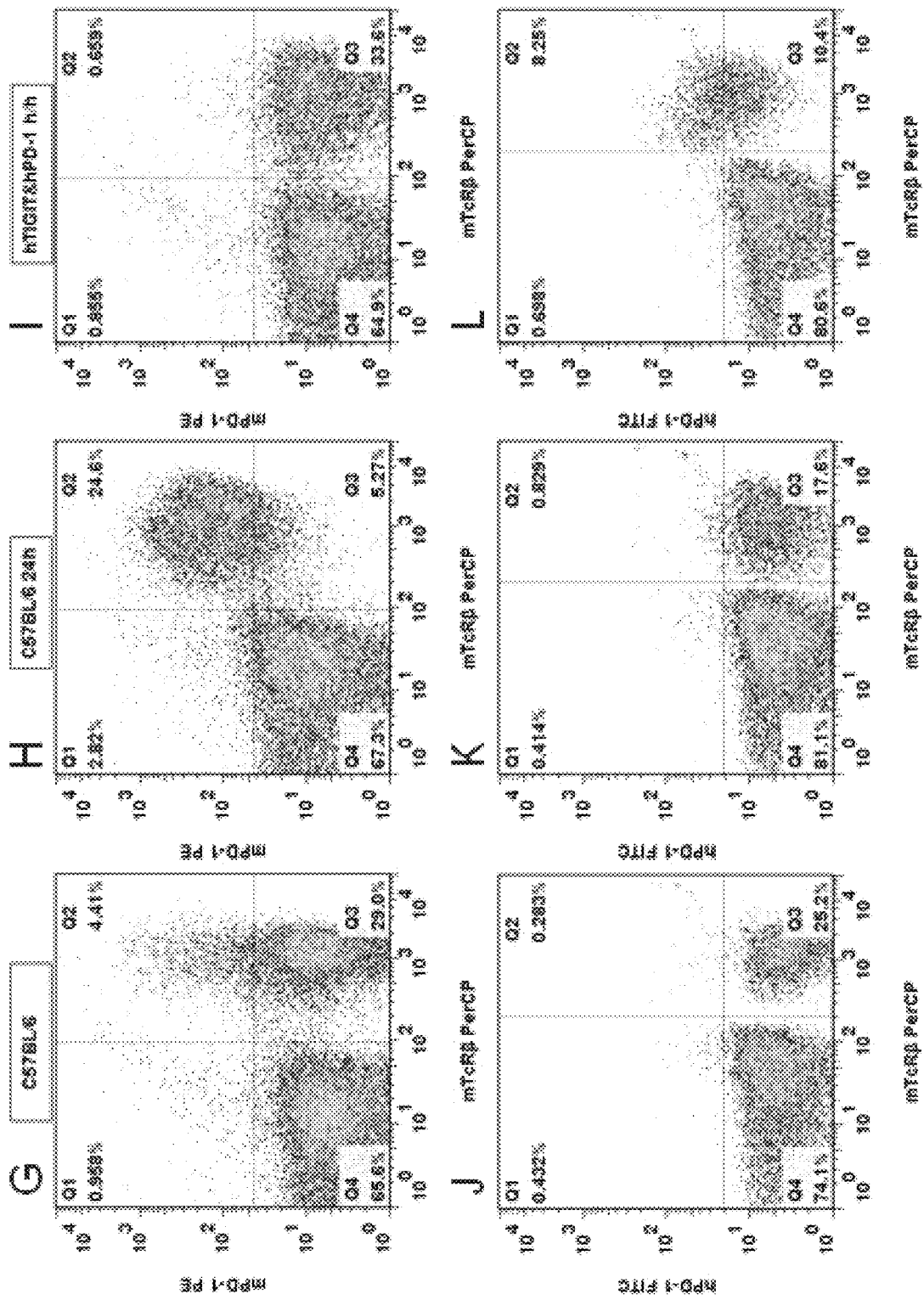

PCR analysis was performed on the mouse tail genomic DNA of double humanized TIGIT/PD-1 mice using four pairs of primers. The specific sequences and product lengths are shown in Table 7. The reaction system and reaction conditions are shown in Table 8 and Table 9. The results for a number of humanized TIGIT/PD-1 mice are shown in FIG. 18, wherein FIGS. 18A and 18B show that the mice numbered D-1 to D-16 are TIGIT homozygous mice, FIGS. 18C and 18D show that the mice numbered D-1 to D-16 are PD-1 homozygous mice. The results of the two groups indicate that the 16 mice of D-1 to D-16 were double gene homozygotes.

TABLE 9

| Primer sequences | | |
|---|---|---|
| Primer | Sequence | Product length |
| TIGIT WT | F: 5'-aggagagactgcagactgtg gacatc-3' (SEQ ID NO: 58) R: 5'-acttgggtcacttcagctgt gtcag-3' (SEQ ID NO: 59) | WT: 240 bp |
| TIGIT MUT | F: 5'-gctgaccgtgaacgatacag gg-3' (SEQ ID NO: 60) R: 5'-gaatcggctggttgtttctg gaacg-3' (SEQ ID NO: 61) | Mut: 324 bp |

TABLE 9-continued

| Primer sequences | | |
|---|---|---|
| Primer | Sequence | Product length |
| PD-1 MUT | F: 5'-cttccacatgagcgtggtca gggcc-3' (SEQ ID NO: 62) R: 5'-ccaagggactattttagatg ggcag-3' (SEQ ID NO: 63) | Mut: 325 bp |
| PD-1 WT | F: 5'-gaagctacaagctcctaggt aggggg-3' (SEQ ID NO: 64) R: 5'-acgggttggctcaaaccatt aca-3' (SEQ ID NO: 65) | WT: 345 bp |

TABLE 10

| PCT reaction | |
|---|---|
| 2x Master Mix | 10 μL |
| Upstream primer (10 μM) | 0.5 μL |
| Downstream primer (10 μM) | 0.5 μL |
| Mouse tail genomic DNA (100-200 ng/20 ml) | 2 μL |
| ddH$_2$O | Add to to 20 μL |

TABLE 11

| PCR amplification reaction condition | | |
|---|---|---|
| Temperature | Time | Cycles |
| 95□ | 5 min | 1 |
| 95□ | 30 sec | 30 |
| 59□ | 30 sec | |
| 72□ | 30 sec | |
| 72□ | 10 min | 1 |
| 4□ | 10 min | 1 |

The expression of the double humanized TIGIT/PD-1 mice was further examined. A double humanized TIGIT/PD-1 homozygote (6 weeks old) was selected for the study. Two wild type C57BL/6 mice were selected as control. Mice were injected with 7.5 μg of mouse CD3 antibody intraperitoneally. After 24 hours, the mice were euthanized, and then the spleens of the mice were collected. The spleen samples were ground and the ground samples were filtered through a 70 μm cell mesh. The filtered cell suspensions were centrifuged and the supernatants were discarded; erythrocyte lysis solution was added for lysis for 5 min, and then PBS solution was added to neutralize the lysis reaction. The solution was centrifuged again and the supernatants were discarded, the cells were washed once with PBS. The obtained spleen cell samples were then subject to FACS and RT-PCR analysis.

FACS detection: The T cells extracellular proteins were simultaneously stained with anti-mouse TIGIT antibody mTIGIT PE (FIGS. 19A, 19B, 19C), anti-human TIGIT antibody hTIGIT APC (FIGS. 19D, 19E, 19F), anti-mouse PD-1 antibody mPD-1 PE (FIGS. 19G, 19H, and 19I), or anti-human PD-1 antibody hPD-1 FITC (FIGS. 19I, 19K, 19L), and mouse T cell surface antibody mTcRβ. The cells were then washed with PBS and then detected for protein expression by FACS detection. Flow cytometry analysis results are shown in FIGS. 19A-19L. When compared with the C57BL/6 mice with or without the stimulation of CD3 antibody for T cell activation in spleen, the anti-human TIGIT antibody and the anti-human PD-1 antibody can detect the cells expressing humanized TIGIT and humanized PD-1 in humanized TIGIT/PD-1 homozygotes. In contrast, the anti-human TIGIT antibody and the anti-human PD-1 antibody cannot detect the cells expressing humanized TIGIT and humanized PD-1 in in the spleen samples from the C57BL/6 control mice.

RT-PCR detection: total RNA was extracted from the spleen cells of wild-type C57BL/6 mice and humanized TIGIT/PD-1 homozygotes. cDNAs were then obtained by reverse transcription using a reverse transcription kit.

```
mTIGIT RT-PCR primer F1 (SEQ ID NO: 52) and
mTIGIT RT-PCR primer R1 (SEQ ID NO: 53)
were used to amplify mouse TIGIT fragment of
175 bp.

hTIGIT RT-PCR primer F1 (SEQ ID NO: 54), and
hTIGIT RT-PCR primer R1 (SEQ ID NO: 55)
were used to amplify human TIGIT fragment of
171 bp.

mPD-1 RT-PCR primer F3:
                                    (SEQ ID NO: 66)
5'-CCTGGCTCACAGTGTCAGAG-3',
and mPD-1 RT-PCR primer R3:
                                    (SEQ ID NO: 67)
5'-CAGGGCTCTCCTCGATTTTT-3'
were used to amplify mouse PD-1 fragment of
297 bp.

hPD-1 RT-PCR primer F3:
                                    (SEQ ID NO: 68)
5'-CCCTGCTCGTGGTGACCGAA-3',
and hPD-1 RT-PCR primer R3:
                                    (SEQ ID NO: 69)
5'-GCAGGCTCTCTTTGATCTGC-3'
were used to amplify human PD-1 fragment
of 297 bp.
```

PCR reaction system was 20 µL, reaction conditions: 95° C., 5 min; (95° C., 30 sec; 60° C., 30 sec; 72° C., 30 sec, 35 cycles); 72° C., 10 min; and 4° C. GAPDH was used as an internal reference.

Figure 20:
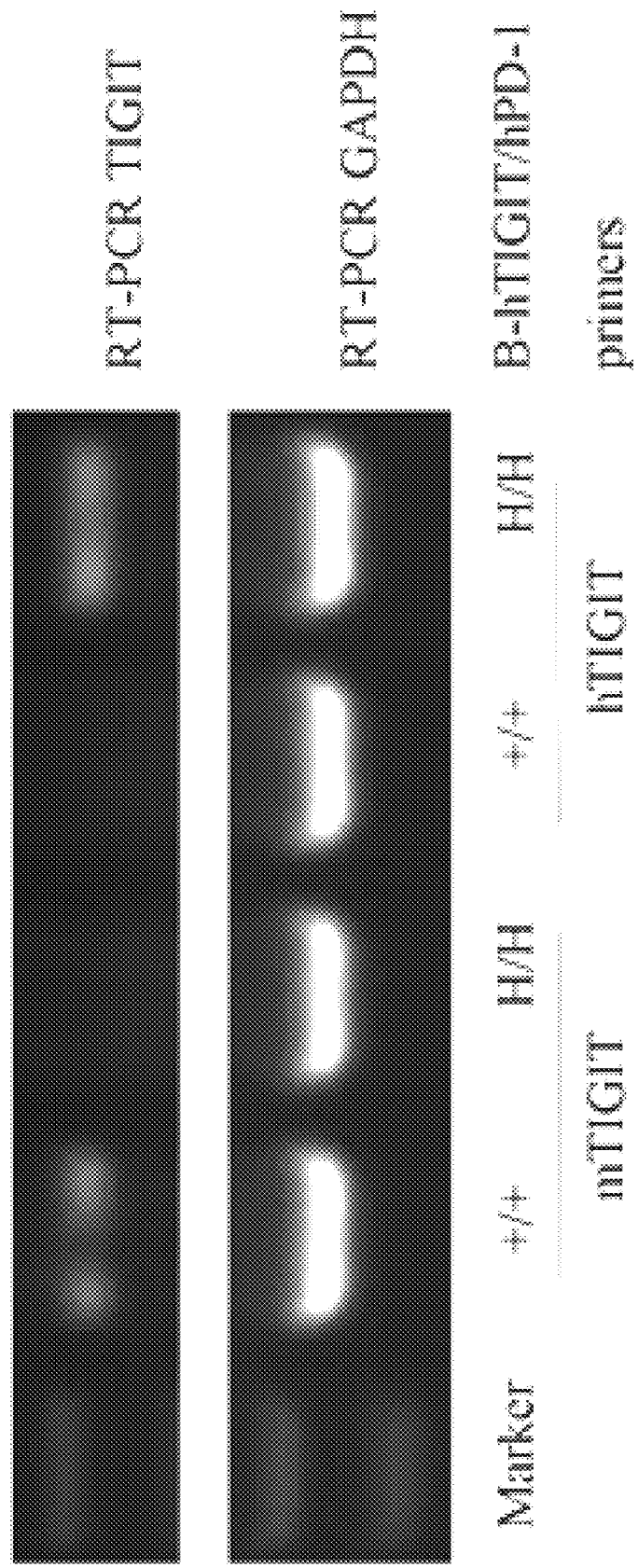
FIG. 20 shows RT-PCR detection results, wherein +/+ is wild type C57BL/6 mouse; H/H is humanized TIGIT/PD-1 homozygous mouse; and GAPDH is an internal control. Mouse TIGIT mRNA was detected in C57BL/6 mice; and human TIGIT mRNA was detected in humanized TIGIT/PD-1 homozygous mouse.
Figure 21:
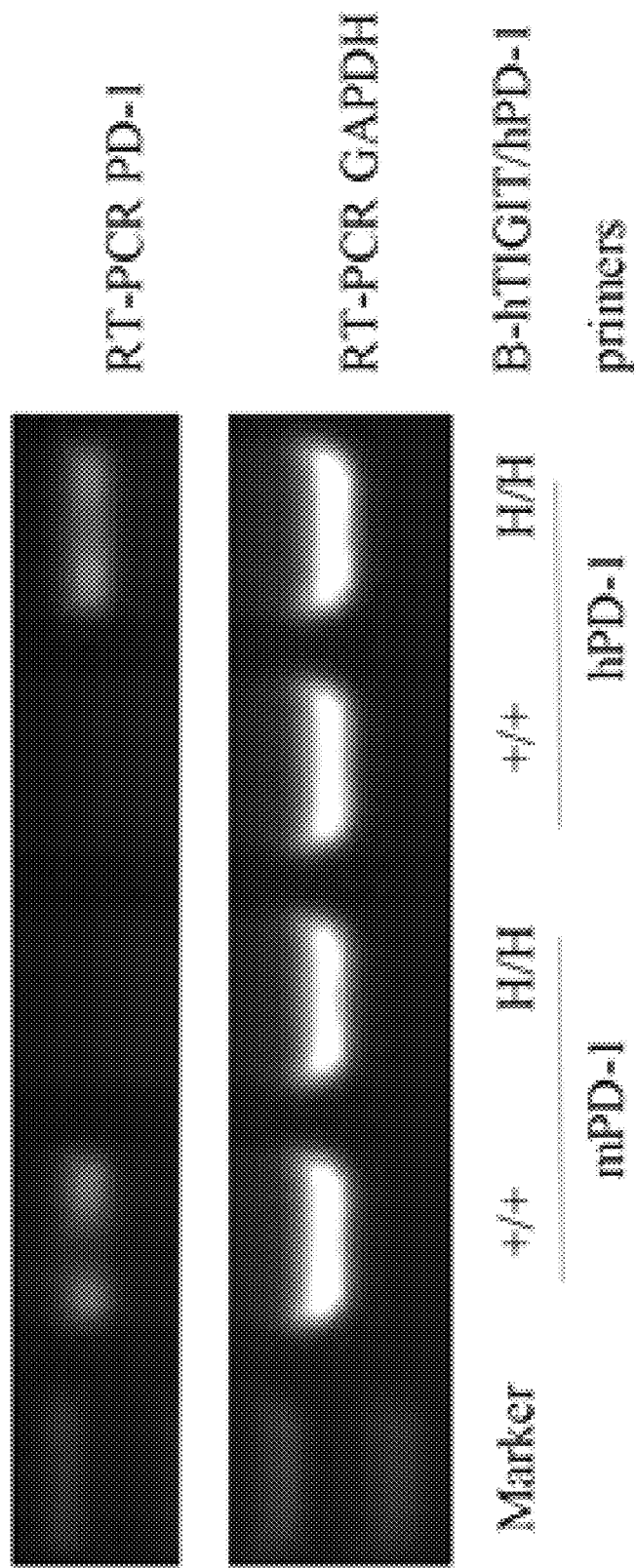
FIG. 21 shows RT-PCR detection results, wherein +/+ is wild type C57BL/6 mouse; H/H is humanized TIGIT/PD-1 homozygous mouse; and GAPDH is an internal control.

The results are shown in FIGS. 20 and 21. The mRNA expression of mouse TIGIT and PD-1 can be detected in the activated cells of wild-type C57BL/6 mice; while the mRNA expression of human TIGIT and PD-1 can be detected in the activated cells of humanized TIGIT/PD-1 homozygous mice.

Example 11. Preparation Method Based on Embryonic Stem Cells

The non-human mammals can also be prepared through other gene editing systems and approaches, which includes, but is not limited to, gene homologous recombination techniques based on embryonic stem cells (ES), zinc finger nuclease (ZFN) techniques, transcriptional activator-like effector factor nuclease (TALEN) technique, homing endonuclease (megakable base ribozyme), or other molecular biology techniques. In this example, the conventional ES cell gene homologous recombination technique is used as an example to describe how to obtain a TIGIT gene humanized mouse by other methods. According to the gene editing strategy of the methods described herein and the humanized mouse TIGIT gene map (FIG. 4), a targeting strategy has been developed as shown in FIG. 24. FIG. 24 shows the design of the recombinant vector. In view of the fact that one of the objects is to replace the exon 2 of the mouse TIGIT gene in whole or in part with the human TIGIT gene fragment, a recombinant vector that contains a 5' homologous arm (4481 bp), a 3' homologous arm (4003 bp) and a humanized gene fragment (312 bp) is also designed. The vector can also contain a resistance gene for positive clone screening, such as neomycin phosphotransferase coding sequence Neo. On both sides of the resistance gene, two site-specific recombination systems in the same orientation, such as Frt or LoxP, can be added. Furthermore, a coding gene with a negative screening marker, such as the diphtheria toxin A subunit coding gene (DTA), can be constructed downstream of the recombinant vector 3' homologous arm. Vector construction can be carried out using methods known in the art, such as enzyme digestion and so on. The recombinant vector with correct sequence can be next transfected into mouse embryonic stem cells, such as C57BL/6 mouse embryonic stem cells, and then the recombinant vector can be screened by positive clone screening gene. The cells transfected with the recombinant vector are next screened by using the positive clone marker gene, and Southern Blot technique can be used for DNA recombination identification. For the selected correct positive clones, the positive clonal cells (black mice) are injected into the isolated blastocysts (white mice) by microinjection according to the method described in the book A. Nagy, et al., "Manipulating the Mouse Embryo: A Laboratory Manual (Third Edition)," Cold Spring Harbor Laboratory Press, 2003. The resulting chimeric blastocysts formed following the injection are transferred to the culture medium for a short time culture and then transplanted into the fallopian tubes of the recipient mice (white mice) to produce F0 generation chimeric mice (black and white). The F0 generation chimeric mice with correct gene recombination are then selected by extracting the mouse tail genome and detecting by PCR for subsequent breeding and identification. The F1 generation mice are obtained by mating the F0 generation chimeric mice with wild type mice. Stable gene recombination positive F1 heterozygous mice are selected by extracting rat tail genome and PCR detection. Next, the F1 heterozygous mice are mated to each other to obtain genetically recombinant positive F2 generation homozygous mice. In addition, the F1 heterozygous mice can also be mated with Flp or Cre mice to remove the positive clone screening marker gene (neo, etc.), and then the TIGIT gene humanized homozygous mice can be obtained by mating these mice with each other. The methods of genotyping and phenotypic detection of the obtained F1 heterozygous mice or F2 homozygous mice are similar to those used in Example 5 described above.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically-modified mouse whose genome comprises a nucleic acid sequence encoding a chimeric T cell immunoreceptor with Ig and ITIM domains (TIGIT) at an endogenous TIGIT gene locus, wherein the chimeric TIGIT comprises a humanized TIGIT extracellular region, an endogenous transmembrane region and an endogenous cytoplasmic region, wherein the chimeric TIGIT comprises the amino acids sequence as set forth in SEQ ID NO: 34, and the nucleic acid sequence encoding the chimeric TIGIT is operably linked to an endogenous regulatory element at the endogenous TIGIT locus, wherein the mouse expresses the chimeric TIGIT and does not express endogenous TIGIT, wherein an anti-human TIGIT antibody can bind to the expressed chimeric TIGIT and block the interaction of the chimeric TIGIT with a TIGIT ligand, thereby increasing immune response.

2. The genetically modified mouse of claim 1, wherein the mouse further comprises a nucleic acid sequence encoding chimeric programmed cell death protein 1 (PD-1).

3. A method of determining effectiveness of an anti-TIGIT antibody for treating cancer, comprising:
    administering the anti-TIGIT antibody to the mouse of claim 1, wherein the mouse has a cancer; and
    determining inhibitory effects of the anti-TIGIT antibody to the cancer.

4. The method of claim 3, wherein the cancer comprises one or more human cancer cells that are injected into the mouse.

5. The method of claim 3, wherein the anti-TIGIT antibody is an anti-human TIGIT antibody.

* * * * *